(12) United States Patent
Denney, Jr. et al.

(10) Patent No.: US 11,471,063 B2
(45) Date of Patent: Oct. 18, 2022

(54) INFORMATION PROCESSING METHOD, DEVICE, AND SYSTEM FOR EVALUATING BLOOD VESSELS

(71) Applicants: Auburn University, Auburn, AL (US); Arcus-Med, LLC, Raleigh, NC (US); The UAB Research Foundation, Birmingham, AL (US)

(72) Inventors: Thomas S. Denney, Jr., Auburn, AL (US); Himanshu Gupta, Ridgewood, NJ (US); Ankur Gupta, Detroit, MI (US)

(73) Assignees: Auburn University, Auburn, AL (US); Arcus-Med, LLC, Raleigh, NC (US); The UAB Research Foundation, Birmingham, AL (US)

( * ) Notice: Subject to any disclaimer, the term of this patent is extended or adjusted under 35 U.S.C. 154(b) by 139 days.

(21) Appl. No.: 16/900,734

(22) Filed: Jun. 12, 2020

(65) Prior Publication Data

US 2020/0305730 A1 Oct. 1, 2020

Related U.S. Application Data

(63) Continuation-in-part of application No. 15/808,891, filed on Nov. 10, 2017, now Pat. No. 10,893,809.
(Continued)

(51) Int. Cl.
*A61B 5/026* (2006.01)
*A61B 5/0285* (2006.01)
(Continued)

(52) U.S. Cl.
CPC .......... *A61B 5/0263* (2013.01); *A61B 5/021* (2013.01); *A61B 5/02007* (2013.01);
(Continued)

(58) Field of Classification Search
None
See application file for complete search history.

(56) References Cited

U.S. PATENT DOCUMENTS

| 5,715,826 A | 2/1998 | Horrocks et al. |
| 2009/0018449 A1 | 1/2009 | Raju |

(Continued)

OTHER PUBLICATIONS

First Office Action for Chinese Pat Appl No. 201780068883.1A (National Entry Application of PCT/US2017/060979, related to U.S. Appl. No. 15/808,891, now U.S. Pat. No. 10,893,809), dated Aug. 26, 2021.

(Continued)

*Primary Examiner* — Shahdeep Mohammed
(74) *Attorney, Agent, or Firm* — Junjie Feng

(57) ABSTRACT

A computerized information processing method for evaluating blood vessels is provided. The method includes acquiring a series of sequences of measurements, each at different time points in at least one cardiac cycle and at a different point along a blood vessel segment of a subject, generating corresponding profiles, calculating a transfer function for a subsegment between two selected points along a blood flow direction, and based thereon determining the physiological property of the subsegment. The measurements can contain information of blood velocity or blood pressure. A processing device and system implementing the information processing method are also provided. This approach can be used to evaluate arteries or veins and can be applied in screening, diagnosis, or prognosis of a variety of vascular diseases. For example, when combined with MRI scan, this approach can be used for non-invasively diagnosing pulmonary hypertension (PH) and chronic obstructive pulmonary disease (COPD), etc.

20 Claims, 36 Drawing Sheets

Related U.S. Application Data

(60) Provisional application No. 62/420,366, filed on Nov. 10, 2016.

(51) Int. Cl.
    *A61B 5/0245*     (2006.01)
    *A61B 5/055*     (2006.01)
    *A61B 5/02*     (2006.01)
    *A61B 5/021*     (2006.01)
    *A61B 8/08*     (2006.01)
    *A61B 8/06*     (2006.01)
    *A61B 8/04*     (2006.01)
    *A61B 5/00*     (2006.01)
    *G01R 33/56*     (2006.01)
    *G01R 33/567*     (2006.01)
    *G01R 33/563*     (2006.01)

(52) U.S. Cl.
CPC .......... *A61B 5/0245* (2013.01); *A61B 5/0285* (2013.01); *A61B 5/055* (2013.01); *A61B 5/7246* (2013.01); *G01R 33/5601* (2013.01); *G01R 33/5635* (2013.01); *G01R 33/5673* (2013.01); *A61B 5/681* (2013.01); *A61B 5/6852* (2013.01); *A61B 8/04* (2013.01); *A61B 8/06* (2013.01); *A61B 8/488* (2013.01)

(56) References Cited

U.S. PATENT DOCUMENTS

| | | | |
|---|---|---|---|
| 2011/0137183 A1* | 6/2011 | Stok | A61B 5/02116 600/485 |
| 2013/0158403 A1* | 6/2013 | Gottschalk | A61B 8/06 600/447 |
| 2014/0088406 A1* | 3/2014 | Dharmakumar | G01R 33/60 600/411 |
| 2014/0114184 A1 | 4/2014 | Klaiman et al. | |
| 2015/0018632 A1* | 1/2015 | Khair | A61B 5/14546 600/301 |
| 2015/0065864 A1* | 3/2015 | Sharma | A61B 5/0263 600/416 |
| 2016/0000341 A1 | 1/2016 | Rotman et al. | |

OTHER PUBLICATIONS

Simone Balocco, Olivier Basset, et al. "Estimation of the viscoelastic properties of vessel walls using a computational model and Doppler ultrasound", Phys Med Biol. Jun. 21, 2010; 55(23): 3557-75.

Notice of Refusal for Japanese Pat Appl. 2019522389A (currently Japanese Pat No. 6888086, which is the National Entry Application of PCT/US2017/060979, related to U.S. Appl. No. 15/808,891, now U.S. Pat. No. 10,893,809), dated Nov. 17, 2020.

Written Opinion for Japanese Pat Appl. 2019522389A (currently Japanese Pat No. 6888086, which is the National Entry Application of PCT/US2017/060979, related to U.S. Appl. No. 15/808,891, now U.S. Pat. No. 10,893,809), dated Feb. 10, 2021.

Office Action for Canadian Pat Appl. 3,082,253 (National Entry Application of PCT/US2017/060979, related to U.S. Appl. No. 15/808,891, now U.S. Pat. No. 10,893,809), dated Aug. 17, 2021.

Lu S, Ju KH, Chon KH. A new algorithm for linear and nonlinear ARMA model parameter estimation using affine geometry. IEEE Trans Biomed Eng. Oct. 2001;48(10):1116-24.

* cited by examiner

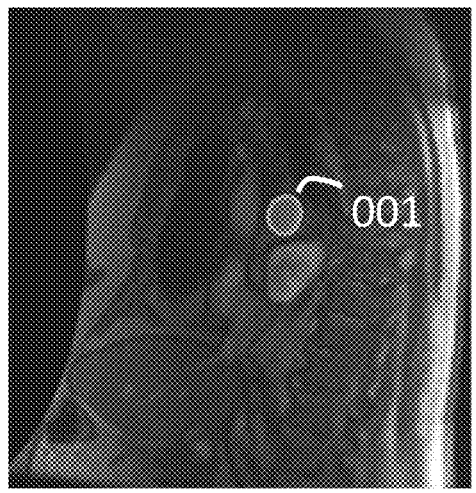
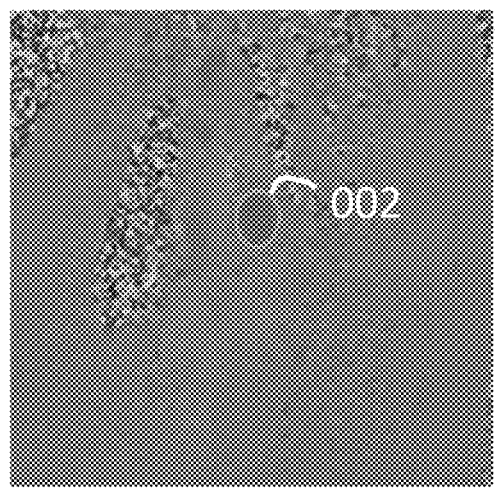
FIG. 2A  FIG. 2B
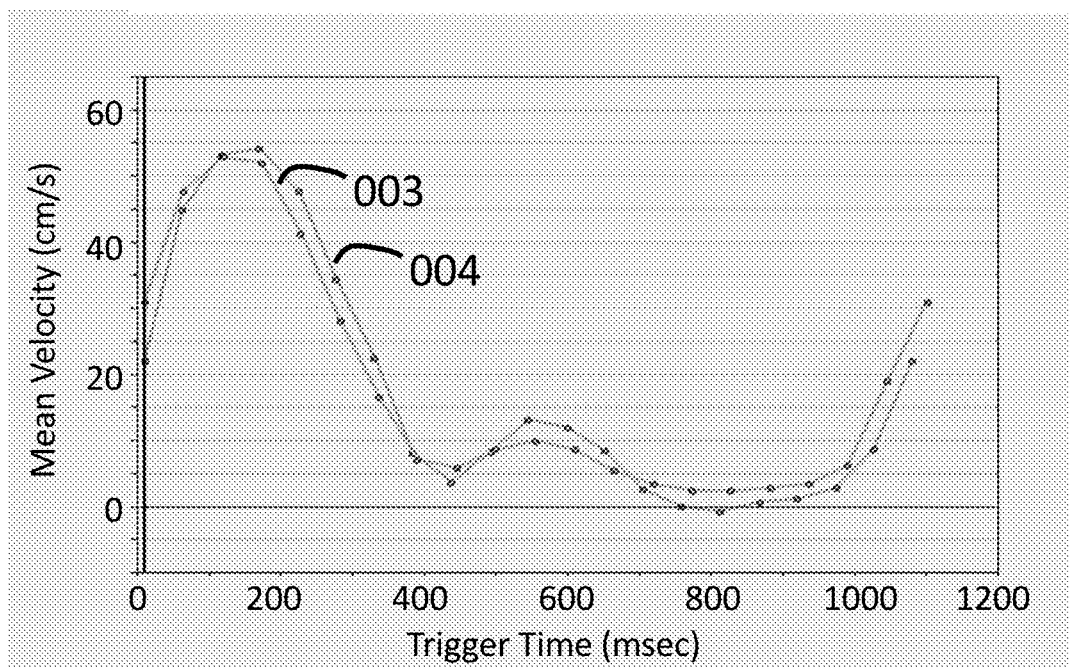
FIG. 3

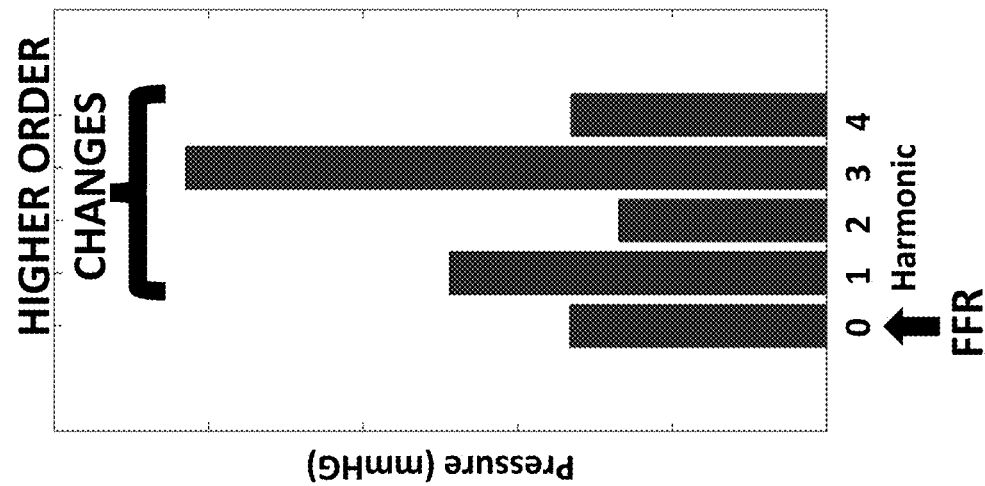
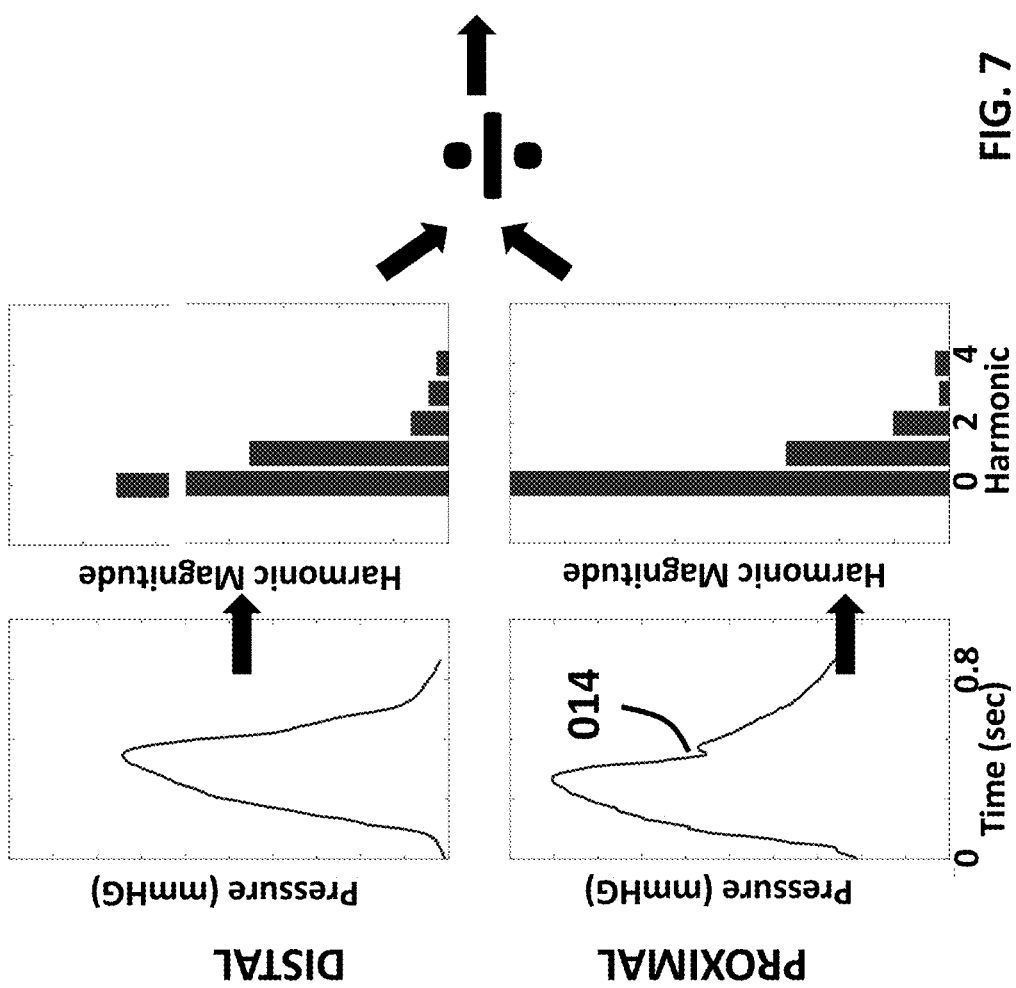
FIG. 7

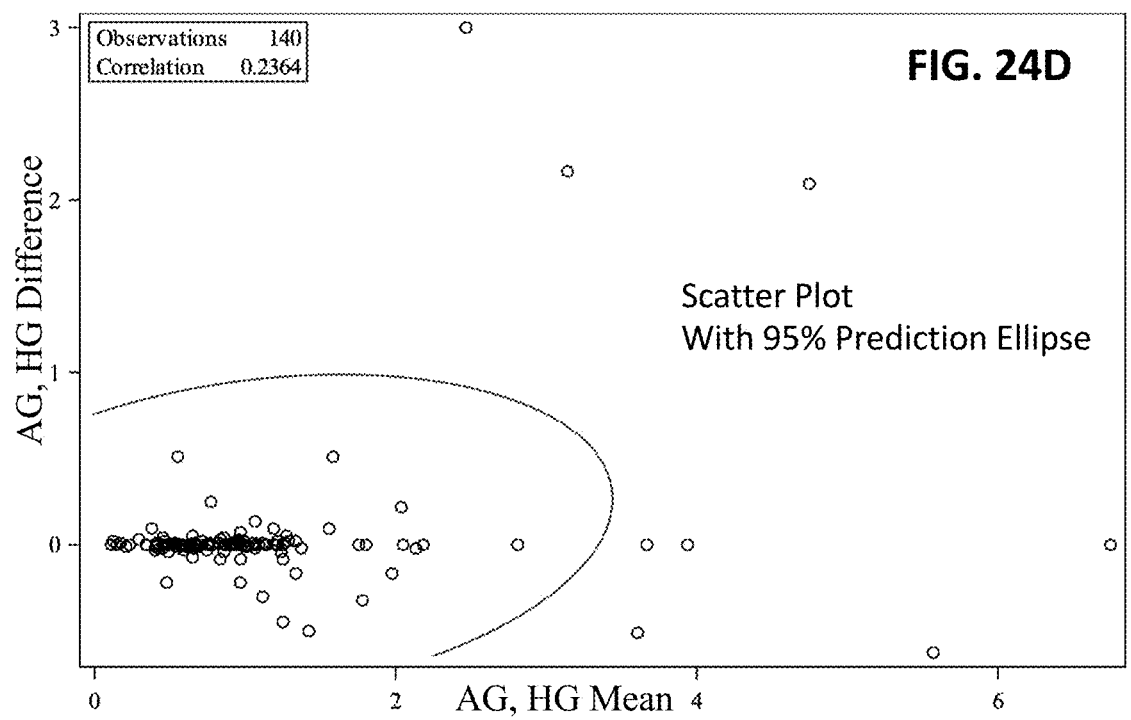

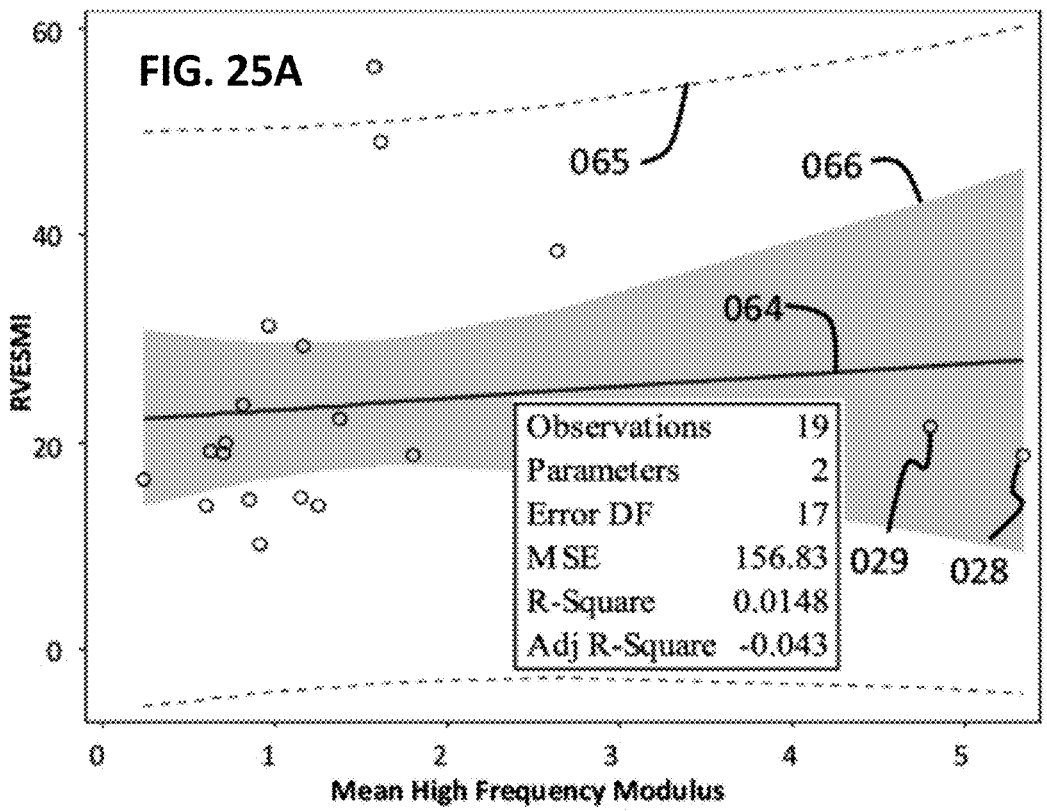
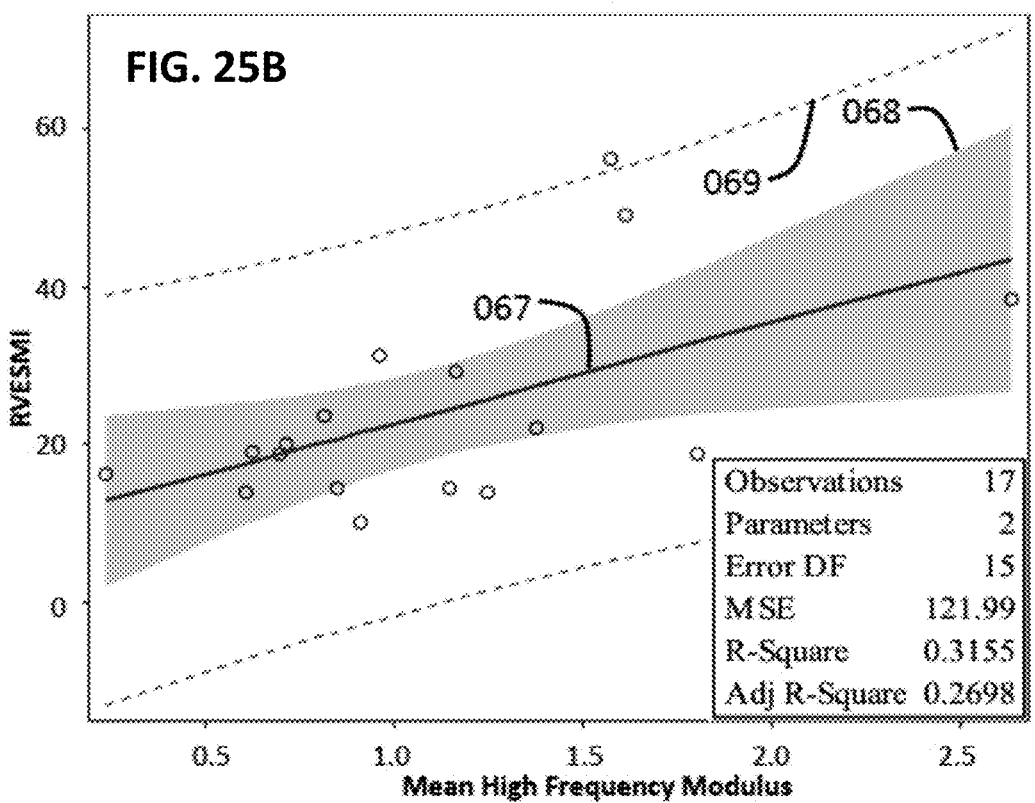

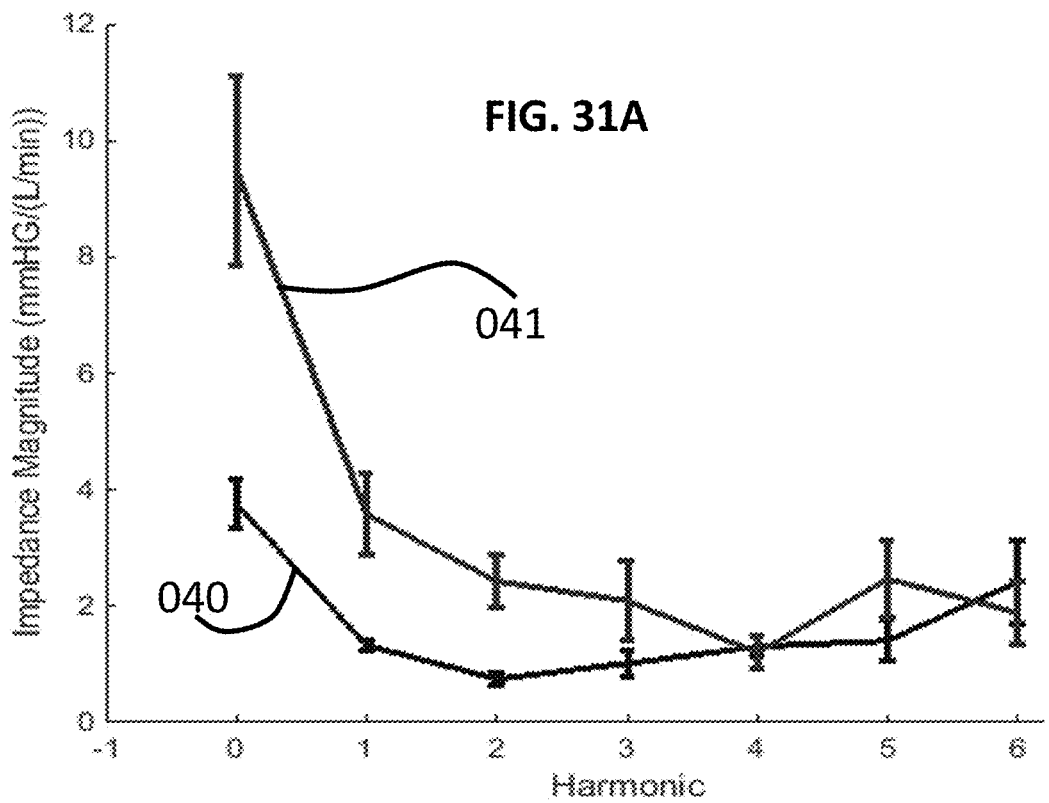
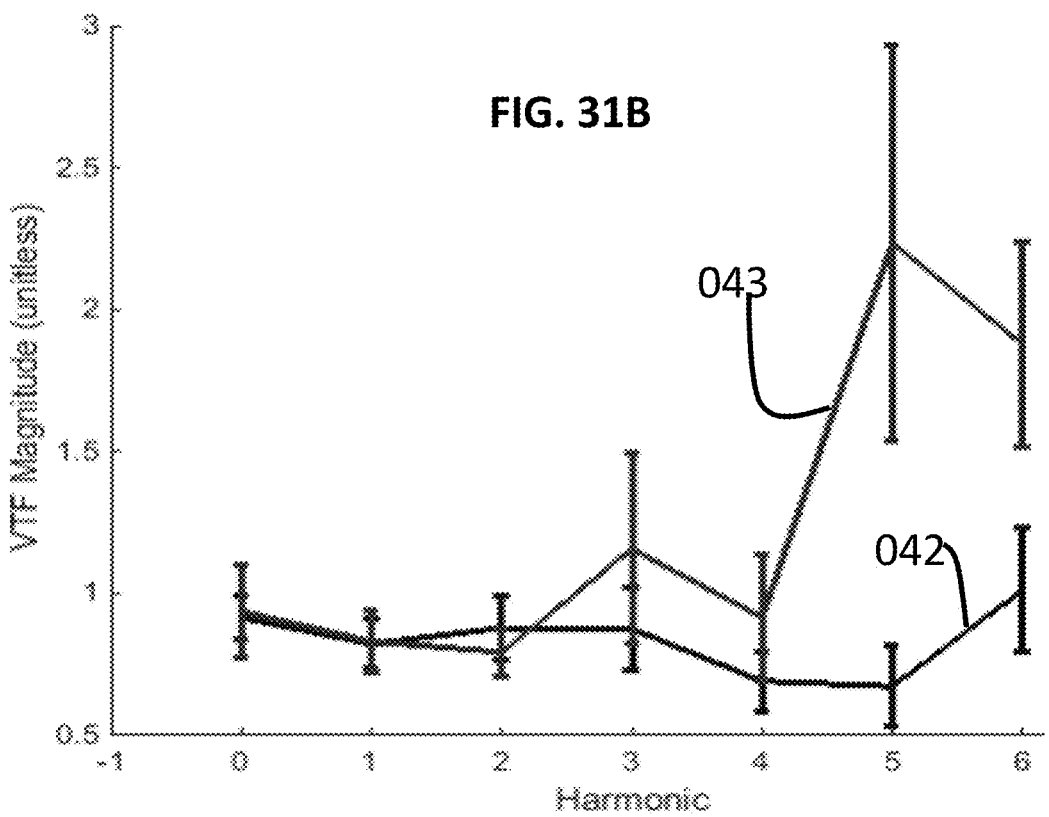

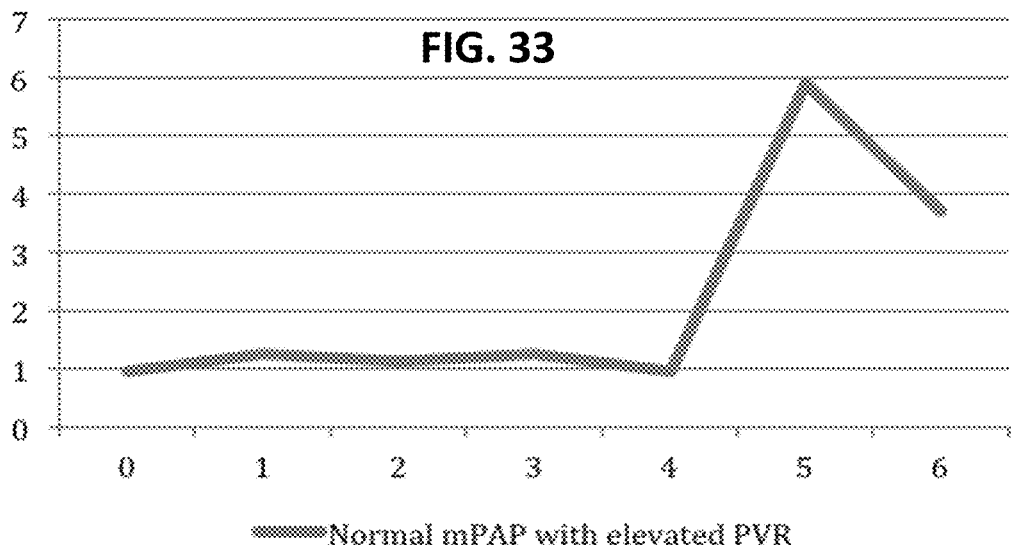
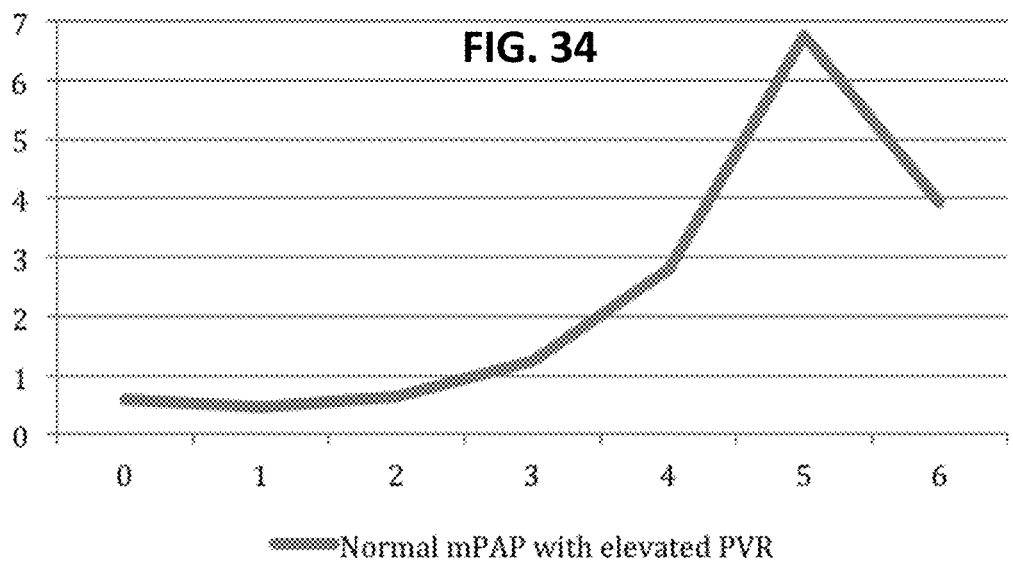
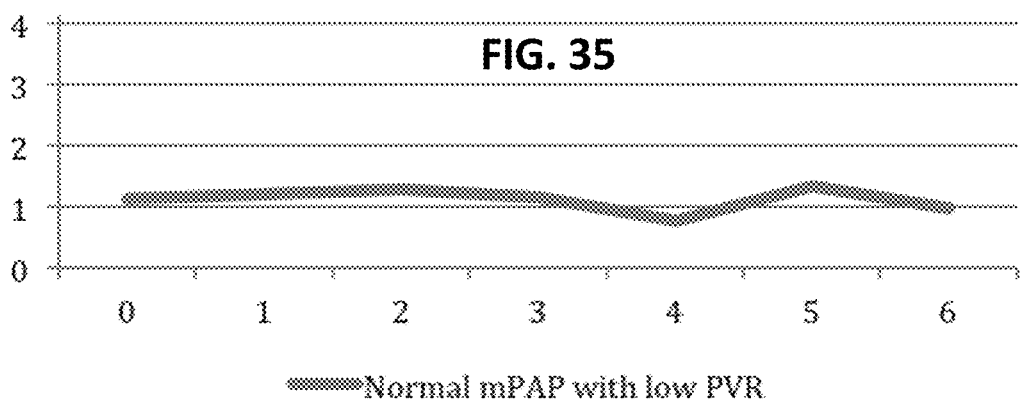

Normal mPAP with low PVR

High wedge with low PVR

High wedge with high PVR

INFORMATION PROCESSING METHOD, DEVICE, AND SYSTEM FOR EVALUATING BLOOD VESSELS

CROSS-REFERENCE TO RELATED APPLICATIONS

The present application is a continuation-in-part application of U.S. patent application Ser. No. 15/808,891 filed on Nov. 10, 2017, currently pending, which claims the benefit of U.S. Provisional Application No. 62/420,366 filed on Nov. 10, 2016. The disclosures of all of these applications are hereby incorporated by reference in their entirety.

STATEMENT REGARDING FEDERALLY SPONSORED RESEARCH

This invention was made with government support under HL104018 and UL1TR003096 awarded by the National Institutes of Health. The government has certain rights in the invention.

TECHNICAL FIELD

The present invention relates generally to the field of medical diagnostics, specifically to a method for evaluating blood vessel, and in more particular to an information processing method, device, system, and storage medium implementing the blood vessel evaluation method.

BACKGROUND

Normal arteries are elastic and expand during ventricular systole in response to increased blood flow and then recoil to their original state. Many diseases result from changes to the compliance and other arterial material properties. Arteries can become stiff due to atherosclerosis or increased blood pressure, as in pulmonary hypertension (PH), or become occluded with lesions, as in coronary artery diseases. Changes to arterial material properties can be an early physiological manifestation of these diseases, and measuring arterial material properties can provide physicians with important information for making clinical decisions and managing patients with arterial diseases. For example, PA stiffness and pulmonary impedance is altered early in the evolution of pulmonary hypertensive vascular disease. In patients with chronic obstructive pulmonary disease (COPD), PH is also an important prognostic indicator. Lesions, such as those in coronary artery disease, also affect arterial material properties. In coronary artery disease, it is important to know where the stenoses are, how many there are, and the extent of the blockages. This information, along with other factors, is used by a cardiologist to decide if the disease should be treated medically, with a stent, or with coronary by-pass surgery.

Current approaches for evaluating the arterial material properties typically include the use of catheters and echocardiography, but with serious technical and practical limitations. For example, in the case of PH, it is conventionally defined based on elevated pulmonary artery (PA) pressure and/or pulmonary vascular resistance (PVR), which is measured conventionally with a right heart catheterization (RHC) procedure. However, PVR measurements only provide incomplete physiologic information in PH because its derivation based on assumptions of uniform pulmonary conduits with static and not pulsatile pressure-volume relationships. In COPD patients, although echocardiography can be used to screen for PH, it has limited accuracy in measuring pulmonary artery (PA) pressure and often hindered by acoustic window limitations in COPD patients. Information on stenosis is traditionally obtained with an angiogram, which uses an invasive catheter to introduce a dye into the artery while it is being imaged with a fluoroscope. However, this procedure only provides information on the geometry of the stenosis and does not evaluate how much blood is flowing through it.

SUMMARY OF THE INVENTION

In light of the issues associated with existing blood-vessel evaluation technologies, the U.S. patent application Ser. No. 15/808,891 provides a method and system for evaluating blood vessel. Briefly, the method provided therein includes: (1) acquiring the time-varying measurements at two spatially separated points of a segment of a blood vessel; (2) calculating a transfer function based on the two sets of measurements; and (3) evaluating the material properties of the blood vessel segment based on the transfer function.

This present disclosure is substantially an expansion and extension of the above identified U.S. patent application Ser. No. 15/808,891, and more specifically discloses an information processing method, device, system, and storage medium implementing the blood vessel evaluation method.

In one aspect, an information processing method is provided, which is to be applied to a processing device and for the evaluation of physiological properties of a segment of a blood vessel in a subject. The information processing method is substantially a computerized method, including the following steps (1-3):

(1) Acquiring measurement data comprising a series of sequences of measurements. Herein the series of sequences of measurements include at least two sequences of measurements, which can be acquired, by means of a measuring device and at different time points in at least one cardiac cycle of the subject, respectively and correspondingly at a series of points along a centerline within the segment of the blood vessel. Each of the series of sequences of measurements contain information about the blood flowing in the blood vessel, based on which the physiological properties of the blood vessel segment of interest can be evaluated. Such information can optionally be blood velocity information, blood pressure information, or another type of information.

(2) Generating a series of profiles from the series of sequences of measurements respectively and correspondingly. Herein each of the series of profiles can be a velocity profile or a pressure profile.

(3) Evaluating physiological properties of at least one selected subsegment within the segment of the blood vessel, each between two of the series of points comprising a first end point and a second end point along a blood flow direction.

Furthermore, this step (3) can include the following sub-steps (a) and (b):

(a) Calculating a transfer function corresponding to each of the at least one selected subsegment. Herein the transfer function is configured to generate an output waveform given an input waveform, using a waveform corresponding to a profile for the first end point and a waveform corresponding to a profile for the second end point as the input waveform and the output waveform respectively.

(b) Determining a physiological property of the blood vessel corresponding to the each of the at least one selected subsegment based on the transfer function.

Optionally, in the information processing method as described above, the transfer function is implemented in a frequency domain, and is calculated as:

$$S_M(f)=M_{output}(f)/M_{input}(f);$$

where f is frequency, $M_{output}(f)$ is the output waveform, and $M_{input}(f)$ is the input waveform.

Optionally, each of the series of sequences of measurements contains blood velocity information. As such, each of the input waveform and the output waveform is a blood velocity waveform, and the transfer function is a velocity transfer function (VTF), calculated as:

$$S_V(f)=V_{output}(f)/V_{input}(f);$$

where $V_{output}(f)$ is the output waveform, and $V_{input}(f)$ is the input waveform.

Optionally, each of the series of sequences of measurements contains blood pressure information, and as such, each of the input waveform and the output waveform is a blood pressure waveform, and the transfer function is a pressure transfer function (PTF), calculated as:

$$S_P(f)=P_{output}(f)/P_{input}(f);$$

where $P_{output}(f)$ is the output waveform, and $P_{input}(f)$ is the input waveform.

In the information processing method, the sub-step (b) of determining a physiological property of the blood vessel corresponding to the each of the at least one selected subsegment based on the transfer function can include the following sub-steps:

(A) Decomposing the input waveform and the output waveform into a series of first harmonic components and a series of second harmonic components respectively. Herein the series of first harmonic components and the series of second harmonic components correspond to one another at each harmonic number.

(B) Forming a series of transfer function harmonics, each obtained by dividing each second harmonic magnitude by a corresponding first harmonic magnitude.

(C) Determining the physiological property of the blood vessel corresponding to the each of the at least one selected subsegment based on one, or a linear combination, of the series of transfer function harmonics.

Optionally, the above sub-step (C) can further include the following sub-steps:

(C1) Calculating an average of a magnitude of each of the series of transfer function harmonics with a harmonic number being 5 or higher, to thereby obtain a mean high frequency magnitude (MHFM) for the transfer function; and (C2) Determining the physiological property of the blood vessel corresponding to the each of the at least one selected subsegment based on the MHFM.

According to some embodiments of the method, sub-step (C1) includes obtaining the MHFM by calculating an average of a magnitude of each of the series of transfer function harmonics with harmonic numbers 5 through 8. It should be mentioned that other combinations of the harmonic numbers are possible, such as harmonic numbers 6-10, or 9-12, etc.

According to some embodiments, the information processing method can be used for the evaluation of a pulmonary artery, and as such, the segment of the blood vessel can be at least one of: (1) a segment between a main pulmonary artery (MPA) and a right pulmonary artery (RPA) proximal to a bifurcation; (2) a segment between the MPA and a left pulmonary artery (LPA) proximal to the bifurcation; (3) a segment between the RPA proximal and distal to the bifurcation; or (4) a segment between the LPA proximal and distal to the bifurcation. As used herein and throughout the disclosure, the term "bifurcation" is referred to as a location of the pulmonary artery where the main pulmonary artery bifurcates or branches into the right and left pulmonary arteries.

Herein, depending on the disease of interest, the specific segment(s) of the pulmonary artery for the transfer function-based information processing method can vary. For example, since pulmonary hypertension (PH) typically affects the lungs equally, only the measurement and VTF evaluation on the proximal RPA to distal RPA segment (i.e. the segment between the RPA proximal and distal to the bifurcation) shall be enough. On the other hand, however, chronic obstructive pulmonary disease (COPD) can affect the two lungs differently, thus the measurement and VTF evaluation on all of the above four segments may need to be performed.

Further optionally, the information processing method as described above can further include a sub-step of determining that the subject has a disease of interest if the subject has MHFM at least 20% higher than a matched population of subjects absent of the disease of interest, wherein the disease of interest is PH or COPD.

It is noted that the disease of interest that can be evaluated by the information processing method disclosed herein is not limited to PH or COPD only, and can substantially include any blood vessel diseases or vascular diseases which implicate blood flow/velocity/pressure change (e.g. occlusions, blockages, leakages, stiffness, hardening, narrowing, etc. of blood vessel) for a particular segment of blood vessel (e.g. arteries, veins, capillaries, etc.) due to any pathological or non-pathological causes (e.g. buildup of fats and/or cholesterols, blood clots, abnormal bulge, or abnormal cellular growth in the blood vessel walls, etc.). As such, the disease of interest can, in addition to pulmonary arterial diseases, also include coronary arterial diseases, peripheral arterial diseases (e.g. intestinal ischemic syndrome, renal artery disease, carotid artery disease, etc.), and peripheral venous diseases (e.g. deep vein thrombosis (DVT), varicose veins, etc.).

Herein, the term "matched population of subjects" are referred to as a reference population compared with which, the subject can be evaluated the disease of interest. This reference population is considered to be "matched" with the subject if they are in at least one of a substantially same age group (e.g. 50-60, or 60-70, etc.), a substantially same ethnicity group (e.g. Caucasian, African American, etc.), a substantially same sex group (male or female), a substantially same family history group (i.e. with or without), a substantially same study group (e.g. smoking or not smoking, etc.) as the subject.

In the information processing method, each of the series of sequences of measurements can be optionally acquired in synchronization to the subject's electrocardiogram signal and at equally spaced time points in the at least one cardiac cycle. Furthermore, each of the at least one cardiac cycle can optionally include a total of at least 20 time points.

According to some embodiments of the information processing method, each of the series of sequences of measurements contains blood velocity information, and as such, the measuring device can be a magnetic resonance imaging (MRI) device, a Doppler ultrasound device, or a catheter.

Herein optionally, the measuring device includes a magnetic resonance imaging (MRI) scanner, and each of the series of sequences of measurements is acquired through phase contrast MRI imaging.

According to some embodiments of the information processing method, at least two of the series of sequences of measurements can be acquired through separate 2D phase contrast MRI scans, and each scan can be performed with a prescribed phase contrast imaging plane.

According to some embodiments of the information processing method, each of the series of sequences of measurements can be acquired without prescribing any phase contrast imaging plane when performing the phase contrast MRI imaging.

Furthermore, according to some embodiments, at least one, and preferably all, of the series of sequences of measurements can be acquired through one single free-breathing 4D flow MRI scan. Herein "free-breathing" means that the subject does not need to hold his/her breath.

Optionally, a number of the at least one selected subsegment is at least 2.

According to some embodiments of the information processing method, each of the series of sequences of measurements contains blood pressure information, and as such, the measuring device can be a catheter, a tonometric device, or a fitness wristband capable of measuring blood pressure.

In another aspect, the present disclosure further provides a processing device for evaluating physiological properties of a segment of a blood vessel in a subject, which is configured to substantially implement various embodiments of the information processing method as described above, and includes a data acquisition module, a profile generating module, and an evaluation module.

The data acquisition module is configured to acquire measurement data of the segment of the blood vessel. The measurement data comprises a series of sequences of measurements, the series of sequences of measurements comprises at least two sequences of measurements, and are acquired, by means of a measuring device and at different time points in at least one cardiac cycle of the subject, respectively at a series of points along a centerline within the segment of the blood vessel. Each of the series of sequences of measurements contains blood velocity information or blood pressure information. The profile generating module is configured to generate a series of profiles from the series of sequences of measurements respectively, and each of the series of profiles is a velocity profile or a pressure profile. The evaluation module is configured to evaluate physiological properties of at least one selected subsegment within the segment of the blood vessel, each between two of the series of points comprising a first end point and a second end point along a blood flow direction. Specifically, the evaluation module includes a calculation sub-module and a determination sub-module. The calculation sub-module is configured to calculate a transfer function corresponding to each of the at least one selected subsegment. Herein the transfer function is configured to generate an output waveform given an input waveform, using a waveform corresponding to a profile for the first end point and a waveform corresponding to a profile for the second end point as the input waveform and the output waveform respectively. The determination sub-module is configured to determine a physiological property of the blood vessel corresponding to the each of the at least one selected subsegment based on the transfer function.

In yet another aspect, the present disclosure further provides a system for evaluating physiological properties of a segment of a blood vessel in a subject. In addition to the processing device as described above, the system further includes a measuring device configured to acquire, at different time points in one cardiac cycle of the subject, the series of sequences of measurements at the series of points along a centerline within the segment of the blood vessel respectively.

According to some embodiments of the system, the measuring device is a magnetic resonance imaging (MRI) device, a Doppler ultrasound device, or a catheter, and correspondingly each sequence of measurements contains blood velocity information.

According to some other embodiments of the system, the measuring device is a catheter, a tonometric device, or a fitness wristband capable of measuring blood pressure, and correspondingly each sequence of measurements contains blood pressure information.

In yet another aspect, the present disclosure further provides a non-transitory computer storage medium storing computer-executable instructions which, when executed by a processor, cause the processor to execute the information processing method according to any of the embodiments as described above.

The term "2D MRI", "two-dimensional MRI", or alike, as used throughout the disclosure, is referred to as an MRI scanning technique that typically takes a single slice along a prescribed MRI imaging plane, in which magnetic gradients are applied in only two directions to figure out the location of frequencies, thus enabling through-plane assessment of blood flow fields and velocities. The term "4D MRI", "four-dimensional MRI", or alike, as used throughout the disclosure, is referred to as an improved MRI technique that can provide complete information about temporal and spatial coverage of the area in question and a detailed visualization of the direction of blood flow, etc., and can also be considered to be exchangeable with "3D plus time" MRI (Markl M. et al. 2012) or alike.

Throughout the disclosure, the mean high frequency magnitude (MHFM) is defined as an average of harmonics 5 or above based on the transfer function, and an "elevated MHFM" is defined if the MHFM from the subject under investigation is at least 20% higher, and preferably at least 50% higher, than a mean value of MHFM from a population of subjects absent of the disease of interest (such as PH, or COPD). The term "mean high frequency magnitude" is considered to be exchangeable with "mean high frequency modulus".

BRIEF DESCRIPTION OF THE DRAWINGS

FIGS. 2A and 2B show respectively a magnitude image and a velocity image from phase contrast magnetic resonance imaging (PC-MRI) of a slice perpendicular to the right pulmonary artery proximal to the bifurcation, where 001 delineates the right pulmonary artery, and 002 delineates the right pulmonary artery, and the value of each pixel is the velocity of the corresponding tissue in the direction perpendicular to the slice;

FIG. 3 illustrates mean velocity-time profiles in main (003) and right (004) pulmonary arteries (PA) obtained using phase contrast magnetic resonance imaging (PC-MRI);

FIG. 7 illustrates the calculation of a pressure transfer function (PTF) from a proximal and distal pressure waveform, where each distal harmonic magnitude is divided by the corresponding proximal harmonic magnitude to form the corresponding PTF harmonic, Harmonic 0 corresponds to the FFR, higher order harmonics describe changes to the shape of the waveform as it passes through the section of artery, and 014 denotes a dicrotic notch;

FIGS. 24A-24D show scatter plots showing intra- (FIG. 24A, FIG. 24B) and inter- (FIG. 24C, FIG. 24D) observer correlation (FIG. 24A, FIG. 24C) and agreement (FIG. 24B, FIG. 24D) for individual harmonics of velocity transfer function.

FIGS. 25A and 25B show fit plots of right ventricular mass index (RVESMI) and VTF mean high frequency magnitude (MHFM) without (FIG. 25A) and with (FIG. 25B) outliers removed. 028 and 029 are the 2 'outliers.' The solid lines (064, 067) denote the best fit line. The shaded regions (065, 068) denote the 95% confidence limits. The dashed lines (066, 069) denote the 95% prediction limits;

FIGS. 31A and 31B show invasive impedance curves (FIG. 31A) and corresponding velocity transfer function curves (FIG. 31B) over first six harmonics in patients with normal (040, 042) or elevated (041, 043) pulmonary vascular resistance. Error bars denote ±1 standard error;

FIG. 33 shows the velocity transfer function curve over first six harmonics of a patient with idiopathic pulmonary fibrosis with otherwise no clinical pulmonary hypertension (mean PA pressure of 19 mm Hg), PCWP 5 mm Hg, CO 5.54 L/min, PVR 2.525 WU (early PA remodeling);

FIG. 34 shows the velocity transfer function curve over first six harmonics of a patient with idiopathic pulmonary fibrosis with otherwise no clinical pulmonary hypertension (mean PA pressure of 22 mm Hg), PCWP 6 mm Hg, CO 5.41 L/min, PVR 2.96 WU (early PA remodeling);

FIG. 35 shows the velocity transfer function curve over first six harmonics of a patient with chronic left ventricular ischemic cardiomyopathy from an old left anterior descending artery dissection with otherwise no clinical pulmonary hypertension (mean PA pressure of 18 mm Hg), PCWP 11 mm Hg, CO 3.99 L/min, PVR 1.75 WU (normal);

FIG. 41A shows representative MAG and PC images from the proximal (solid-line contour) and distal (dotted-line contour) portions of the RPA; FIG. 41B shows representative mean velocity profiles over the cardiac cycle measured in the proximal and distal portions of the RPA; and FIG. 41C shows representative examples of Fourier transform magnitudes and VTF in subjects with high (>1) and low (<1) MHFM (average modulus for harmonics 5-7), and the abbreviations used herein include: MHFM: mean high frequency modulus, VTF: velocity transfer function, MAG: magnitude, PC: phase-contrast, and RPA: right pulmonary artery.

DETAILED DESCRIPTION OF THE INVENTION

This present disclosure is substantially an expansion and an extension of the U.S. patent application Ser. No. 15/808, 891, the disclosure of which is incorporated by reference in its entirety.

Figure 1A:
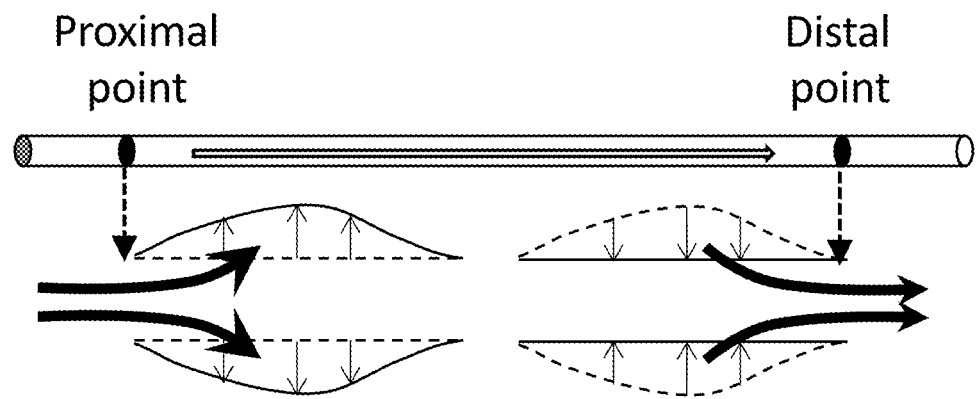
FIGS. 1A and 1B illustrate the basic working principle of a blood vessel evaluation method provided by some embodiments of the present disclosure, where flow into a pulmonary artery (PA) causes distension of the vessel wall which then recoils to the original state, resulting in pulsatile component of the flow impedance (FIG. 1A), and a calculation of a transfer function that provides mathematical relationship between the input and out waveforms (FIG. 1B) and therefore provides a measure of viscoelastic properties of the vessel wall.
Figure 1B:
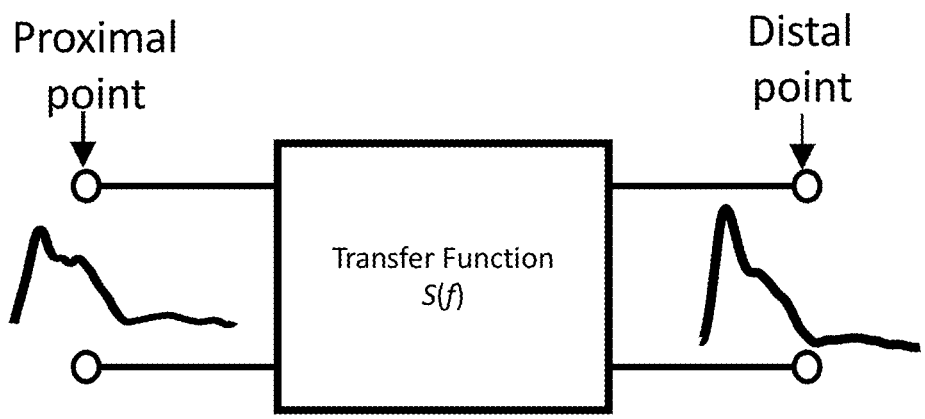

A method and a system for determining physiological properties of a blood vessel in a subject from measurements at two spatially separated points on a blood vessel segment of interest is disclosed. In a manner distinguishing from most, if not all, existing approaches, the method considers a pulsatile nature of blood flow along the direction thereof, and briefly includes the following steps: (1) acquiring time-varying measurements at two points of the blood vessel (i.e. a proximal point and a distal point along a blood flow direction, as illustrated in FIG. 1A) respectively; (2) calculating a transfer function (i.e. S(f) in FIG. 1B) configured to produce an output waveform given an input waveform, using a waveform corresponding to the set of measurements at the proximal point as the input waveform, and using a waveform corresponding to the set of measurements at the distal point as the output waveform; and (3) evaluating the material properties of the blood vessel segment based on the calculated transfer function.

The measurements can include, but are not limited to, measurements of blood pressure, blood flow, and blood velocity. Measurements of blood velocity or blood flow can be obtained from phase-contrast magnetic resonance imaging, Doppler ultrasound, an invasive catheter. Measurements of blood pressure can be obtained from an invasive catheter, or other pertinent vital sign measuring devices including, but not limited to, a tonometric device, a fitness wristband, or a blood pressure measurement device of another type. The transfer function can be linear or non-linear, time-invariant or time-varying. The transfer function can operate in a time domain or a frequency domain. The method can be applied to both an artery or a vein. The subject can be an animal or a human. The parameters of the calculated transfer function are related to the physiological properties of the blood vessel.

Figure 1C:
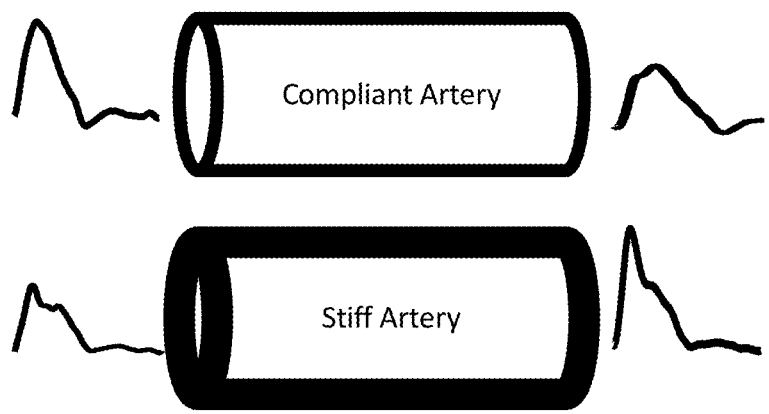
FIG. 1C illustrates a comparison between a compliant PA and a stiff PA, where the input velocity wave form changes in shape in a predictable fashion due to the viscoelastic properties of the vessel wall and geometry of the vessel.
Figure 4A:
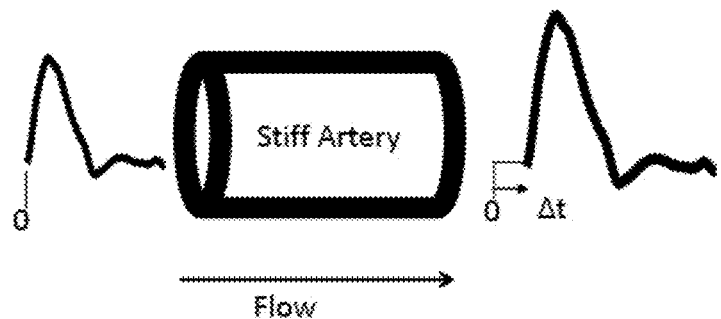
FIGS. 4A-4D illustrate that, in a stiff artery, the output waveform is a scaled and shifted version of the input waveform (FIG. 4A), whereas in a compliant artery, the output waveform has a more complex relationship with the input waveform (FIG. 4C), and these relationships are respectively reflected in the corresponding transfer functions (|H(f)|) for the stiff artery (FIG. 4B) and the compliant artery (FIG. 4D)
Figure 4B:
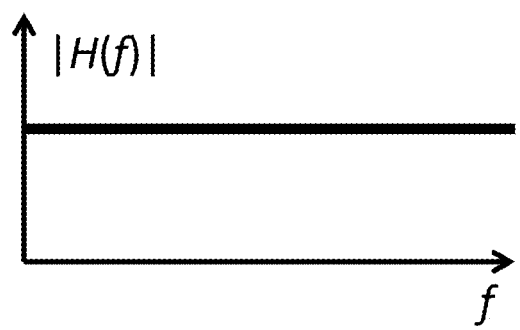
Figure 4C:
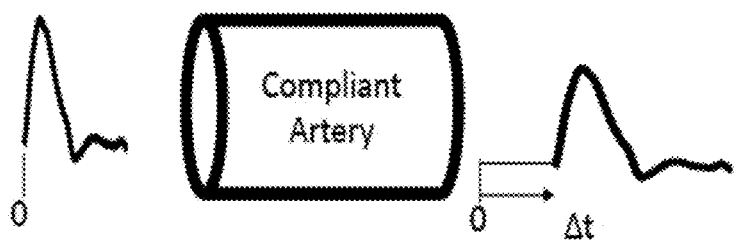
Figure 4D:
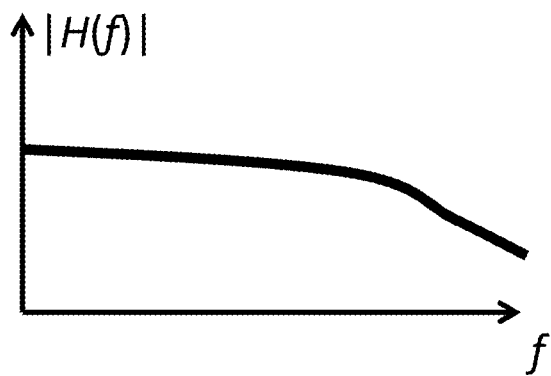

By evaluating the physiological properties of a blood vessel, the method can be used for detecting and/or evaluating a blood vessel disease such as pulmonary hypertension (PH), chronic obstructive pulmonary disease (COPD), heart failure with preserved ejection fraction, heart failure with reduced ejection fraction, connective tissue disorders, coronary artery disease, or any other disease affecting the physiological properties of blood vessels. For example, a comparison between a compliant PA and a stiff PA (such as in the disease of pulmonary hypertension, or PH) is illustrated in FIG. 1C, where the input velocity wave form changes in shape in a predictable fashion due to the viscoelastic properties of the vessel wall and geometry of the vessel.

According to some embodiments of the method, the measurements include blood velocity measurements at the proximal and distal points on the blood vessel segment of interest, and the transfer function is a velocity transfer function (VTF) calculated based on the blood velocity waveforms for the proximal and distal points.

Optionally, the blood velocity is measured non-invasively with phase-contrast cardiac magnetic resonance imaging (PC-MRI) at two points in the pulmonary artery (PA) tree. PC-MRI is a technique where a slice through the body at an arbitrary orientation is prescribed and an image is produced of the velocities in a particular direction of tissues moving through the slice. In PC-MRI, two images are produced of each slice: a magnitude image (FIG. 2A) and a phase image (FIG. 2B). The magnitude image is an anatomical image similar to standard MRI images. In the phase image (FIG. 2B), each pixel represents a small cube of tissue, and the grayscale value of a pixel has a known linear relationship to the tissue's velocity in a particular direction. Velocities can be positive or negative. In PC-MRI, stationary tissues (velocity=0) are usually 50% gray. Tissues moving in one direction are bright, and tissues moving in the opposite direction are dark. The acquisition is synchronized to the subject's electrocardiogram signal and a sequence of images are obtained at equally spaced time points in the cardiac cycle. Typically, 20-32 time points are acquired. In this embodiment, two such image sequences are obtained: one proximal to the right PA (RPA) bifurcation and one distal to the bifurcation. Measurements could also be obtained from the left PA (LPA) proximal and distal to the bifurcation. The slices are prescribed perpendicular to the artery at each point, and velocity perpendicular to the slice is measured. As shown in FIG. 2B, the resulting images contain the blood velocity field in a cross section of the artery. A user defines the boundary of the artery with the aid of a computer in each image of the sequence. Statistics of the velocity field in the artery at each time point are computed to produce a velocity versus time curve over the cardiac cycle as shown in FIG. 3.

FIGS. 4A-4D illustrate the pulsatile velocity versus time curves measured in a right PA (RPA) at a point proximal to the bifurcation and a point distal to the bifurcation in a normal human volunteer and a patient with pulmonary hypertension (PH). In a normal volunteer, with a compliant PA, the velocity profile not only is shifted in the transit time between the two sites, but there are also complex shape changes across the entire wave. In a patient with PH, the PA is stiffer and both the time shift and shape change are reduced. These time shifts and shape changes are related to the compliance and geometry of the artery between the two points.

These changes can be compactly described by a transfer function between the two velocity profiles measured non-invasively with phase-contrast MRI. A transfer function is a linear or non-linear operator that generates an output waveform given an input waveform. In this embodiment, the transfer function, $s_V[\ ]$, is related to the input waveform, $V_{proximal}(t)$, and the output waveform, $v_{distal}(t)$, as follows:

$$v_{distal}(t)=s_V[v_{proximal}(t)]$$

In some embodiments, the transfer function is modeled as a linear, time-invariant system. In this case, the transfer function convolves the input with an impulse response function, $S_V(t)$:

$$v_{distal}(t)=s_V(t)*v_{proximal}(t),$$

where * denotes the convolution operator. Taking the Fourier transform of both sides yields $$V_{distal}(f)=S_V(f)V_{proximal}(f)$$

where f is frequency in Hertz, and $S_V(f)$ is the transfer function. $S_V(f)$ is a complex-valued function and is often displayed as plots of the magnitude of $S_V(f)$ versus frequency and the phase of $S_V(f)$ versus frequency. In this embodiment, the velocity transfer function (VTF) can be computed from the measured input and output waveforms as follows:

$$S_V(f) = \frac{V_{distal}(f)}{V_{proximal}(f)}.$$

The transfer function above is a complex-valued function of continuous frequency. However, the transfer function is displayed as complex magnitude versus harmonic frequency. A harmonic frequency is an integer multiple of the cardiac frequency, which is equal to the reciprocal of the cardiac period. Expressing the transfer function in harmonics allows comparisons between subjects or in the same subject over time to be made independent of the individual heart rates.

In some embodiments, the transfer function is implemented in the time domain as an autoregressive moving average (ARMA) model:

$$Y_k = X_k + \sum_{i=1}^{p} b_i Y_{k-i} + \sum_{i=1}^{q} a_i X_{k-i}$$

where $X_k$ are samples of the input signal and $Y_k$ are samples of the output signal. p is number of moving average terms and q is the number of autoregressive terms. The $a_i$ and $b_i$ are coefficients. The parameters p, q, $a_i$, and $b_i$ are computed based on the measured input and output signals, and a function of these parameters is related to the material properties of the vessel.

Transfer functions like the VTF are one-way operators. They produce the output given the input but not necessarily the input given the output. In arteries, part of the blood pressure wave reflects off of the capillary bed and travels upstream through the artery. Sometimes this can be seen as the so-called dicrotic notch in velocity or pressure waveforms (for example, see 010 in FIG. 6). To investigate the effects of reflected waves on the VTF, simulations were performed of a velocity profile traveling through a section of PA with no change in shape or amplitude and a transit time of 25 ms. VTFs were computed from the input and output velocity profiles for the ideal case when no reflected wave was present and for the more realistic case when a reflected wave with an amplitude 10% of the primary wave and delayed by 500 ms was present. The reflected wave results in a ripple effect that averages out when parameters are computed over a range of harmonics.

Impedance is a specific case of a transfer function when the two functions are voltage and current or pressure and flow measured at the same point in the artery:

$$\text{Impedance }(f) = \frac{\text{Pressure }(f)}{\text{Flow }(f)}.$$

The VTF is like impedance because it describes predominantly the influence of vessel geometry and compliance/stiffness to cause frequency-dependent changes in the input velocity profile as it travels through the artery thereby producing the output velocity profile. Optionally, a single harmonic magnitude in the VTF or a linear combination of harmonic magnitudes are calculated and used as a surrogate measure of arterial compliance.

Figure 5A:
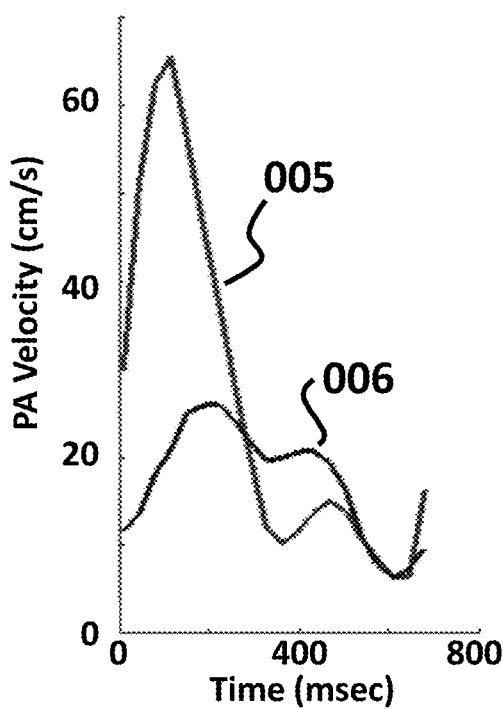
FIGS. 5A-5D show representative right PA velocity curves (FIG. 5A and FIG. 5C) and corresponding VTF (FIG. 5B and FIG. 5D) from a patient with PVR≤2.5 Woods Units (WU) (FIG. 5A and FIG. 5B) and a patient with PVR>2.5 WU (FIG. 5C and FIG. 5D)
Figure 5B:
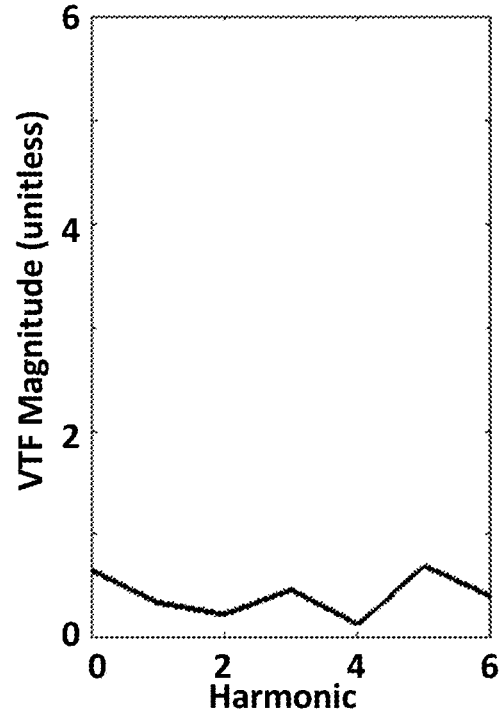
Figure 5C:
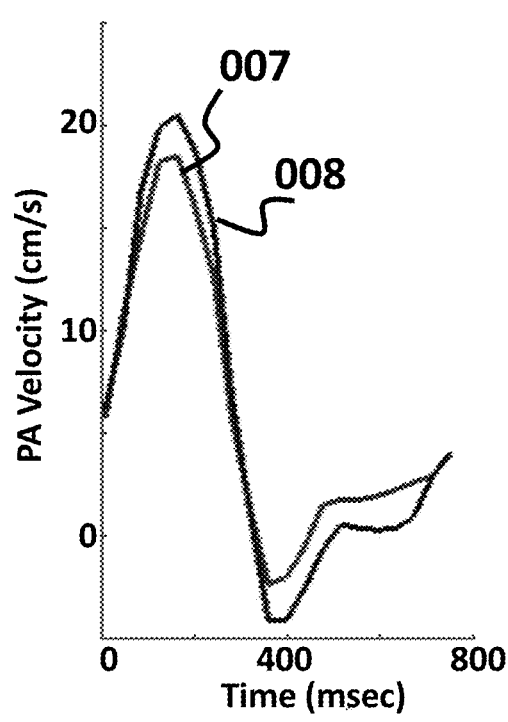
Figure 5D:
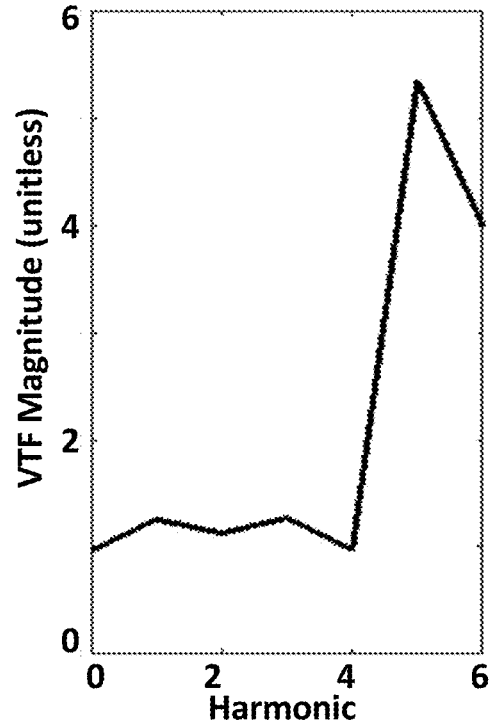

FIGS. 5A-5D further show representative right PA velocity curves (FIG. 5A and FIG. 5C) and corresponding VTF (FIG. 5B and FIG. 5D) from a first patient (i.e. without PH) with PVR≤2.5 WU (FIG. 5A and FIG. 5B) and a second patient (i.e. with PH) with PVR>2.5 WU (FIG. 5C and FIG. 5D). In the figures, 005 and 006 respectively denote the proximal velocity waveform and the distal velocity waveform in FIG. 5A, and 007 and 008 respectively denotes the proximal velocity waveform and the distal velocity waveform in FIG. 5C. As can be seen, the proximal velocity waveforms are similar between the two patients, but the distal velocity waveforms are quite different. If converted into VTF magnitude, the second patient (i.e. PH patient) shows elevated VTF magnitude values for harmonic 5 and above compared with the first patient.

According to some other embodiments of the method, the measurements include blood pressure measurements at the proximal and distal points on the blood vessel segment of interest, and the transfer function is a pressure transfer function (PTF) calculated based on the blood pressure waveforms for the proximal and distal points.

Optionally, blood pressure waveform, with pressure as the y-axis and time as the x-axis, is measured directly with an invasive catheter at two points in the arterial tree. The time-varying blood pressure waveform at the upstream (proximal) point is considered the input and the blood pressure waveform at the downstream (distal) point is considered the output.

In one embodiment illustrated in FIGS. 5 and 6, the pressure transfer function (PTF) $S_P(f)$ is computed between the two measured pressure profiles by taking the Fourier transform of each pressure profile and dividing one by other as follows:

$$S_P(f) = \frac{P_{distal}(f)}{P_{proximal}(f)}$$

Figure 6:
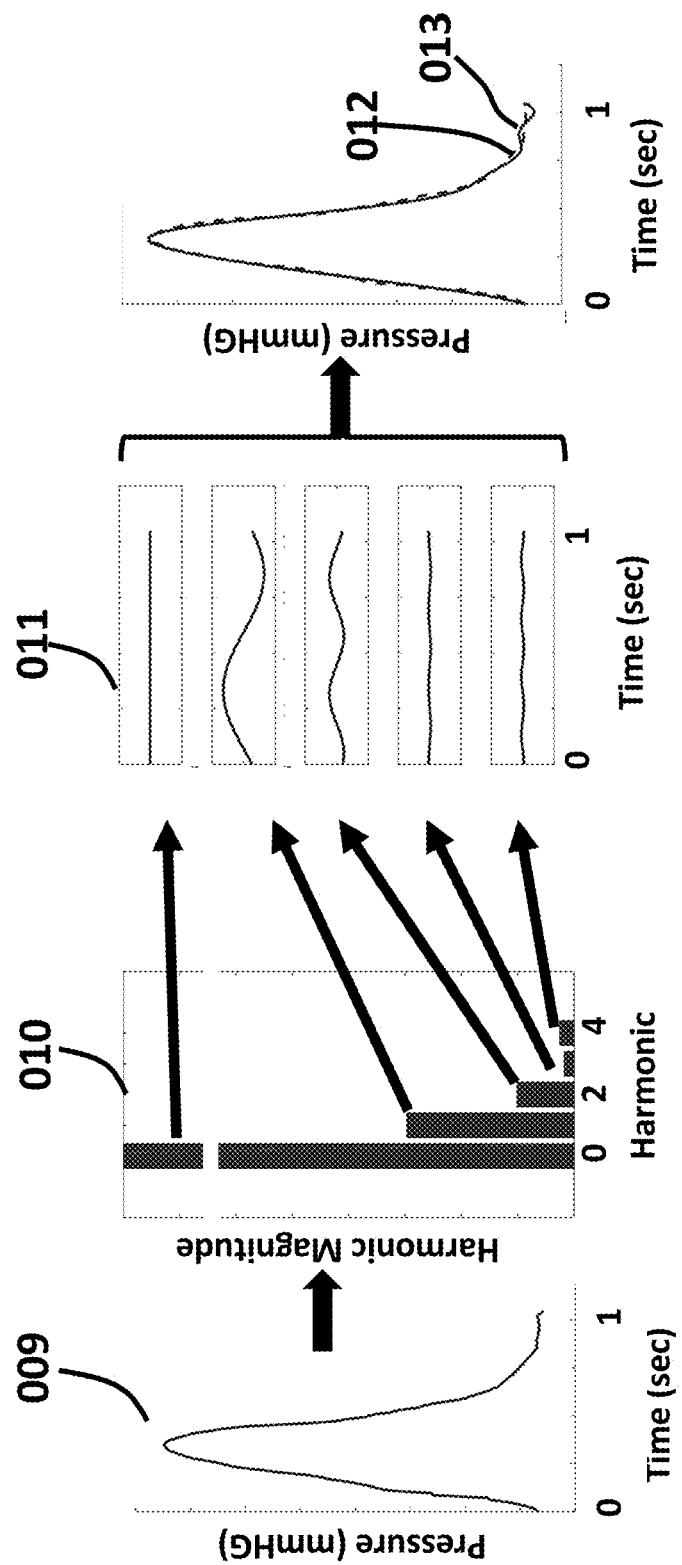
FIG. 6 shows the decomposition of a pressure waveform (009) into harmonic components, where the first 5 harmonic magnitudes are shown in 010, the first 5 harmonic component waveforms are shown in 011, the overlaying of the actual waveform (012, dashed line) on a waveform calculated from the first 5 harmonics (013, solid line) is also shown, where Harmonic 0 is the mean pressure, and higher order harmonics describe subtle changes in the waveform.

FIG. 6 shows the decomposition of a pressure waveform (004) into harmonic components, where the first 5 harmonic magnitudes are shown in 005, the first 5 harmonic component waveforms are shown in 006, the overlaying of the actual waveform (008, dashed line) on a waveform calculated from the first 5 harmonics (009, solid line) are shown 007. Harmonic 0 is the mean pressure. Higher order harmonics describe subtle changes in the waveform. FIG. 7 shows the calculation of PTF from a proximal and distal pressure waveform. Each distal harmonic magnitude is divided by corresponding proximal harmonic magnitude to form the corresponding PTF harmonic. Harmonic 0 corresponds to a fractional flow reserve (FFR). Higher order harmonics describe changes to the shape of the waveform as it passes through the section of artery.

Optionally, a single harmonic magnitude in the PTF or a linear combination of harmonic magnitudes are calculated and used as a surrogate measure of arterial compliance.

In some embodiments, a single heartbeat pressure waveform is measured with an invasive catheter at a point distal to a suspected stenosis in a coronary artery and considered to be a reference waveform. The catheter is then pulled back through the area of suspected stenosis yielding a series of single heartbeat waveforms. A series of PTFs $S_{P_i}(f)$ are then computed by computing:

$$S_{P_i}(f) = \frac{P_{distal_i}(f)}{P_{proximal}(f)}$$

In this embodiment, the entire series of pressure waveform is analyzed to obtain a comprehensive analysis of the pressure waves that reflects the fundamental interaction of moving blood in the coronary artery, and the vessel wall, coronary branches and stenosis. This embodiment not only allows evaluation of parameters analogous to FFR, but also parameters related to arterial material parameters.

In some other embodiments, a single harmonic magnitude in the PTF or a linear combination of harmonic magnitudes are calculated. Changes in the harmonics or linear combination of harmonics are used to determine the location and severity of the stenosis.

On the basis of the method described above, this present disclosure further provides a computerized information processing method, a processing device implementing the above blood vessel evaluation method, a system comprising the processing device, and a storage medium.

In a first aspect, an information processing system for evaluating physiological properties of a segment of a blood vessel in a subject is provided.

Figure 8:
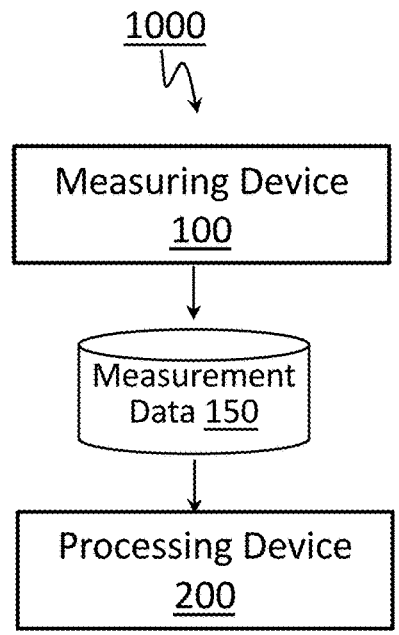
FIG. 8 shows a block diagram of an information processing system according to certain embodiments of the disclosure.

FIG. 8 shows a block diagram of an information processing system according to certain embodiments of the disclosure. As illustrated in FIG. 8, the information processing system 1000 includes a measuring device 100 and a processing device 200.

The measuring device 100 is configured to perform a measurement on the subject, and more specifically on the segment of the blood vessel of the subject, to thereby collect or obtain measurement data 150 that contain information of the physiological properties of the segment of the blood vessel in the subject. The processing device 200 is configured to acquire the measurement data 150 that has been collected by the measuring device 100, and then to perform an information processing over the acquired measurement data 150, by means of a computerized information processing method that is applied to the processing device 200, so as to determine the physiological properties of the segment of the blood vessel in the subject.

According to some embodiments of the information processing system 1000, the measuring device 100 can be a blood velocity/flow-detecting device, such as a magnetic resonance imaging (MRI) scanner, a Doppler ultrasound device, or an invasive catheter capable of detecting blood velocity or blood flow, and correspondingly the measurement data 150 collected thereby contains blood velocity information or blood flow information.

According to some other embodiments, the measuring device 100 can be a blood pressure-monitoring device, such as an invasive catheter, a tonometric device, or a fitness wristband capable of measuring blood pressure, and correspondingly the measurement data 150 collected thereby contains blood pressure information.

It is noted that the various types of the measuring devices 100 as listed above shall be considered for the purpose of illustration only, and thus they shall represent only non-limiting examples. It is possible that the measuring device 100 can be of other types that are capable of collecting, in the measurement data 150, information other than the blood velocity/flow/pressure information, based on which the physiological properties of the segment of the blood vessel in the subject can be evaluated.

More specifically, in the information processing system disclosed herein, the measurement data 150 collected by the measuring device 100 comprises a series of sequences of measurements, which respectively correspond to the measurements at a series of points (m>1) along a centerline within the segment of the blood vessel. Additionally, for each individual point of interest on the centerline within the segment of the blood vessel, the corresponding sequence of measurements include a plurality of measurements (n>1), corresponding to different time points in at least one cardiac cycle of the subject. Herein each of the series of sequences of measurements can contain information such as blood velocity information, blood pressure information, or another type of information, depending on which type of the measuring device 100 is to be used. More details will be provided below.

Figure 9:
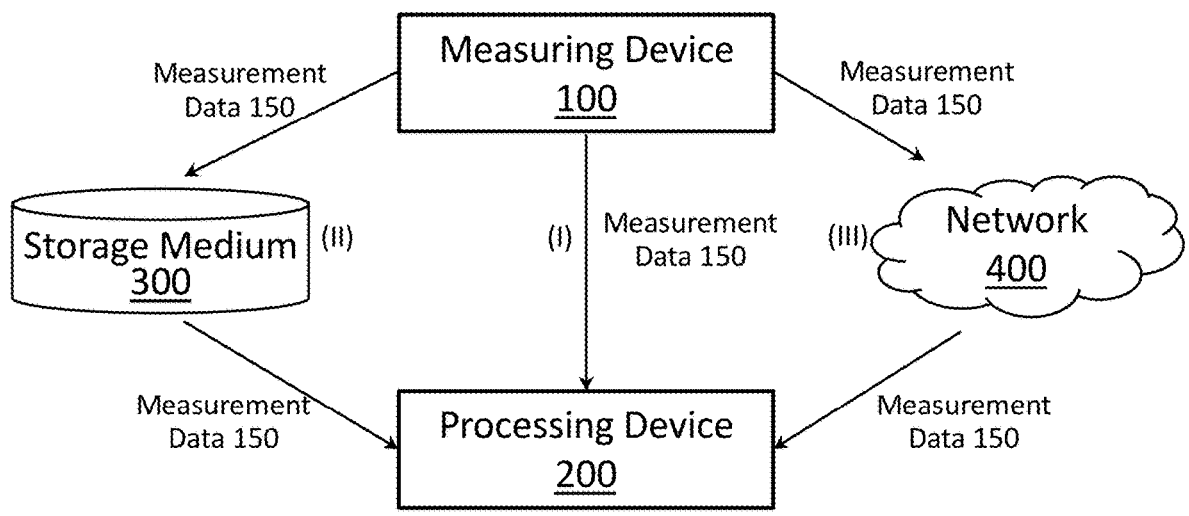
FIG. 9 illustrates a variety of ways for communicating the measurement data from the measuring device to the processing device in the information processing system shown in FIG. 8.

In the information processing system 1000, there can be a variety of ways for communicating the measurement data 150 from the measuring device 100 to the processing device 200, as shown in FIG. 9.

Figure 10A:
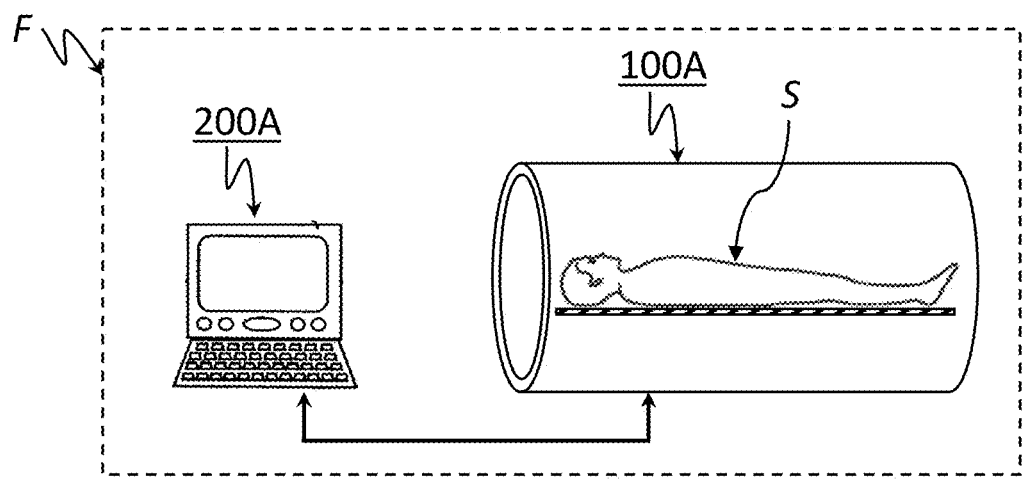
FIGS. 10A and 10B illustrate two different manners whereby the measuring device is directly connected to the processing device communicatively.
Figure 10B:
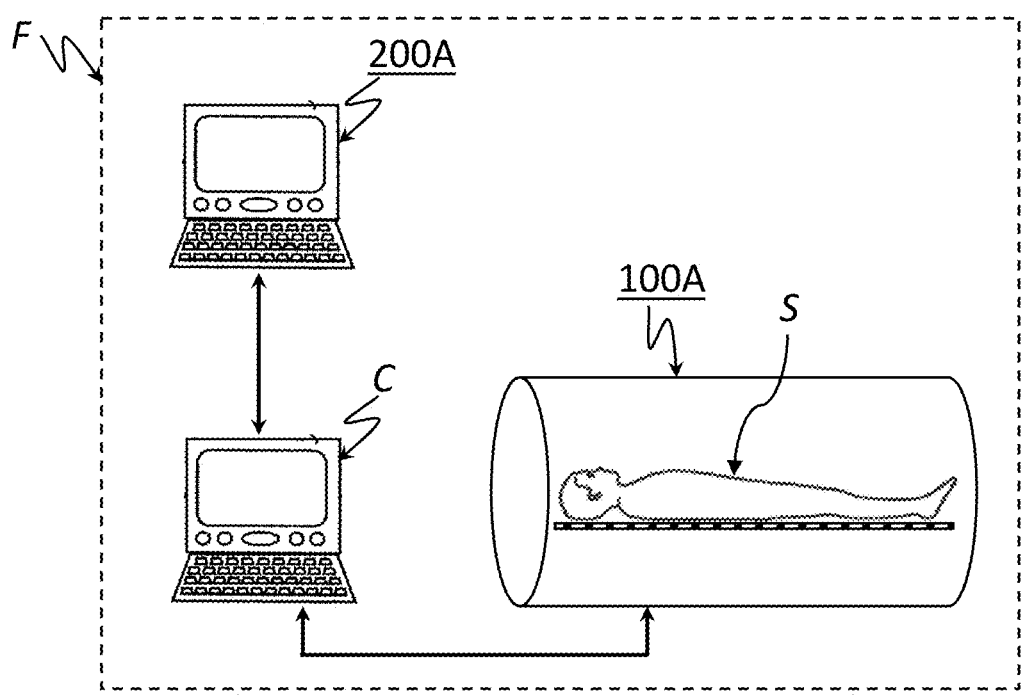

Optionally in a first manner (i.e. manner (I) in FIG. 9), the measuring device 100 can be communicatively connected to the processing device 200 directly, and as such, the measurement data 150 collected by the measuring device 100 can be directly transferred or communicated from the measuring device 100 to the processing device 200. In a more specific example illustrated in FIG. 10A where the measuring device 100 is an MRI scanner 100A and the processing device 200 is a computer 200A, the MRI scanner 100A and the computer 200A can be arranged at a same local facility F (e.g. a hospital, or a diagnosis center), and are directly connected communicatively by wiring (illustrated by the double arrows). As such, in this specific embodiment, the computer 200A is communicatively connected to the MRI scanner 100A in a local and direct manner. The computer 200A can be configured to both control the operation of the MRI scanner 100A for collecting and storing the measurement data over a blood vessel segment of interest in a subject S, and then to perform data processing of the measurement data 150 so as to evaluate the physiological properties of the blood vessel segment in the subject S. In an alternative manner illustrated in FIG. 10B, a control computer C other than the computer 200A can be dedicated to controlling the operation of the MRI scanner 100A to collect and store the measurement data over the blood vessel segment of interest in the subject S, whereas the computer 200A (i.e. the processing device 200) is communicatively connected to the control computer C, and is dedicated, upon retrieving the measurement data stored in the control computer C, to performing the data processing of the measurement data for the evaluation of physiological properties of the blood vessel segment of the subject S.

Alternatively in a second manner, as illustrated by manner (II) in FIG. 9, the measurement data 150 collected by the measuring device 100 is first stored in a machine-readable and non-volatile storage medium 300, such as a portable hard disk (i.e. HDD), a flash drive, a solid-state disk (i.e. SSD), an optical disc (e.g. CD or DVD), or a magnetic tape, etc., by means of a storage control device (not shown) connected to the measuring device 100. Then the processing device 200 can read the storage medium 300 to thereby acquire the measurement data 150 for the evaluation of physiological properties of the blood vessel segment of the subject.

Further alternatively in a third manner, as illustrated by manner (III) in FIG. 9, the measuring device 100 can be communicatively connected to the processing device 200 via a network 400, such as an internet or an intranet, and the measurement data 150 collected by the measuring device 100 is correspondingly communicated to the processing device 200 via the network 400.

Figure 11A:
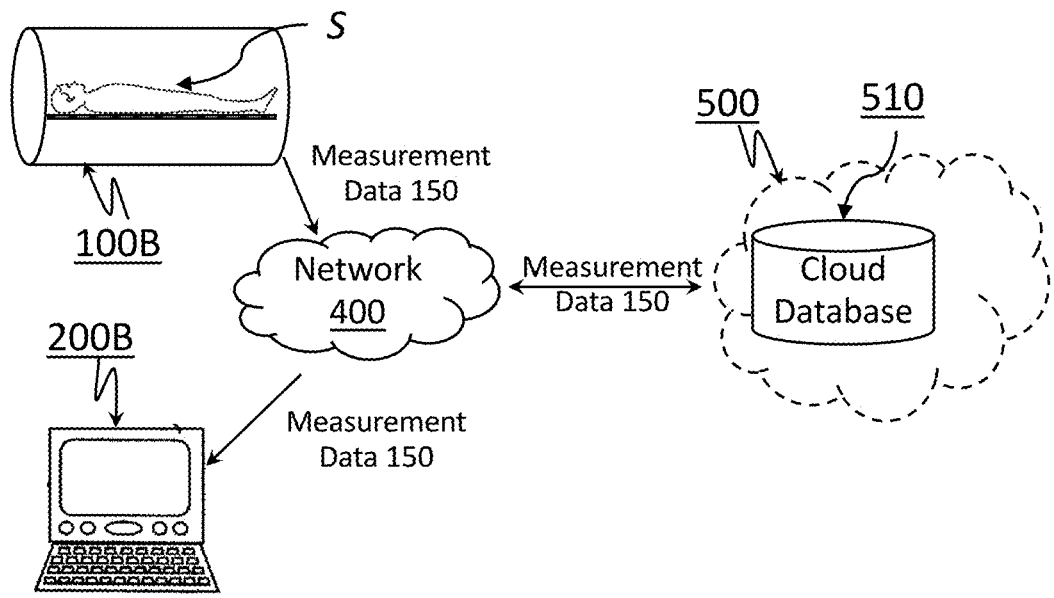
FIGS. 11A-11C illustrate three different manners whereby the measuring device is communicatively connected to the processing device via a network.

As further illustrated in FIG. 11A, optionally for this above third manner, a cloud 500 can be communicatively connected to the network 400, and the cloud 500 is provided with a cloud database 510 configured to store data acquired from the network 400. Through the network 400, the measurement data 150 collected by the measuring device (e.g. an MRI scanner 100B in FIG. 11A) can be first communicated to the cloud 500 and stored in the cloud database 510. Then also through the network 400, a processing device 200 (e.g. a computer 200B in FIG. 11A) arranged at a facility other than the facility accommodating the MRI scanner 100B can further communicate with the cloud 500 to thereby retrieve the measurement data 150 stored in the cloud database 510 for the evaluation of physiological properties of the blood vessel segment of the subject S.

Figure 11B:
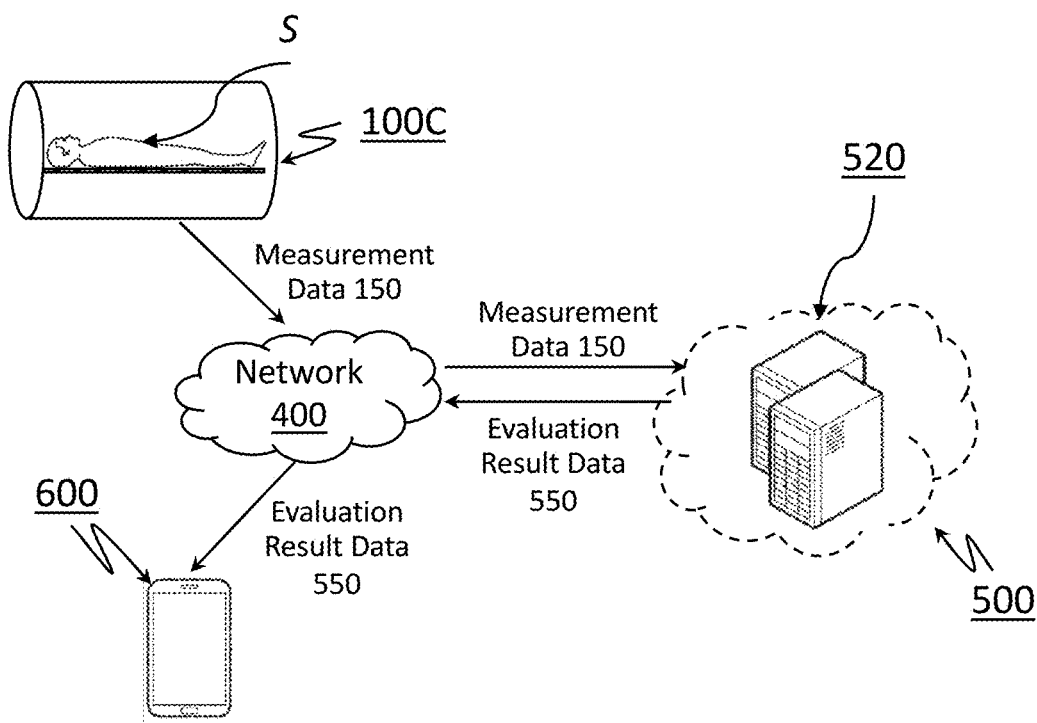

FIG. 11B illustrates another embodiment of the information processing system for the third manner as described above. As shown, in this embodiment of the information processing system, a cloud 500 is also communicatively connected to the network 400, just like the embodiment shown in FIG. 11A. The cloud 500 is provided with a cloud server 520, configured to include the processing device 200 as described above in FIG. 8 (not shown in FIG. 11B). Through the network 400, the measurement data 150 collected by the measuring device (i.e. MRI scanner 100C in FIG. 11B) is first communicated to the cloud server 520 in the cloud 500. Then within the cloud 500, the processing device 200 in the cloud server 520 performs data processing of the measurement data 150 to thereby generate evaluation result data 550 for evaluating the physiological properties of the blood vessel segment in the subject S. Then through the network 400, the evaluation result data 550 is further communicated to a terminal device 600 (e.g. a tablet, a PC, a mobile phone, etc.) for displaying the evaluation result data to a party with an interest (e.g. the subject S or a doctor).

Figure 11C:
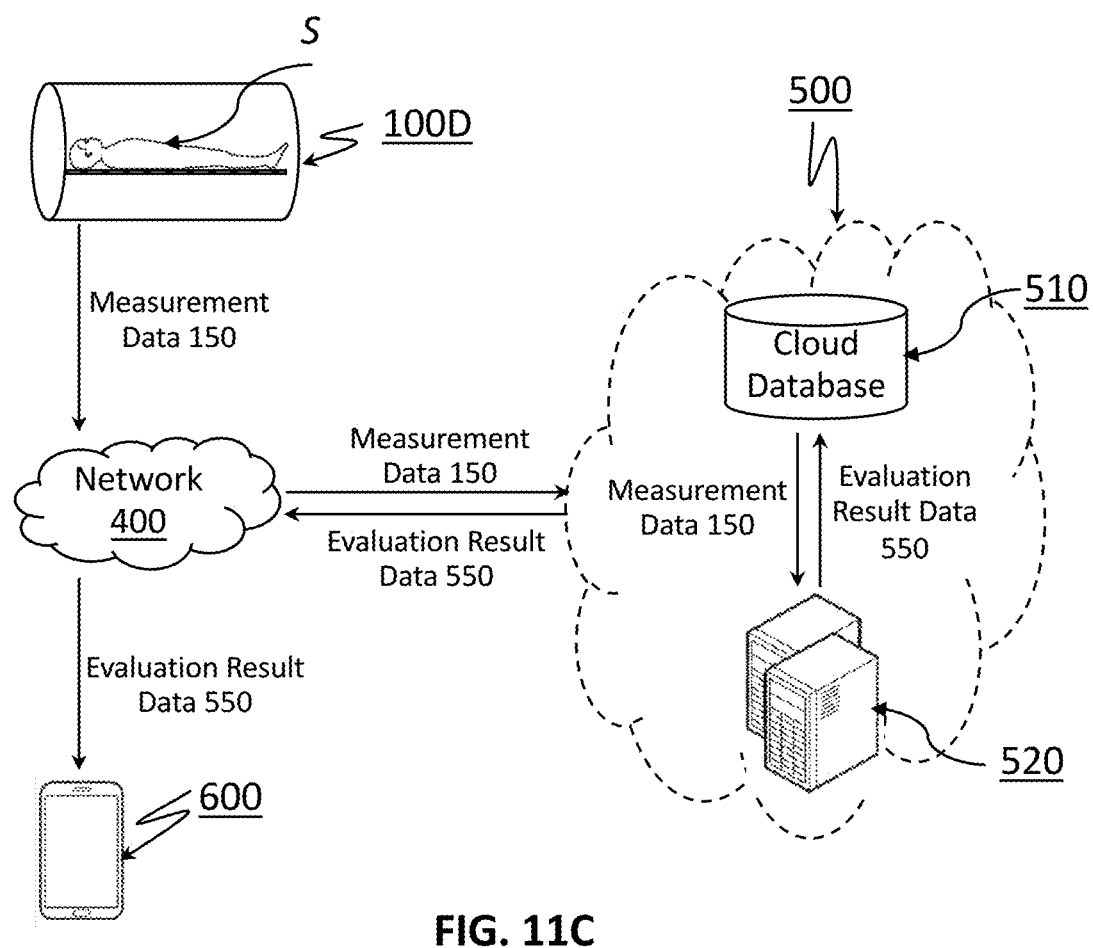

It is noted that optionally, as illustrated in FIG. 11C, in addition to the cloud server 520, the cloud 500 can be further provided with a cloud database 510. Correspondingly, the measurement data 150 collected by the measuring device (i.e. MRI scanner 100D in FIG. 11C) is first communicated to the cloud 500 and stored in the cloud database 510. Then within the cloud 500, the measurement data 150 stored in the cloud database 510 is further communicated to the cloud server 520, where the processing device 200 therein performs data processing of the measurement data 150 to generate evaluation result data 550 for evaluating the physiological properties of the blood vessel segment in the subject S. The evaluation result data 550 can also be stored in the cloud database 510. Then through the network 400, the evaluation result data 550 is further communicated to a terminal device 600 for displaying the evaluation result data to a party with an interest.

Figure 12A:
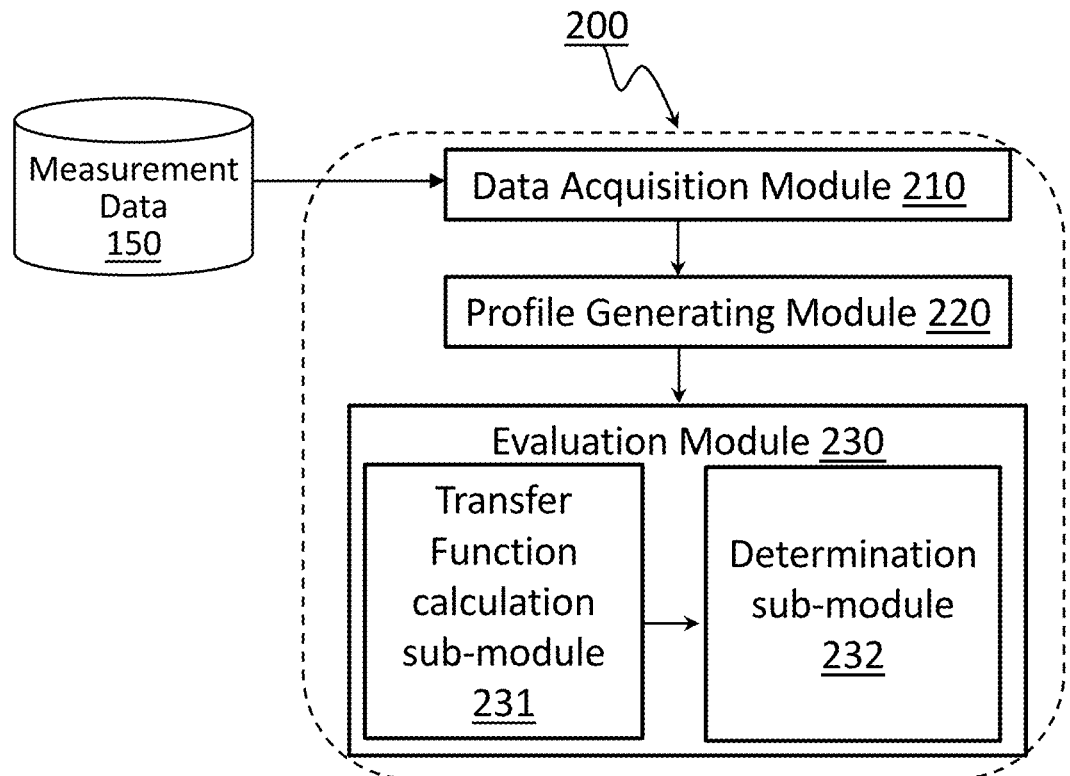
FIGS. 12A and 12B respectively illustrate a block diagram of the various functional modules, and a block diagram of the various hardware components in the processing device as shown in FIG. 8.
Figure 12B:
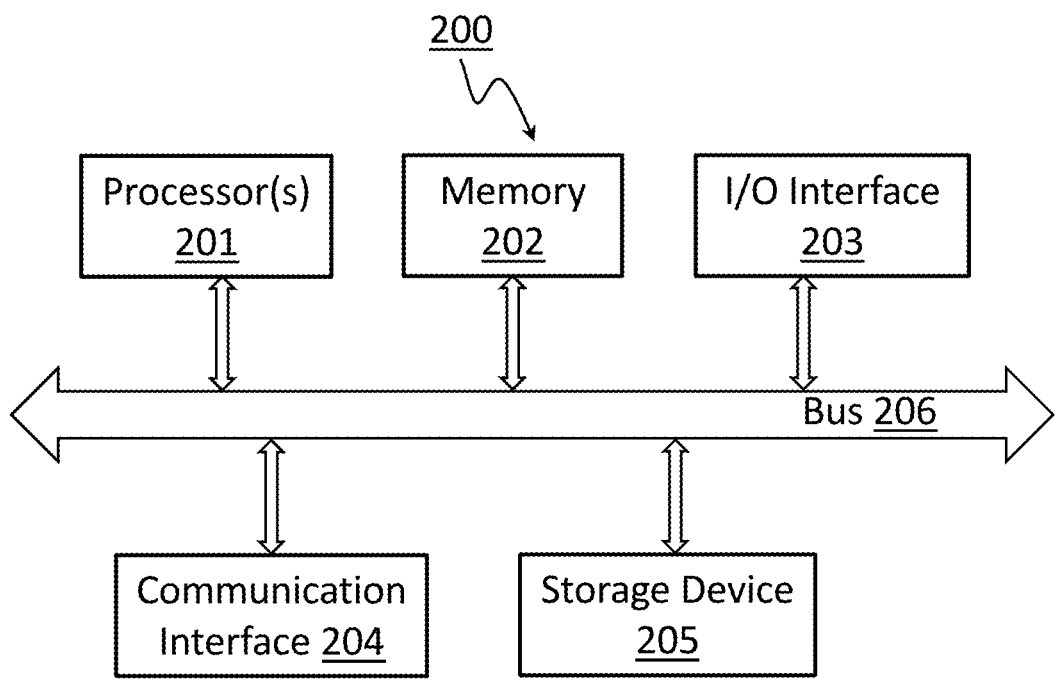

FIGS. 12A and 12B respectively illustrate a block diagram of the various functional modules, and a block diagram of the various hardware components in the processing device 200 as shown in FIG. 8.

As illustrated in FIG. 12A, the processing device 200 in the information processing system 1000 includes a data acquisition module 210, profile generating module 220, and an evaluation module 230. The data acquisition module 210 is configured to acquire the measurement data 150 comprising a series of sequences of measurements collected by the measuring device 100. The profile generating module 220 is configured to generate a series of profiles from the series of sequences of measurements respectively. Herein, depending on the type of the measuring device 100 (not shown in this figure) that is used, each of the series of profiles can be a velocity profile, a pressure profile, or another type of profile, in a manner corresponding to the series of sequences of measurements collected by the measuring device 100. The evaluation module 230 is configured, based on the series of profiles generated by the profile generating module 220, to evaluate the physiological properties of at least one selected subsegment within the segment of the blood vessel. Herein, for each selected subsegment, it has a first end point and a second end point along a blood flow direction, and the first end point and the second end point are substantially two of the series of points along a centerline within the segment of the blood vessel corresponding to which, two sequences of measurements are collected by the measuring device 100 and two corresponding profiles are further generated by the profile generating module 220. Furthermore, the profile corresponding to the first end point is considered as an input profile, and the profile corresponding to the second end point is considered as an output profile.

More specifically, the evaluation module 230 includes a calculation sub-module 231 and a determination sub-module 232. The calculation sub-module 231 is configured to calculate a transfer function corresponding to each selected subsegment. The transfer function is configured to generate an output waveform given an input waveform, using a waveform corresponding to a profile for the first end point (i.e. the input profile) and a waveform corresponding to a profile for the second end point (i.e. the output profile) as the input waveform and the output waveform respectively. The determination sub-module is configured to determine a physiological property of the each selected subsegment based on the transfer function.

More detailed description of how each of the above functional modules (i.e. the data acquisition module 210, the profile generating module 220, and the evaluation module 230) works can be found in the description of an information processing method in the following section of the disclosure.

Herein, and throughout the whole disclosure as well, each of the terms "module," "sub-module," "unit," "sub-unit," or alike, is referred to as a computer-implemented functional entity, which can include both hardware components (i.e. processor(s) or memory) and software components. The combined working of certain hardware component(s) and software components allows a prescribed functionality corresponding to a certain functional module to be carried out in the processing device 200.

More specifically, the processing device 200 can, as further illustrated in FIG. 12B, contain the following hardware components, including at least one processor 201 (i.e. processor(s) in the figure) and a memory 202 which are communicatively connected through a bus 206. The memory 202 is configured to store a software program (i.e. computer codes or executable instructions, not shown in the figure), and the at least one processor 201 is configured to perform a calculation based on the software program stored in the memory 202 to thereby perform a task carrying out the prescribed functionality corresponding to a certain functional module. The processing device 200 can optionally further include an I/O interface 203, a communication interface 204, or a storage device 205, each of which configured to communicate with each other and with the at least one processor 201 and the memory through the bus 206. These optional hardware components respectively allow an input/output between the processing device 200 and a user, acquisition of certain data (e.g. the measurement data 150) to be received to the processing device 200, and the storage of the data.

Herein, the at least one processor may include one or more controllers, general processors, specialized processors, coprocessors, etc., and the at least one processor can be arranged in a parallel processing structure and/or multiprocessing structure. In addition, each of the "module," "sub-module," "unit," "sub-unit," "interface,", or alike, may be a general computer having the software program, or can be a hardware computing device specifically designed for such a task. The computer and the hardware computing device can be locally arranged, or can be remotely arranged through a network, such as an intranet, an internet.

In a second aspect, an information processing method for evaluating physiological properties of a segment of a blood vessel in a subject is provided. The information processing method can be applied to a processing device 200 in the information processing system 1000 as described above.

Figure 13:
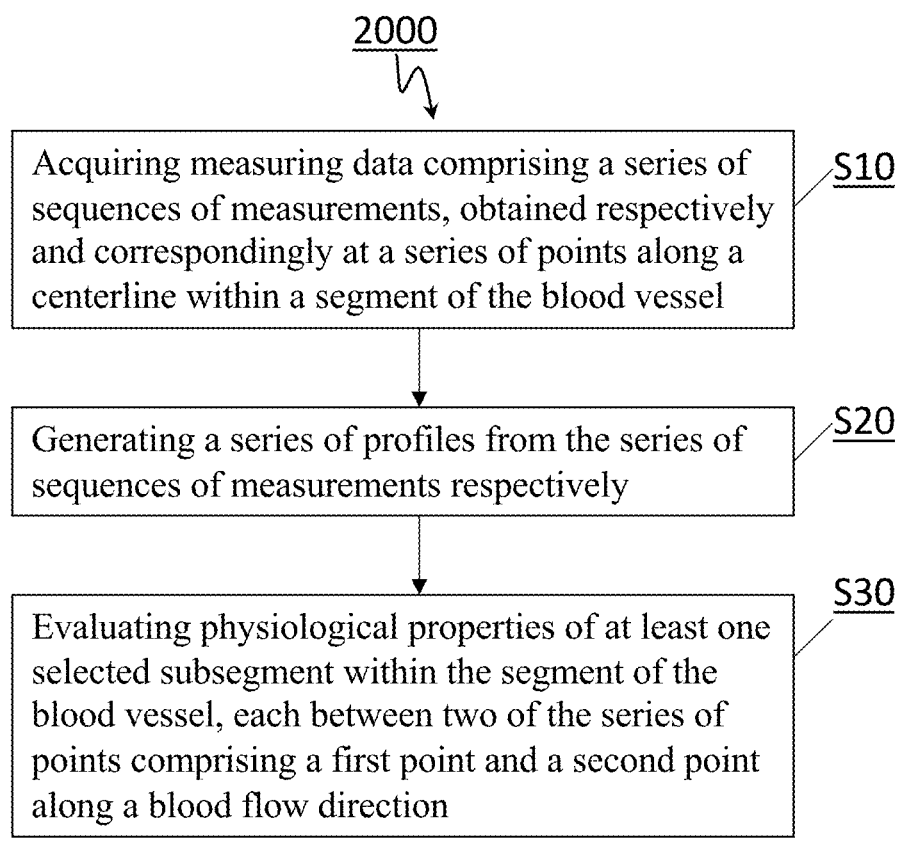
FIG. 13 shows a flow chart of an information processing method according to some embodiments of the disclosure.

As illustrated in FIG. 13, the information processing method 2000 includes the following steps:

S10: acquiring measuring data comprising a series of sequences of measurements, obtained respectively and correspondingly at a series of points along a centerline within a segment of the blood vessel;

S20: generating a series of profiles from the series of sequences of measurements respectively; and S30: Evaluating physiological properties of at least one selected subsegment within the segment of the blood vessel, each between two of the series of points comprising a first end point and a second end point along a blood flow direction.

In order to better understand the various steps in the information processing method 2000 as described above and illustrated in FIG. 13, a specific embodiment is provided in the following, illustrated in FIGS. 14A and 14B. In this embodiment, an MRI scanner capable of performing a phase-contrast MRI scan is used as the measuring device 100 to collect a series of sequences of measurements respectively and correspondingly at a series of points along a centerline within the blood vessel segment of interest.

Figure 14A:
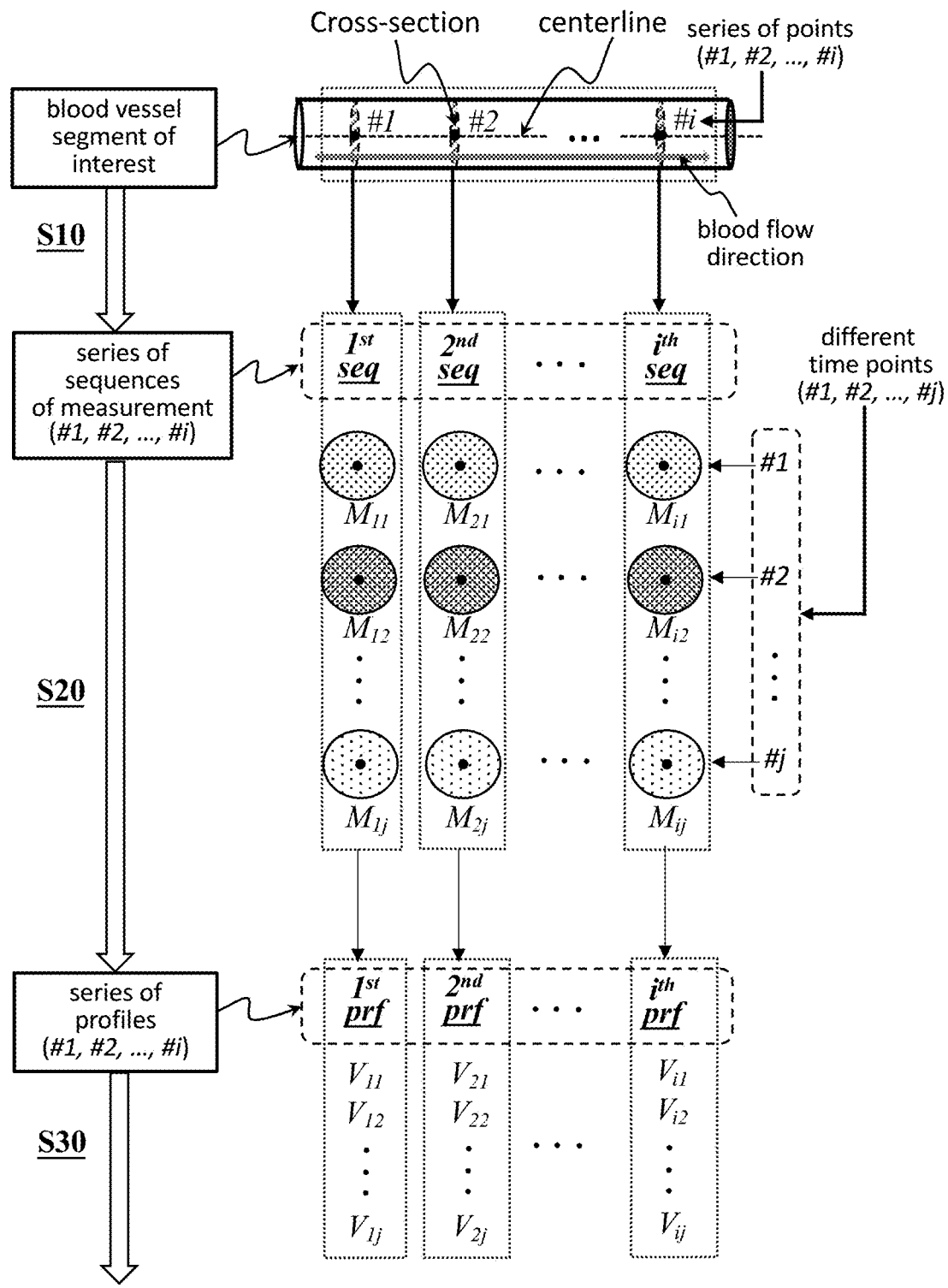
FIGS. 14A and 14B together illustrate the various steps in the information processing method shown in FIG. 13 using a specific embodiment.

As diagramed in FIG. 14A, the blood vessel segment of interest is illustrated as a hollow cylindrical tube, wherein the blood stream flows in a rightward direction. The centerline is defined as a blood stream flow line along the blood vessel segment, illustrated as a linear line that substantially connects the geometric center of each right cross-section on the blood vessel segment. A series of points (shown as #1, #2, . . . , and #1 in the figure) that are spread across the centerline within the blood vessel segment, are the spatial points of interest for collecting their respective and corresponding sequence of measurements thereat, i.e. $1^{st}$ sequence of measurements, $2^{nd}$ sequence of measurements, . . . , and $i^{th}$ sequence of measurements, which together constitute a series of sequences of measurements, shown as "$1^{st}$ seq, $2^{nd}$ seq, . . . , and $i^{th}$ seq" in the figure. As such, the series of sequences of measurements (#1, #2, . . . , and #1) that are taken or reconstituted by the measuring device are in a one-to-one corresponding relationship with the series of points (#1, #2, . . . , and #1) on the centerline within the blood vessel segment of interest.

Furthermore, each sequence of measurements that corresponds to each point on the centerline within the blood vessel segment substantially comprises a total of j measurements which are collected at different time points (shown as #1, #2, . . . , and #j in the figure) within a time period covering at least one cardiac cycle, all at the very same corresponding point within the blood vessel segment. Thus, the $1^{st}$ sequence of measurements (i.e. "$1^{st}$ seq") corresponding to the point #1 in the blood vessel segment substantially is a dataset comprising j measurements that are obtained at each of the different time points (#1, #2, . . . , and #j), shown as $[M_{j1}, M_{12}, \ldots, \text{and } M_{ij}]$; the $2^{nd}$ sequence of measurements (i.e. "$2^{nd}$ seq") corresponding to the point #2 in the blood vessel segment substantially is a dataset comprising j measurements that are obtained at each of the different time points (#1, #2, . . . , and #j), shown as $[M_{21}, M_{22}, \ldots, \text{and } M_{2j}]$; and the $i^{th}$ sequence of measurements (i.e. "$i^{th}$ seq") corresponding to the point #1 in the blood vessel segment substantially is a dataset comprising j measurements that are obtained at each of the different time points (#1, #2, . . . , and #j), shown as $[M_{i1}, M_{i2}, \ldots, \text{and } M_{ij}]$.

In the specific embodiment illustrated in FIG. 14A, each sequence of measurements substantially includes a total of j MRI images that are taken or reconstituted at different time points (#1, #2, . . . , and #j), shown as a column of circles with their inner area shaded differently. The geometrical center of each circle is marked with a black dot, which represents the corresponding point on the centerline within the blood vessel segment at which the corresponding sequence of MRI images are taken or reconstituted. It is noted that in this specific embodiment, each MRI image is substantially a cross-sectional MRI image at a corresponding point on the centerline, having an imaging plane that is substantially perpendicular to the centerline. In other words, each MRI image is an image obtained by the MRI imaging for a right cross-section at a corresponding point on the centerline (i.e. the cross-section that is perpendicular to the centerline). Depending on whether a traditional 2D MRI imaging or a 4D flow MRI imaging is to be used, each MRI image in each sequence of measurement can be directly taken (for 2D MRI imaging, with a prescribed imaging plane that is parallel to the right cross-section of the blood vessel segment), or can be reconstituted (for 4D flow MRI imaging, with no requirement for prescribing any imaging planes).

It is noted that in addition to the series of sequences of MRI images (as the series of sequences of measurements) collected by the MRI scanner (as the measuring device), each sequence of measurements collected at a corresponding point along the centerline within the blood vessel segment can take a different form depending on a different type of the measuring device to be used. For example, if an invasive catheter capable of detecting blood velocity, blood flow, or blood pressure is used as the measuring device, each sequence of measurements at a corresponding point may include a sequence of direct readings (i.e. velocity readings, flow readings, or pressure readings). If a tonometric device, or a fitness wristband is used as the measuring device, each sequence of measurements may also include a sequence of readings of blood pressures. If a Doppler ultrasound device is used as the measuring device, each sequence of measurements may also include a sequence of images containing blood velocity or flow information.

After step S10 in which a series of sequences of measurements as described above is collected by the measuring device and acquired by the processing device, a series of profiles are generated from the series of sequences of measurements in a respectively corresponding manner.

In the specific embodiment illustrated in FIG. 14A, the series of sequences of MRI images (as the series of sequences of measurements) acquired in step S10 can undergo appropriate data processing to extract relevant blood velocity information to thereby obtain the corresponding series of profiles (#1, #2, . . . , and #i). Specifically, for the $1^{st}$ sequence of MRI images ($M_{11}, M_{12}, \ldots, \text{and } M_{ij}$) each MRI image is analyzed, by means of an image processing process, to thereby obtain the corresponding $1^{st}$ velocity profile $[V_{11}, V_{12}, \ldots, \text{and } V_{ij}]$, shown as "$1^{st}$ prf" in FIG. 14A. Similarly, or the $i^{th}$ sequence of MRI images ($M_{i1}, M_{i2}, \ldots, \text{and } M_{ij}$), each MRI image is analyzed, by means of a pixel analyzing process, to thereby obtain the corresponding $i^{th}$ velocity profile $[V_{i1}, V_{i2}, \ldots, \text{and } V_{ij}]$, shown as "$i^{th}$ prf" in FIG. 14A. Herein, the image processing process can be considered as an approach to extract the blood velocity information of the blood flowing through the cross-section of the blood vessel at a particular point on the centerline with the blood vessel segment, based on an MRI image taken (e.g. via a 2D MRI imaging) or reconstituted (e.g. via a 4D flow MRI imaging). More detailed description of the image processing process for how to derive the blood velocity information is provided below.

It is noted that if in Step S10, each sequence of measurements includes a sequence of direct velocity/flow/pressure readings, the generation of a series of profiles corresponding thereto may involve data transfer or data conversion. Thus in an illustrating example (figure not shown) where an invasive catheter is used for the spatially and temporally resolved measurements of blood pressures for the series of points [#1, #2, . . . , and #1], then for a point #k, the sequence of measurements $[M_{k1}, M_{k2}, \ldots, \text{and } M_{kj}]$ collected by the invasive catheter which shall include a sequence of pressure values, may be directly transferrer to, or converted into, a corresponding sequence of blood pressure profiles $[P_{k1}, P_{k2}, \ldots, \text{and } P_{kj}]$.

After step S20 in which a series of profiles are generated from the series of sequences of measurements acquired in step S10, then in step S30, the physiological properties of at least one selected subsegment within the segment of the blood vessel can be evaluated based on the series of profiles generated in step S20. Each such selected subsegment is substantially selected between two of the series of points which consist of a first end point and a second end point along a blood flow direction, and its physiological property is evaluated through appropriate data processing which primarily includes a calculation of a transfer function, configured to generate an output waveform given an input waveform, using a waveform corresponding to a profile for the first end point and a waveform corresponding to a profile for the second end point as the input waveform and the output waveform respectively.

Figure 14B:
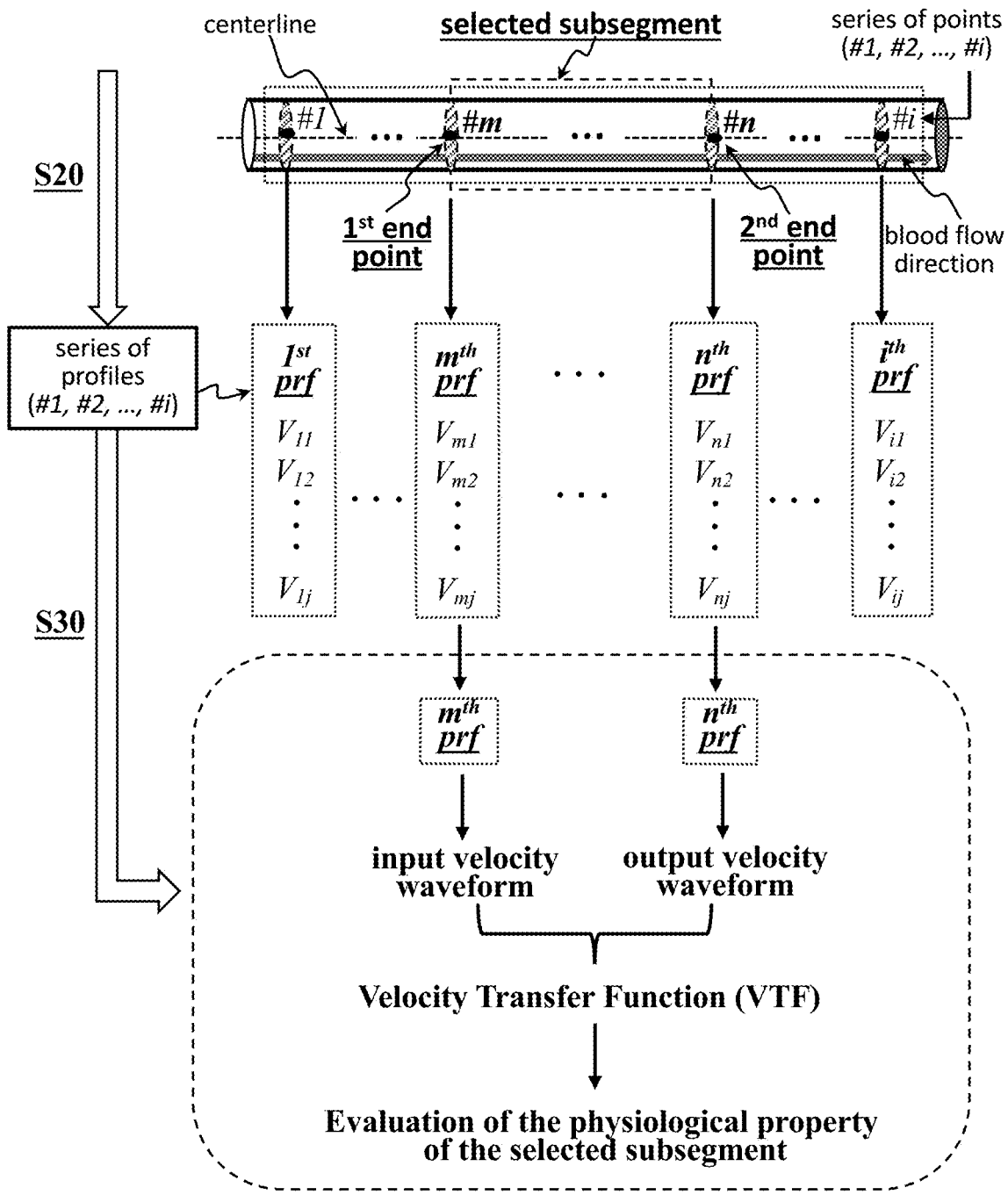

In FIG. 14B, which is substantially a continuation of the embodiment illustrated in FIG. 14A, a subsegment between the point #m and #n is selected for the evaluation of the physiological property thereof. Given the rightward blood flow direction, the point #m is arbitrarily considered as the first end point, and the point #n the second end point. The two velocity profiles corresponding to the two points #m (i.e. the "1$^{st}$ end point") and #n (i.e. the "2$^{nd}$ end point"), i.e. the m$^{th}$ profile [$V_{m1}$, $V_{m2}$, ..., and $V_{mj}$] and the n$^{th}$ profile [$V_{n1}$, $V_{n2}$, ..., and $V_{nj}$] shown as "m$^{th}$ prf" and "n$^{th}$ prf" in the figure, are specifically selected for the generation of an "input velocity waveform" and an "output velocity waveform" respectively. Herein each of the input velocity waveform or the output velocity waveform is substantially a velocity versus time curve for the first velocity profile over one cardiac cycle. Then based on the input velocity waveform and output velocity waveform obtained above, a transfer function, or more specifically a velocity transfer function (VTF) can be calculated, and then the physiological property of the selected subsegment can be further evaluated based on the velocity transfer function (VTF).

Similarly, if blood pressure is the characteristic for generating the series of profiles, i.e. the series of pressure profiles, a pressure transfer function (PTF) can be calculated for a selected subsegment defined by its first end point and second end point based on the pressure profiles corresponding to these two points on the centerline of the blood vessel segment (i.e. the first pressure profile and the second pressure profile). More specifically, an input pressure waveform (i.e. the pressure vs time curve for the first pressure profile over one cardiac cycle) and an output pressure waveform (i.e. the pressure vs time curve for the second pressure profile over one cardiac cycle) can be first generated, then a pressure transfer function (PTF) is calculated, followed by the evaluation of the physiological property of the selected subsegment.

If a characteristic other than blood velocity or blood pressure is relied on for the generation of the series of profiles, a data processing process similar to the above two embodiments (i.e. blood velocity and blood pressure) can be applied to first generate a corresponding transfer function and then to evaluate the physiological property of the selected subsegment based on the calculated transfer function.

In any of the embodiments as described above, the physiological property of the blood vessel as determined above through the transfer function calculation can be considered to correspond to the selected subsegment between the first end point or the second end point. Optionally, the physiological property of the blood vessel thus determined can be considered to correspond to a spatial point on the centerline of the blood vessel segment that is halfway between the first end point and the second end point. In this latter manner, if a sequence of measurements is practically possible to determine for each of a large number of points along the centerline of the blood vessel segment, it allows for a continuous analysis to determine the distribution of the physiological property of the blood vessel segment along the centerline thereof.

Figure 15:
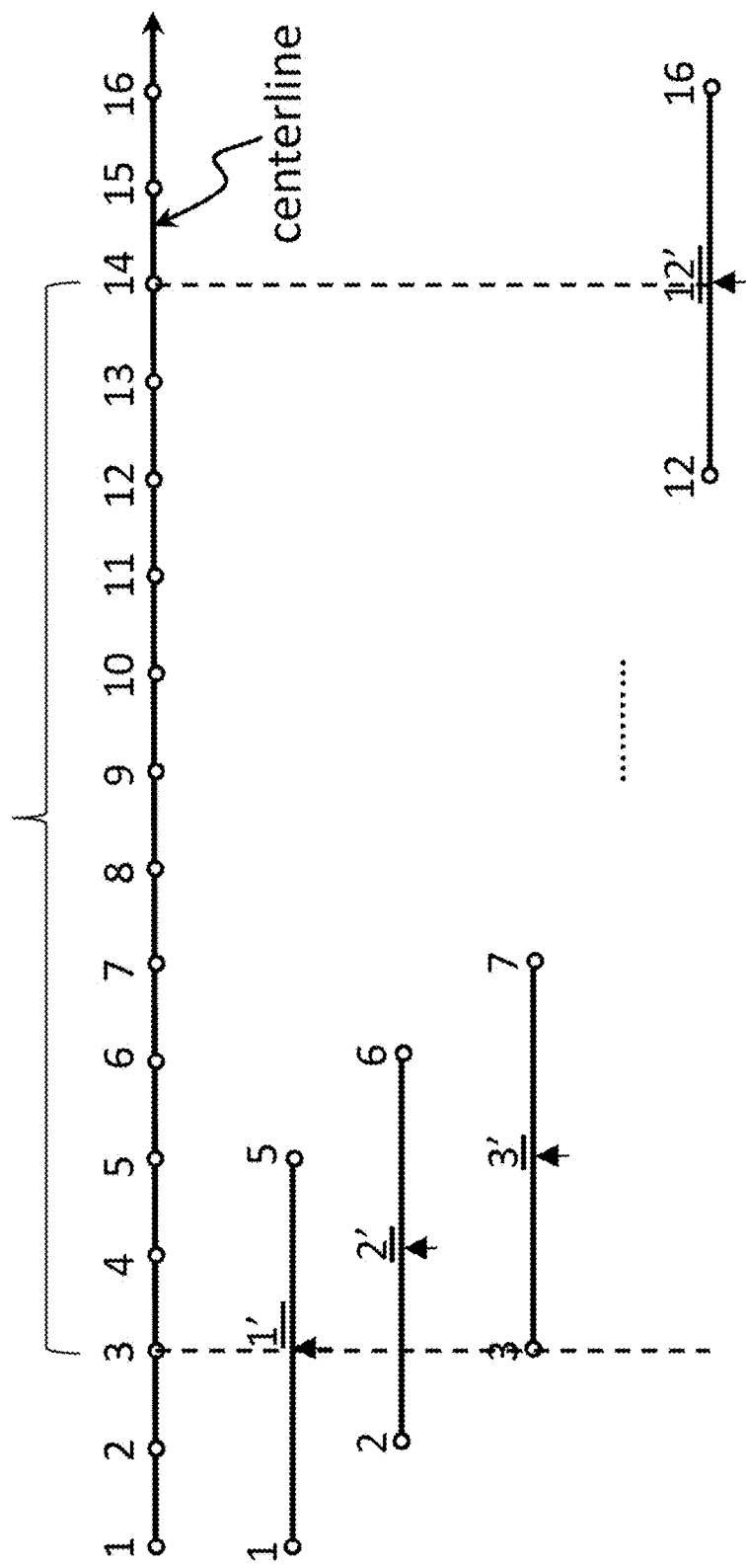
FIG. 15 provides an illustrating example for a working process of a continuous analysis of the physiological properties of the blood vessel segment at different points along the centerline thereof.
Figure 16:
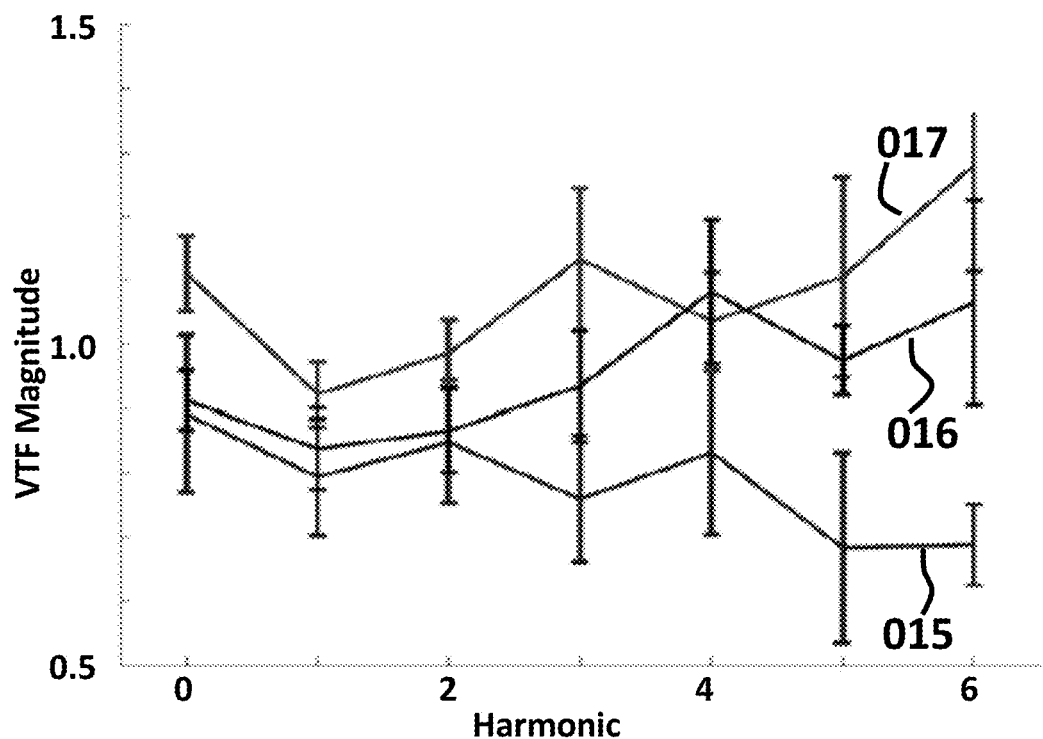
FIG. 16 shows VTF magnitude versus harmonic for PH patients (017, n=8), COPD patients (016, n=8) and normal volunteers (015, n=4), where the VTF at zero harmonic is greater in PH than normals or COPD, which is consistent with high PVR values expected in PH, yet at higher harmonics the COPD group behaves similar to the PH group suggesting increased PA stiffness.

FIG. 15 provides an example intended to illustrate a working process of a continuous analysis of the physiological properties of the blood vessel segment at different points along the centerline thereof. In this simplified example, a total of 16 points that are equally spaced apart from one another (#1, #2, ..., and #16) are arranged on the centerline within a blood vessel segment of interest (for simplicity, only the centerline is shown in the figure, and the blood vessel structure is intentionally omitted). At each of these 16 points, a sequence of measurements is correspondingly collected by a measuring device, which are obtained at different time points of at least one cardiac cycle of the subject. A corresponding series of profiles are further generated.

In order to obtain a continuous physiological property distribution along the centerline of the blood vessel, consecutively sliding windows of subsegment are selected, each containing a pair of a first end point and a second end point. As illustrated in FIG. 15, 12 consecutively sliding subsegments [#1, #5], [#2, #6], [#3, #7], ..., and [#12, #16] are selected for the calculation of their respective transfer function to thereby determine their respective physiological property. For each such subsegment, the physiological property thus determined can be regarded to correspond to a spatial point on the centerline that is halfway between the first end point and the second end point, as shown by the halfway points #1', #2', #3', ..., and #12' in each of the 12 sliding subsegments. By their spatial correspondence, they roughly project to a segment between the points #3 and #14 on the centerline, as indicated by the large bracket positionally arranged over the centerline. For this specific subsegment [#3, #14], the physiological properties at each point #3, #4, #5, ..., and #14 can be determined to thereby realize a close-to-be continuous mapping of the physiological properties on the blood vessel segment.

In this simplified example in FIG. 15, the centerline is drawn as a straight line, but it should be noted that the centerline can be a curved line as well, or that the 16 points are not equally spaced apart from one another. Under these situations, the halfway points #1', #2', #3', ..., and #12' do not necessarily coincide onto the points #3, #4, ..., and #14.

This continuous physiological property mapping approach can be applied regardless of which characteristic (i.e. velocity, pressure, etc.) is to be measured, and what measuring device is to be used. Yet for MRI-based blood velocity measurement, it is noted that the traditional 2D phase-contrast MRI imaging (2D PC-MRI) has remained a technical challenge for the continuous physiological property mapping.

In 2D PC-MRI, for each MRI image to be taken, each slice must be individually prescribed based on different views of the patient. If an imaging plane is incorrectly positioned or oriented (i.e. not perpendicular to the blood vessel segment of interest), this error is usually not discovered until after the scan is complete and the patient has left the scanner. The most common problems are slices that are not perpendicular to the blood vessel segment of interest (e.g. a segment of an artery) and inconsistent spacing between the proximal and distal imaging planes.

With the recently emerging 4D flow MRI imaging technology, the cross-sectional MRI images can be reconstituted at a latter time without the need to prescribe any imaging planes before. In other words, the location and orientation of analysis planes can be performed after data acquisition and can be adjusted and optimized as much as needed with no penalty. This makes it easier to prescribe analysis planes that are perpendicular to the artery and achieve a consistent spacing between analysis planes. VTF can also be easily measured between a large number of planes. This capability makes a continuous analysis of a physiological property distribution on a blood vessel of interest (e.g. pulmonary arterial stiffness) possible. For example, a single plane could be placed in the MPA and then a series of planes could be placed, say 1.5 mm apart, from the MPA location to the bifurcation and along the RPA. VTF stiffness parameters could be computed between the first MPA plane and each subsequent RPA yielding a continuous measurement of stiffness from the MPA to the distal RPA. A similar analysis could be performed on the LPA. This analysis could yield new insights into the pathology of diseases like COPD, which can have substantial differences in stiffness in different parts of the pulmonary arterial tree.

In the following, a total of five clinical examples are provided to provide the support to the present disclosure.

Clinical Example 1

Figure 18:
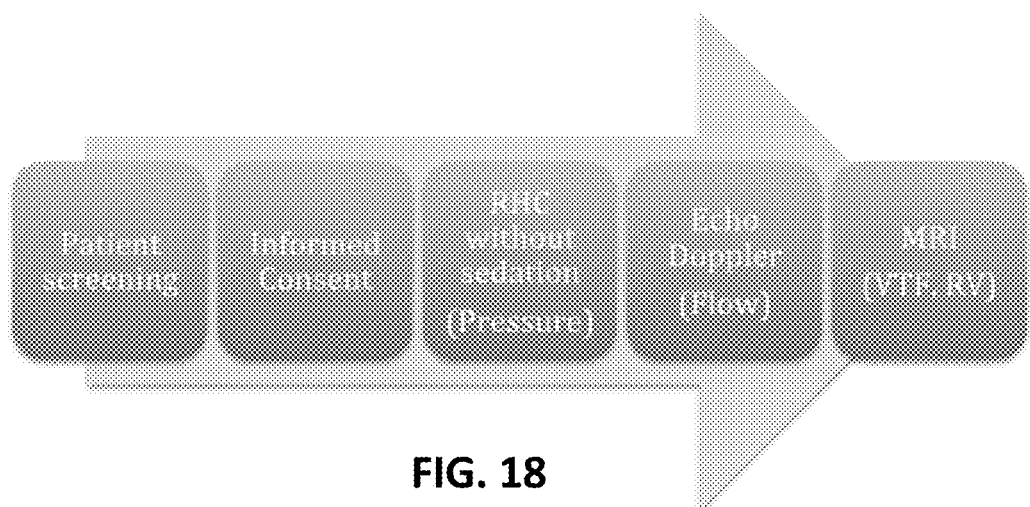
FIG. 18 illustrates the patient flow in Clinical Example 2.

Patients with primary pulmonary hypertension (PH) (n=8), chronic obstructive pulmonary disease (COPD) Gold Stage I-III with no clinical evidence of PH (n=8) and normal controls (n=4) were studied. Each subject underwent PC-MRI to obtain velocity profiles through a slice in the main pulmonary artery (MPA) and a slice through the right pulmonary artery (RPA) proximal to the bifurcation. FIG. 18 shows the VTF magnitude versus harmonic for a group of PH patients (017, n=8), COPD patients (016, n=8) and normal volunteers (015, n=4). The VTF at zero harmonic is greater in PH than normals or COPD, which is consistent with high PVR values expected in PH. However, at higher harmonics the COPD group behaves similar to the PH group suggesting increased PA stiffness.

FIG. 18 shows the average VTF magnitude and phase computed from normal volunteers (normals, 015), patients with PH (017), and patients with COPD (016). These spectra are plotted versus harmonic number. As expected, in PH patients with much stiffer arteries, the magnitude spectrum is fairly constant and the phase is relatively linear over the first 6 harmonics (illustrated in 017). At zero harmonic, the magnitude of VTF is higher in the PH group compared to normals. It is interesting to note that at zero harmonic, the magnitude of VTF in COPD group is similar to normals but at higher harmonics magnitude in COPD patients behave like those with PH rather than like normals. Thus, at the zero harmonic that correlates with traditional PVR measurement, COPD patients in this pilot study would have considered to have normal PVR, PA pressures, and vessel stiffness. But with VTF analysis at higher harmonics, it was clear that it might not be the case for the vessel stiffness. Based on these results, the VTF is a promising method to detect vessel wall stiffness non-invasively earlier in time than traditional invasive measures of PA pressures or PVR. These preliminary results incorporating VTF are consistent with theoretical predictions of the stiff tube model (FIGS. 1A-1C, and FIGS. 4A-4D).

Figure 17A:
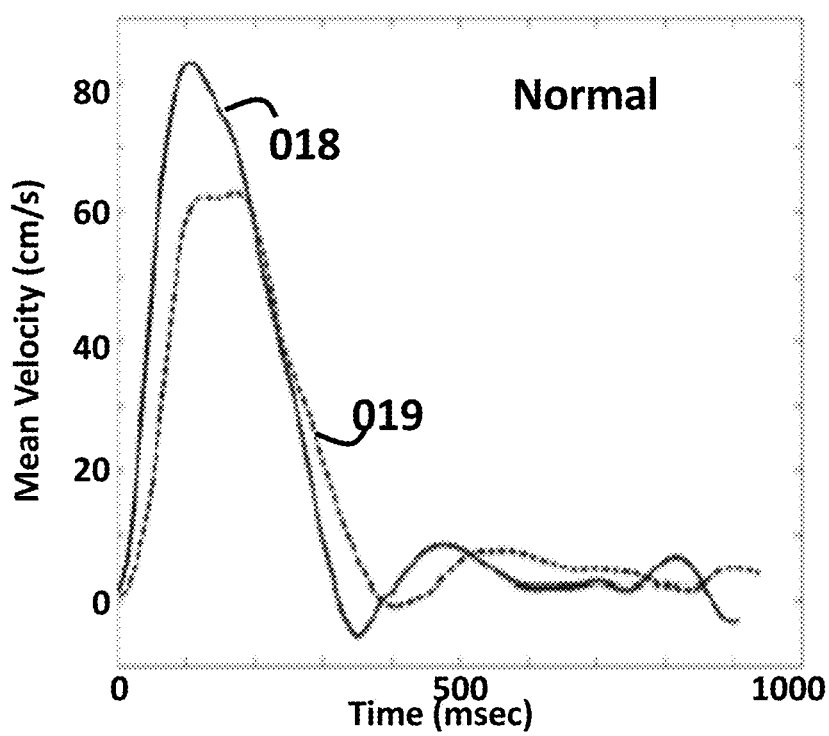
FIGS. 17A-17C show representative individual average velocity profiles at a point in the main pulmonary artery (018, 020, 022) and right pulmonary artery proximal to the bifurcation (019, 021, 023), and the difference in shift of velocity profiles in normal, COPD, and PH are respectively shown in FIGS. 17A-17C.
Figure 17B:
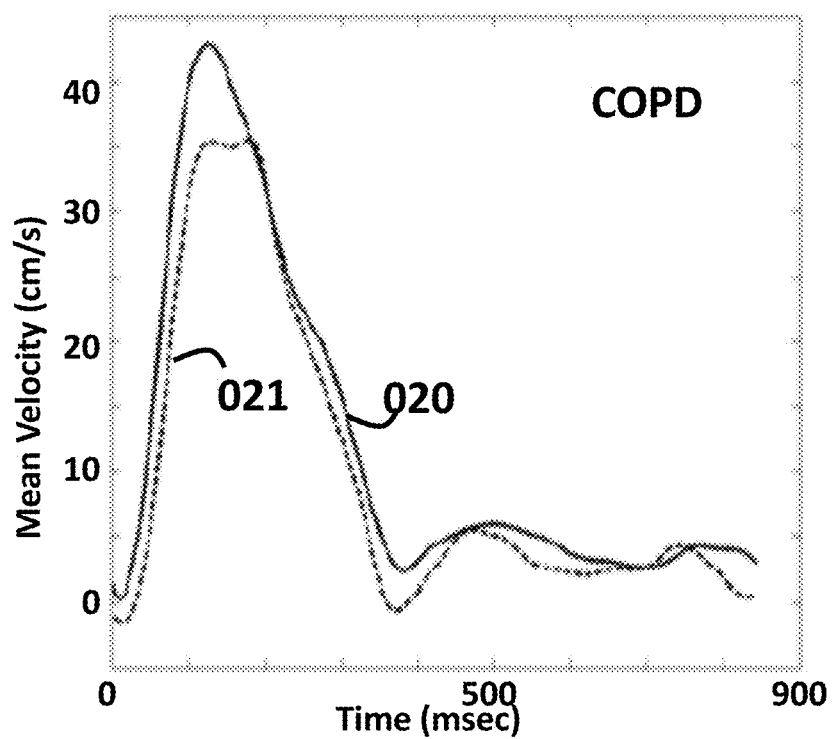
Figure 17C:
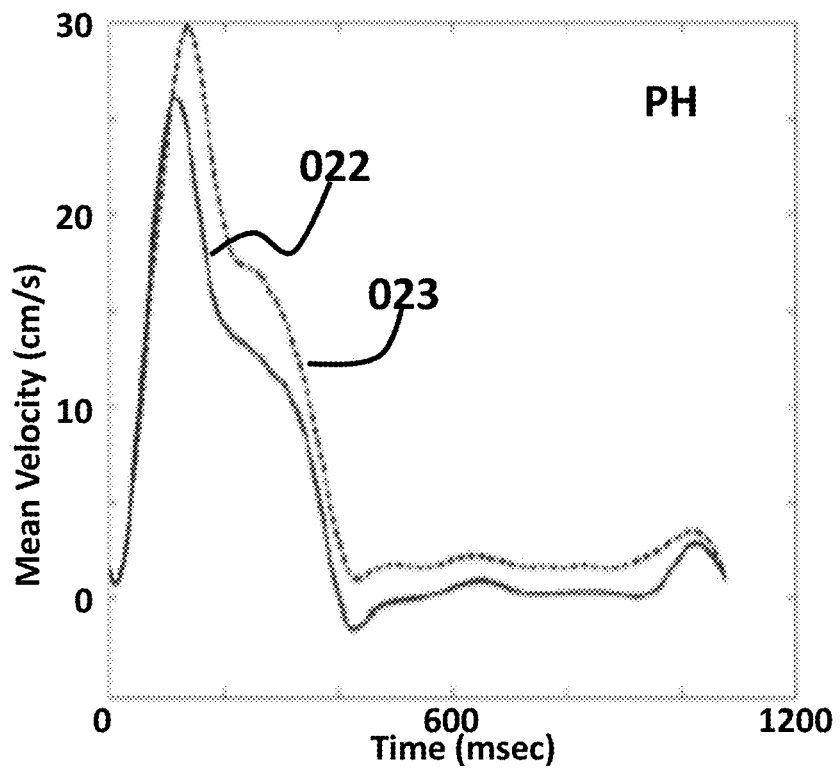

Similar results can be seen in the individual velocity plots shown in FIGS. 17A-17C, where the RPA velocity is a time shifted and scaled version of the MPA velocity. FIGS. 17A-17C show representative individual average velocity profiles at a point in the main pulmonary artery (018, 020, 022) and right pulmonary artery proximal to the bifurcation (019, 021, 023). Note the difference in shift of velocity profiles in normals (FIG. 17A) vs COPD (FIG. 17B) vs PH (FIG. 17C).

As shown in FIG. 9A, in normal subjects with compliant arteries, the RPA velocity profile (019) is broadened compared with the MPA velocity profile (018). FIG. 18 shows plots of average VTF magnitude versus harmonic for the three groups. In COPD (which were Gold Stage I-III with no clinical evidence of PH, the results of the VTF magnitude (016) were found to be intermediate between PH (017) and normals (015), indicating that the PA is stiffer than normals.

Clinical Example 2

In this study, it was hypothesized that a non-invasive PC-MRI derived VTF embodiment correlates with increased PA stiffness/resistance and therefore can provide non-invasive assessment of the pulmonary arterial circuit and RV-PA coupling, which is a condition where RV blood pumping function is impaired due to increased arterial stiffness. In this pilot study, patients who had undergone clinically indicated right heart catheterization (RHC) were prospectively evaluated with cardiac MRI (CMR). The following specific aims were tested:

Specific Aim 1: To test the hypothesis that novel non-invasive CMR derived VTF, $S_V(f)$, correlates with the changes in PA stiffness/resistance as measured by invasive impedance.

Sub Aim 1: To test whether relationship is independent of elevation in pulmonary capillary wedge pressure (PCWP).

Sub Aim 2: To test intra- and inter-observer reliability of VTF measurement.

Specific Aim 2: To test the hypothesis that the VTF, $S_V(f)$, correlates with changes in RV structure and function.

Methods.

Sample Population: Inclusion criteria: Patients who had undergone successful clinically indicated outpatient RHC at University of Alabama at Birmingham Hospital and The Kirklin Clinic and are willing to undergo CMR. Exclusion criteria: Patients were excluded from the study if they had any contraindication for CMR (MRI incompatible metal prosthesis, claustrophobia), are on inotropic therapy, ventricular assist device or have history of heart or lung transplantation.

A total of 104 patients were screened of which 39 were eligible to participate in the study. 26 patients consented to participate of which 6 patients unsuccessfully attempted CMR examination due to realization of claustrophobia that they were not aware of before. A total of 20 patients were thus enrolled (10 with PVR<2.5: Normal PVR group, 10 with PVR≥2.5: High PVR group). Of these 20 patients, 1 patient had invasive impedance and CMR VTF measured by phase contrast sequences but could not complete the cine steady state free precession sequence for RV mass, volume and function assessment due to an unexpected technical problem with MRI scanner.

Patient Flow: Eligible patients who consented for the study underwent clinically indicated RHC. PA pressure measurements were obtained using Swan-Ganz PA catheter in the MPA. For flow measurement, blood flow velocity profile was obtained using transthoracic pulmonary arterial pulsed wave Doppler in MPA during or around the time of RHC. The analysis of these two measurements (as detailed below) resulted in calculation of invasive impedance. They then underwent same day CMR examination including PC sequences for VTF, RV structure and function analysis. The patient flow can be visualized in FIG. 18. The study was approved by University of Alabama at Birmingham Institutional Review Board.

Figure 19A:
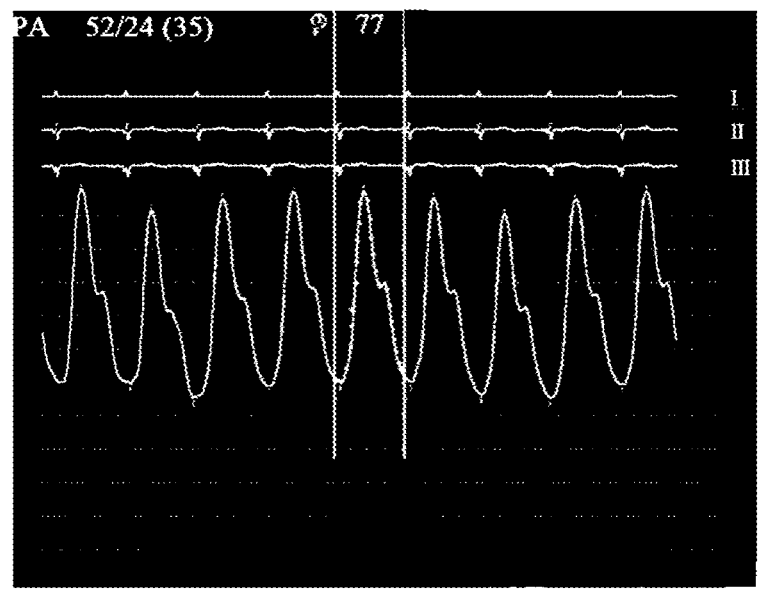
FIGS. 19A and 19B show digitization of main pulmonary artery pressure waveform in one cardiac cycle (FIG. 19A) and digitization of main pulmonary artery pulsed wave Doppler waveform in one cardiac cycle (FIG. 19B)
Figure 19B:
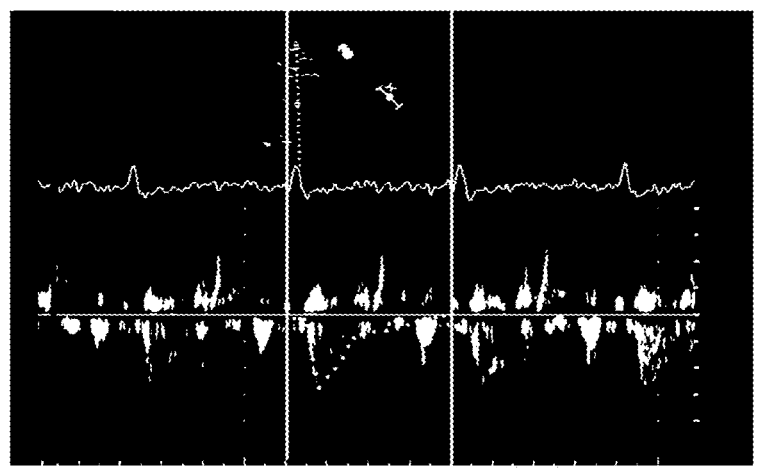

RHC, Doppler Echocardiography And Invasive Impedance Measurement: MPA pressure obtained from invasive RHC and MPA blood flow velocity profiles obtained from pulsed wave Doppler were synchronized using electrocardiogram artifact. These waveforms were then digitized using WebPlotDigitizer version 3.8 as shown in FIGS. 19A and 19B.

The digital data was extracted as comma separated values format. The velocity profile was converted to flow profile using the correction factor (Hunter, K. S., et al., 2008)

$$Q(t)=A_{corr}V(t)$$

$$A_{corr}=CO\ V_{mean}$$

where Q(t) is the calculated flow-time history, V(t) is the velocity-time history obtained from digitized pulsed wave Doppler waveform, $A_{corr}$ is the correction factor applied to convert velocity-time to flow-time, CO is cardiac output obtained from right heart catheterization, $V_{mean}$ is the mean velocity computed from the midline velocity-time history. Impedance was then calculated by obtaining discrete Fourier transformation on the digitized data using Matlab version 2015a.

RHC protocol: After informed consent, patients underwent clinically indicated right heart catheterization with 5 F Swan-Ganz fluid filled catheter via right internal jugular vein under local anesthesia only without intravenous sedation.

Transthoracic Doppler echocardiography protocol: With patient in left lateral decubitus position and transducer in left parasternal intercostal space (usually 3rd or 4th), short axis view of heart was obtained at the level of the aortic valve. Pulsed-wave Doppler echocardiography was then obtained in this view with 2 mm sample volume placed 0.5-1 cm distal to pulmonic valve in the main pulmonary artery. Doppler echocardiography was obtained using Philips IE33 ultrasound system.

Figure 20:
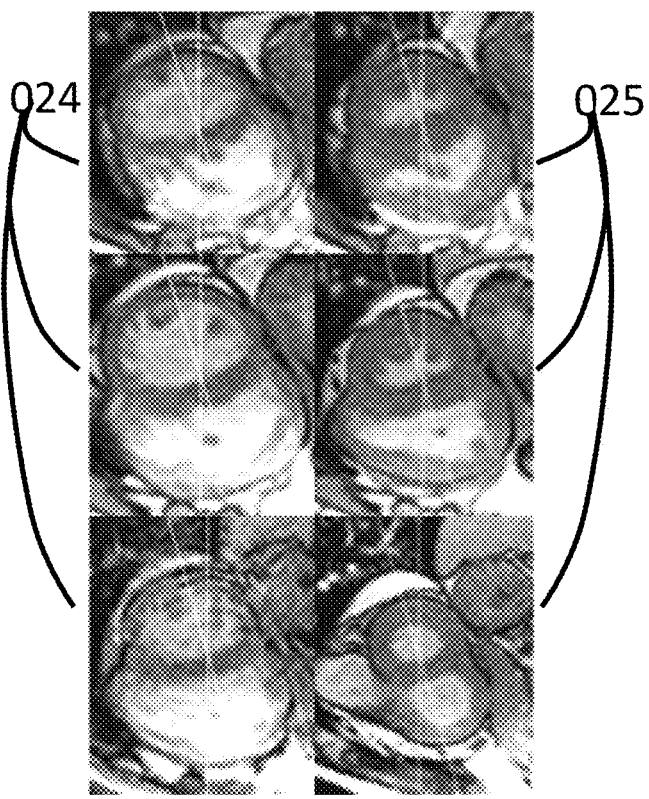
FIG. 20 illustrates right ventricular diastolic (024) and systolic (025) frames obtained from cine-cardiac magnetic resonance imaging. The green lines denote intersection with 4-chamber and left ventricular outflow tract slices.

CMR Imaging and Velocity Transfer Function Measurement:

Comprehensive CMR consisting of cine and phase contrast sequences was performed on the same day of pressure-flow measurements to maintain the close temporal relationship and to minimize significant alteration in hemodynamic state. It included assessment of flow in the MPA, proximal (to the bifurcation) RPA, distal RPA, and proximal LPA using a PC-CMR technique (FIGS. 2A and 2B). Mean velocity-time profile over a cardiac cycle (FIG. 3) and accurate assessment of RV mass, volumes and function (FIG. 20) were obtained.

MRI Protocol: Magnetic resonance imaging was performed on a 1.5-T magnetic resonance scanner (GE Signa, Milwaukee, Wis.) optimized for cardiac application. Cine SSFP: Electrocardiographically (ECG)-gated breath-hold steady-state free-precision technique was used to obtain standard 2-chamber, 4-chamber and short-axis views with following general parameters: prospective ECG gating, slice thickness=8 mm, 2 mm interslice gap, field of view=40×40 cm, scan matrix=224×128, flip angle=45°, repetition/echo times=3.8/1.6 ms. Twenty cardiac phases were reconstructed with 8 views per segment.

A short-axis stack was positioned from an end-diastolic 4-chamber image, centered parallel to the mitral annulus and perpendicular to the septum, starting 1 cm proximal to the mitral valve to 1 cm beyond the apex. Analysis was performed using CAAS MRV 3.4 (Pie Medical Imaging, Netherland). Phase-contrast MRI: It was performed using ECG gated, breath-hold fast gradient recalled echo phase contrast sequence (Fast 2D Phase contrast). Typical parameters were: field of view=40 cm, scan matrix=256×128, encoding velocity 150 cm/s, NEX=1, flip angle=15°, repetition/echo times=7.6/3.1 ms, band width+/−31.25 KHz, views per segment 8. 20 phases were reconstructed. Contours were drawn using CAAS MR Flow ver 1.2 (Pie Medical Imaging, Netherland) and exported as .csv format for analysis using MATLAB 2015a.

In addition to VTF and invasive input impedance, the traditional pulmonary artery stiffness parameters in TABLE 1 were also studied.

TABLE 1

Pulmonary artery stiffness parameters.

| Parameters | Definition | Formula | Units | Technique |
|---|---|---|---|---|
| VTF ($S_F$(f)) | Transfer function of velocity at MPA as input and RPA or LPA as output. | $V_{RPA}$(f)/ $V_{MPA}$(f) | unitless rad | MRI |
| Input Impedance ($Z_i$) | Ratio of pulsatile pressure to pulsatile flow at input of an arterial site | P/Q | mm Hg/ (L/min) rad | RHC + Doppler |
| Impedance Modulus (Z) | Ratio of modulus of pressure and flow | \|P\|/\|Q\| | mm Hg/ (L/min) | RHC + Doppler |
| Impedance Phase (θ) | Fraction of wave cycle that has elapsed relative to each other | β-φ | rad | RHC + Doppler |
| PVR | Static resistance | $(P_2-P_1)$/Q | Woods Units | RHC |
| PA-Ao Diameter Ratio | Ratio of pulmonary artery to aortic root diameter | PA diameter/ Aortic root diameter | unitless | MRI |
| Capacitance | Volume change per unit pressure | SV/PP | $cm^3$/mm Hg | RHC |
| Pulsatility | Relative area change of MPA | [(maxA-minA)/ minA] × 100 | % | MRI |
| Compliance | Area change per unit pressure | (maxA-minA)/PP | $mm^2$/mm Hg | MRI + RHC |
| Distensibility | Relative area change per unit pressure | [(maxA-minA)/ minA × PP] × 100 | %/mm Hg | MRI + RHC |
| Elastic Modulus | Driving pressure effecting a unit relative area change | (PP × minA)/ (maxA-minA) | mm Hg | MRI + RHC |
| Stiffness Index | Slope of function between distending arterial pressure and arterial distention | [ln(PASP/ PADP)]/ [(maxA − minA)/ minA] | unitless | MRI + RHC |

Note:
A: area,
Ao: aortic root,
MPA: main pulmonary artery,
MRI: magnetic resonance imaging,
P: pressure,
PA: pulmonary artery,
PASP: pulmonary artery systolic pressure,
PADP: pulmonary artery diastolic pressure,
PP: pulse pressure,
Q: flow,
RHC: right heart catheterization,
RPA: right pulmonary artery,
VTF: velocity transfer function,
VRPA(f): velocity function at RPA,
VMPA(f): Velocity function at MPA.

Demographics, clinical and imaging characteristics of normal and high PVR groups were compared using t-test or Wilcoxon test (if non-normal data) for continuous variables and Fisher's exact test for categorical variables. Repeated mixed-model analysis using the SAS MIXED procedure was performed on zero and first six harmonics of both invasive impedance as dependent variable and VTF as predictor variable to assess association of VTF with invasive impedance (Model: Invasive impedance=MRI Harmonics MRI*Harmonics). Unstructured covariance structure for the error term was fitted to accommodate correlation between various harmonics from the same subject. Averages of the zero and first harmonics for invasive impedance and averages of the fifth and sixth harmonic for VTF were computed. Mean high frequency magnitude, MHFM, was defined as average magnitudes of 5th and 6th harmonics of VTF. Average impedance and MHFM curves were then studied for correlation. All studies were evaluated by cardiologists: AG, twice, and HG once, in an independent and blinded fashion for calculation of VTF. Intra-class correlation was used to investigate intra- and inter-observer reliability in calculation of VTF. Intra-class correlation coefficient was calculated using a SAS macro. Linear regression model was used to study association of RV mass, volume and function parameters with MHFM. Logistic model was used to obtain Receiver Operative Characteristic (ROC) curve to study performance of MHFM in differentiating patients with high or normal PVR. A p<0.05 was considered statistically significant. No adjustment of p-value was done for multiple statistical tests due to being a pilot study. All statistical analyses were performed using SAS version 9.4.

Results.

Patients' Clinical And Imaging Characteristics: The study population comprised of middle-aged predominantly Caucasian individuals with typical comorbidities as outlined in TABLE 2.

TABLE 2

Demographics and clinical characteristics.

| Clinical Characteristics | All (n = 20) | Normal PVR Group, PVR < 2.5 (n = 10) | High PVR Group, PVR ≥ 2.5 (n = 10) |
|---|---|---|---|
| Age, years | 55.25 ± 18.6 | 50.6 ± 21.17 | 59.9 ± 15.3 |
| Sex, females | 14 | 9 | 5 |
| Race | | | |
| Black | 3 | 2 | 1 |
| White | 17 | 8 | 9 |
| Body mass index, kg/m² | 27.55 ± 6.9 | 28.22 ± 7.47 | 26.88 ± 6.56 |
| Obesity | 7 | 4 | 3 |
| Smoking | | | |
| Never | 11 | 7 | 4 |
| Past | 9 | 3 | 6 |
| Current | 0 | 0 | 0 |
| Diabetes | 2 | 2 | 0 |
| Hypertension | 9 | 5 | 4 |
| Dyslipidemia | 11 | 5 | 6 |
| Coronary artery disease | 3 | 2 | 1 |
| Congestive heart failure | 4 | 2 | 2 |
| COPD | 1 | 1 | 0 |
| Interstitial lung disease | 4 | 1 | 3 |
| Obstructive sleep apnea | 4 | 2 | 2 |
| New York Heart Association Class | | | |
| 1 | 2 | 2 | 0 |
| 2 | 10 | 4 | 6 |
| 3 | 8 | 4 | 4 |
| Chronic kidney disease (eGFR < 60) | 5 | 3 | 2 |
| PVR, Woods Units | 3.43 ± 2.86 | 1.34 ± 0.59 | 5.51 ± 2.7 |
| Medications | | | |
| Oral nitrates | 2 | 1 | 1 |
| Phosphodiesterase inhibitors | 7 | 2 | 5 |
| Endothelin receptor antagonists | 3 | 1 | 2 |
| Prostacyclin analogues | 2 | 0 | 2 |
| Calcium channel blockers | 6 | 4 | 2 |
| Beta-blockers | 7 | 5 | 2 |
| ACEI/ARB | 3 | 2 | 1 |
| Aldosterone antagonists | 6 | 3 | 3 |

Note:
Continuous variables are in mean ± SD, discrete variables are in number of individuals,
*p value <0.05 for normal vs high PVR groups.
ACEI: angiotensin converting enzyme inhibitors;
ARE: angiotensin receptor blockers;
COPD: chronic obstructive pulmonary disease;
eGFR: estimated glomerular filtration rate, ml/min;
PAP; pulmonary artery pressure;
PCWP: pulmonary capillary wedge pressure;
PH: pulmonary hypertension;
PVR: pulmonary vascular resistance.

Figure 21:
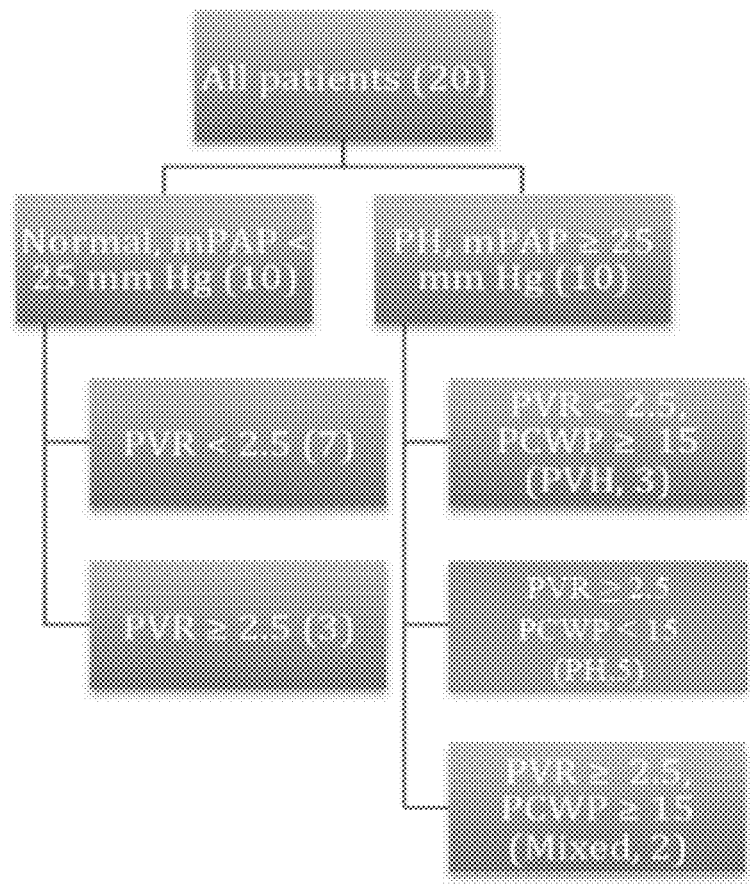
FIG. 21 illustrates the patient distribution for Clinical example 2 based on pulmonary pressures and/or resistance, where mPAP is the mean pulmonary artery pressure, PCWP the pulmonary capillary wedge pressure, PH pulmonary hypertension, PVH pulmonary venous hypertension, and PVR pulmonary vascular resistance.

Of the 20 patients, 10 patients had normal PA pressures as defined by mean PA pressure<25 mm Hg (FIG. 21). PVR of these 10 patients with normal mean PA pressure was 1.76±0.78 (mean±SD) Woods Units (WU). 1 SD above the mean PVR was approximately 2.5 WU. Also, clinically the detection of early PA remodeling (PVR between 2.5 and 3) is of interest. Therefore, study patients were divided into two groups—a Normal PVR group (10 patients) with PVR<2.5 WU and a High PVR group (10 patients) with PVR 2.5.

RHC and Doppler as well as RHC and MRI data were acquired closely in time (time difference: 0.029±0.04 hours, 2.38±1.15 hours respectively), TABLE 3. Bland-Altman analysis revealed excellent correlation and agreement between inter-modality heart rate, blood pressure and cardiac indices, as shown in TABLE 3.

TABLE 3

Inter-modality time, heart rate, blood pressure and cardiac index differences.

| | Correlation | | Agreement | |
|---|---|---|---|---|
| Parameter | Pearson r | p-value | Relative bias ± SD | p-value (mean vs bias) |
| Time difference, hours | | | | |
| RHC-Doppler | — | — | 0.029 ± 0.04 | — |
| RHC-MRI | — | — | 2.38 ± 1.15 | — |
| Heart rate, bpm | | | | |
| RHC-Doppler | 0.81 | <0.0001 | 4.15 ± 4.92 | 0.68 |
| RHC-MRI | 0.75 | 0.0002 | 6.3 ± 4.16 | 0.93 |
| BP, mm Hg, RHC-MRI | | | | |
| SBP | 0.76 | 0.0002 | 11.83 ± 9.94 | 0.67 |
| DBP | 0.49 | 0.04 | 11.89 ± 9.8 | 0.46 |
| MBP | 0.65 | 0.004 | 10.5 ± 9.02 | 0.49 |
| CI, L/min/m², RHC-MRI | 0.69 | 0.0008 | 0.52 ± 0.37 | 0.74 |

Note:
Time differences are in median ±interquartile range.
HR and BP differences are in mean ±SD.
BP: blood pressure,
CI: cardiac index;
DBP: diastolic blood pressure,
MBP: mean blood pressure,
MRI: magnetic resonance imaging,
PA: pulmonary artery,
PVR: pulmonary vascular resistance,
RHC: right heart catheterization,
SBP: systolic blood pressure.

Invasive hemodynamic assessment using RHC revealed higher PA systolic, diastolic, mean, pulse pressures and lower cardiac indices in high PVR group compared to normal PVR group as shown in TABLE 4.

TABLE 4

Invasive hemodynamics.

| Hemodynamic parameter | All (n = 20) | Normal PVR Group, PVR < 2.5 (n = 10) | High PVR Group, PVR ≥ 2.5 (n = 10) |
|---|---|---|---|
| Right atrial mean pressure | 6.6 ± 4.5 | 5.6 ± 2.7 | 7.5 ± 5.8 |
| Pulmonary artery systolic pressure | 44.9 ± 22.3 | 30.9 ± 9.6 | 59 ± 22.7* |
| Pulmonary artery diastolic pressure | 17 ± 9.3 | 12 ± 5.9 | 22 ± 9.5* |
| Pulmonary artery mean pressure | 29.5 ± 13.6 | 21 ± 6.8 | 37.9 ± 13.7* |
| Pulmonary artery pulse pressure | 27.9 ± 15.1 | 18.9 ± 6.6 | 37 ± 15.9* |
| Pulmonary capillary wedge pressure | 12.3 ± 6.6 | 12.7 ± 6.9 | 11.9 ± 6.6 |
| Thermodilution cardiac index, L/min | 3.01 ± 0.7 | 3.32 ± 0.6 | 2.7 ± 0.7* |
| Fick cardiac index, L/min | 3.02 ± 0.8 | 3.42 ± 0.8 | 2.62 ± 0.6* |
| Pulmonary vascular resistance, Woods Units | 3.43 ± 2.9 | 1.34 ± 0.6 | 5.51 ± 2.7* |
| Systemic vascular resistance, dynes.s/cm$^5$ | 1449.1 ± 461.6 | 1257.8 ± 333.3 | 1640.3 ± 507.4 |

Note:
All pressures are in mm Hg, al values mean ± SD,
*p-value <0.05 for normal PVR vs high PVR groups;
PVR: pulmonary vascular resistance CMR derived right ventricular mass index, end-diastolic volume index and mass to volume ratio were higher in high PVR group compared to normal PVR group, as shown in the table below. Left ventricular ejection fraction was, on average, preserved in both groups, shown in TABLE 5.

TABLE 5

Right and left ventricular mass, volume and function.

| MRI parameter | All (n = 19) | Normal PVR Group, PVR < 2.5 (n = 9) | High PVR Group, PVR ≥ 2.5 (n = 10) |
|---|---|---|---|
| Right ventricular ejection fraction, % | 52 ± 12 | 57 ± 13 | 48 ± 11 |
| Right ventricular stroke volume index, ml | 37 ± 11 | 36 ± 12 | 38 ± 12 |
| Right ventricular end-diastolic volume index, ml/m$^2$ | 73 ± 21 | 64 ± 12 | 81 ± 25 |
| Right ventricular mass index, g/m$^2$ | 24 ± 12 | 17 ± 5 | 30 ± 14* |
| Right ventricular mass/volume ratio | 0.3 ± 0.1 | 0.3 ± 0.1 | 0.4 ± 0.1* |
| Left ventricular ejection fraction, % | 60 ± 15 | 61 ± 19 | 59 ± 12 |
| Left ventricular stroke volume index, ml | 38 ± 10 | 42 ± 11 | 35 ± 7 |
| Left ventricular end-diastolic volume index, ml/m$^2$ | 68 ± 24 | 75 ± 29 | 61 ± 18 |
| Left ventricular mass index, g/m$^2$ | 57 ± 18 | 58 ± 19 | 55 ± 18 |

Note:
All values mean ± SD,
*p-value < 0.05 for normal PVR vs high PVR groups.
MRI: magnetic resonance imaging;
PVR: pulmonary vascular resistance Several other traditional measures of PA stiffness were studied. Compliance, capacitance, distensibility of PA were lower and elastic modulus was higher in high PVR group compared to low PVR group, as shown in TABLE 6.

TABLE 6

Measures of pulmonary arterial stiffness.

| Pulmonary artery stiffness parameter | All (n = 20) | Normal PVR Group, PVR < 2.5 (n = 10) | High PVR Group, PVR > 2.5 (n = 10) |
|---|---|---|---|
| Pulmonary to aortic diameter ratio | 0.94 ± 0.2 | 0.87 ± 0.2 | 1 ± 0.2 |
| Pulsatility, % | 21.7 ± 11.6 | 26.2 ± 14.3 | 17.3 ± 6.1 |
| Compliance, mm$^2$/mm Hg | 5.9 ± 3.4 | 7.7 ± 3.5 | 4.2 ± 2.2* |
| Capacitance, cm$^3$/mm Hg | 3.5 ± 2.1 | 4.7 ± 1.9 | 2.3 ± 1.4* |
| Distensibility, %/mm Hg | 1.1 ± 0.9 | 1.5 ± 1.1 | 0.6 ± 0.3* |
| Elastic modulus, mm Hg | 155.8 ± 93.5 | 94.5 ± 54.4 | 217.1 ± 84.5* |
| Stiffness index | 5.8 ± 3.9 | 4.9 ± 2.6 | 6.8 ± 4.7 |

Note: All values mean ± SD,
*p-value <0.05 for normal PVR vs high PVR groups.
PA: pulmonary artery,
PVR: pulmonary vascular resistance.

Velocity Transfer Function and Invasive Impedance: Mixed model statistical analysis with invasive impedance as outcome variable and VTF and harmonics as predictor variables was conducted. As all harmonics were included in the model, there were multiple observations per patient and, hence, unstructured covariance structure was utilized in the model. There was significant relationship between VTF and invasive impedance for right-sided VTF (proximal RPA to distal RPA, F-ratio 12.34, p-value 0.0023) but not for left sided VTF (MPA to proximal LPA, F-ratio 1.6, p-value 0.22). This relationship between VTF, right and invasive impedance remained significant after adjustment for elevation in PCWP (F ratio=8.08, p=0.01).

Figure 22A:
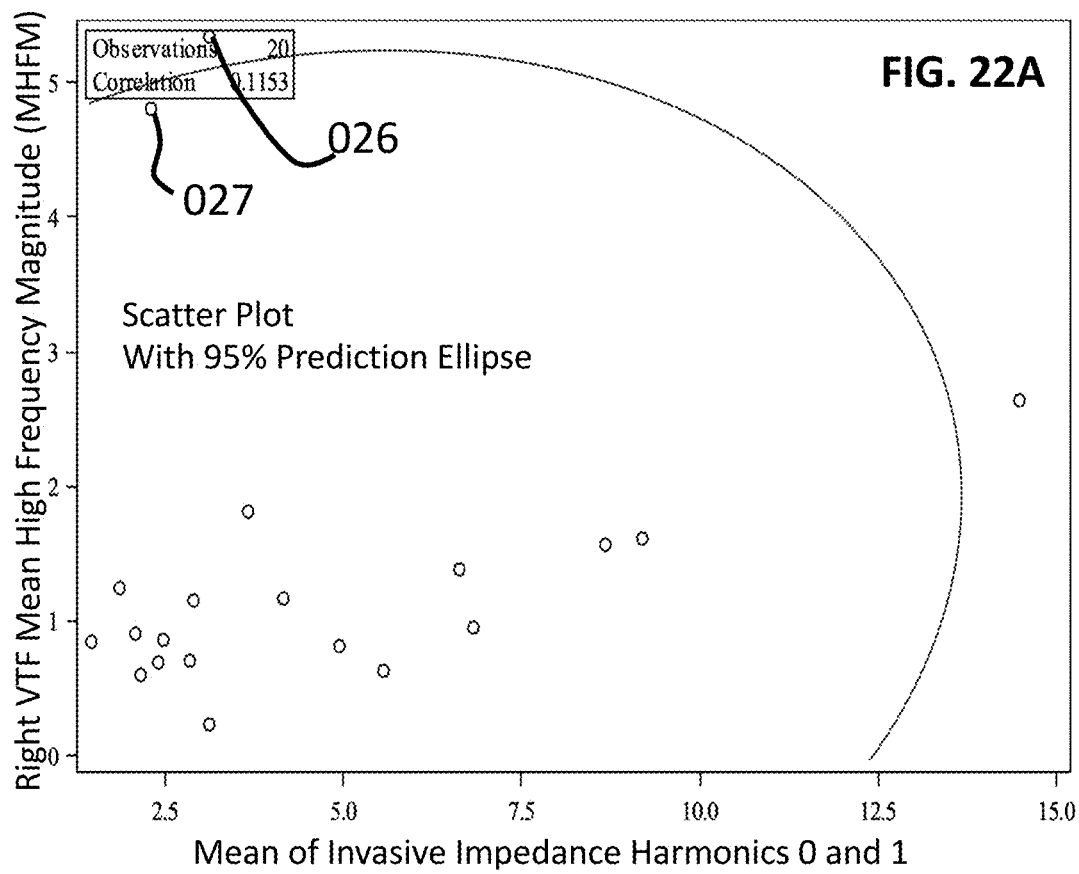
FIGS. 22A and 22B illustrate scatter plots of the mean of invasive impedance harmonics 0-1 and VTF mean high frequency magnitude (MHFM) (average of the magnitudes of harmonics 5 and 6) in the RPA (FIG. 22A); mean of invasive impedance harmonics 0-1 and velocity transfer function MHFM in the LPA (FIG. 22B). 026 and 027 are the 2 'outliers'.
Figure 22B:
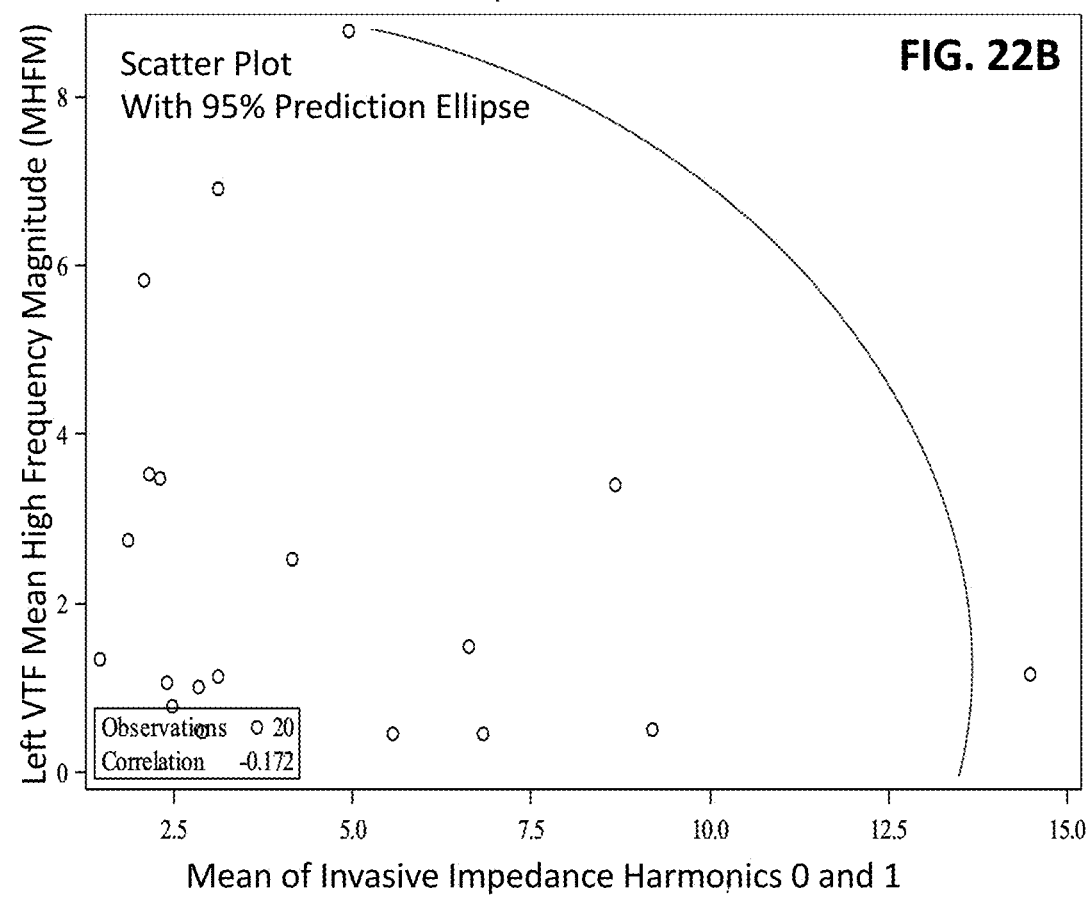
Figure 23:
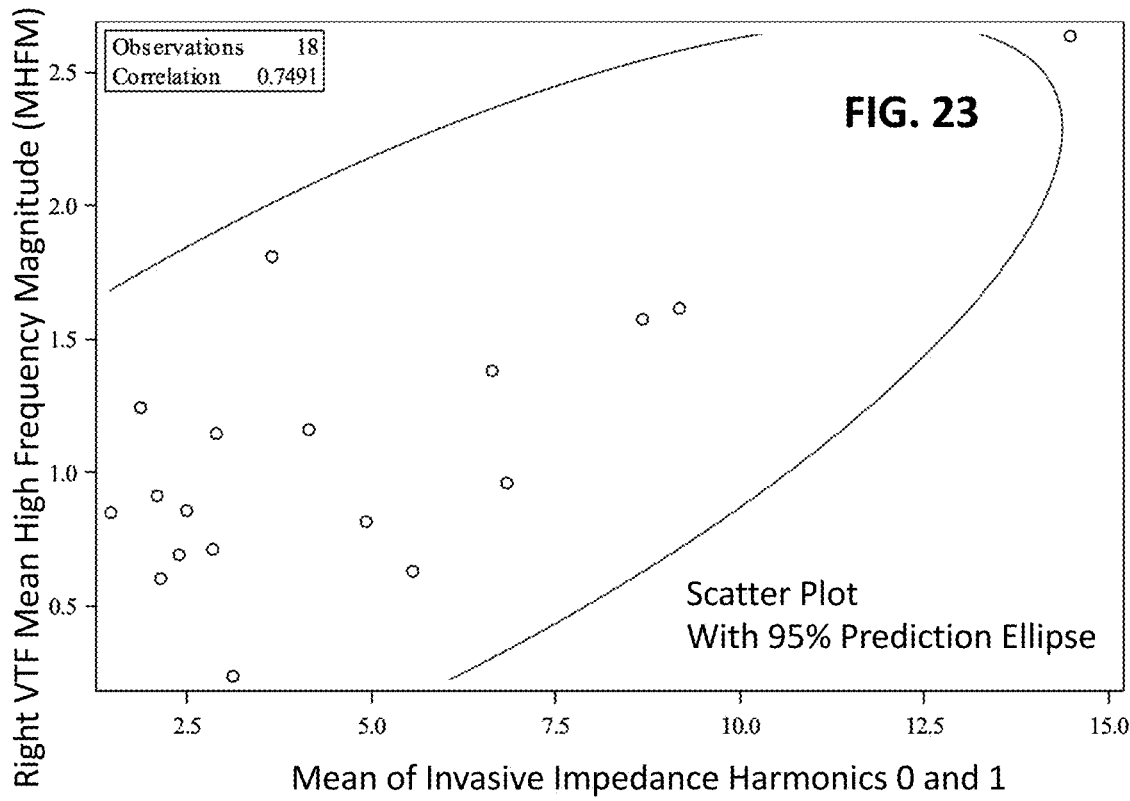
FIG. 23 shows a scatter plot of mean invasive impedance harmonics 0-1 and VTF MHFM in the RPA after removal of two 'outliers'.
Figure 24A:
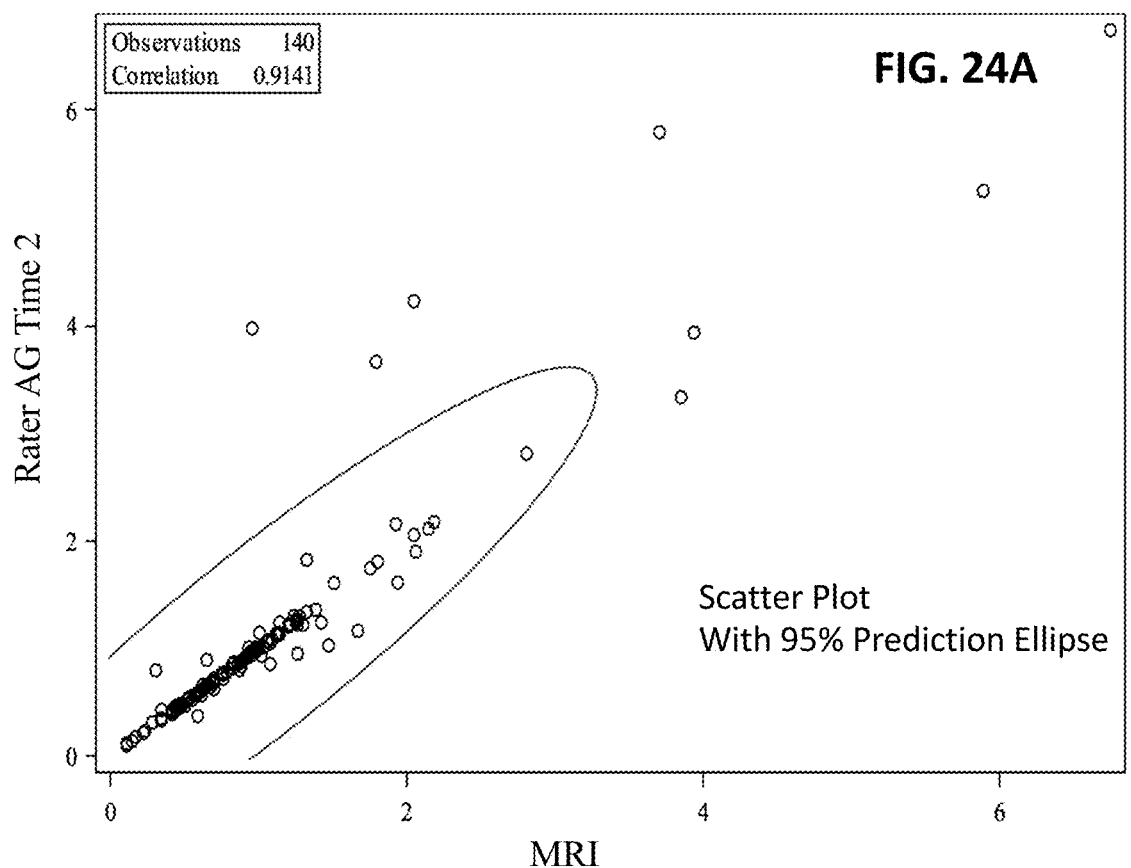
Figure 24B:
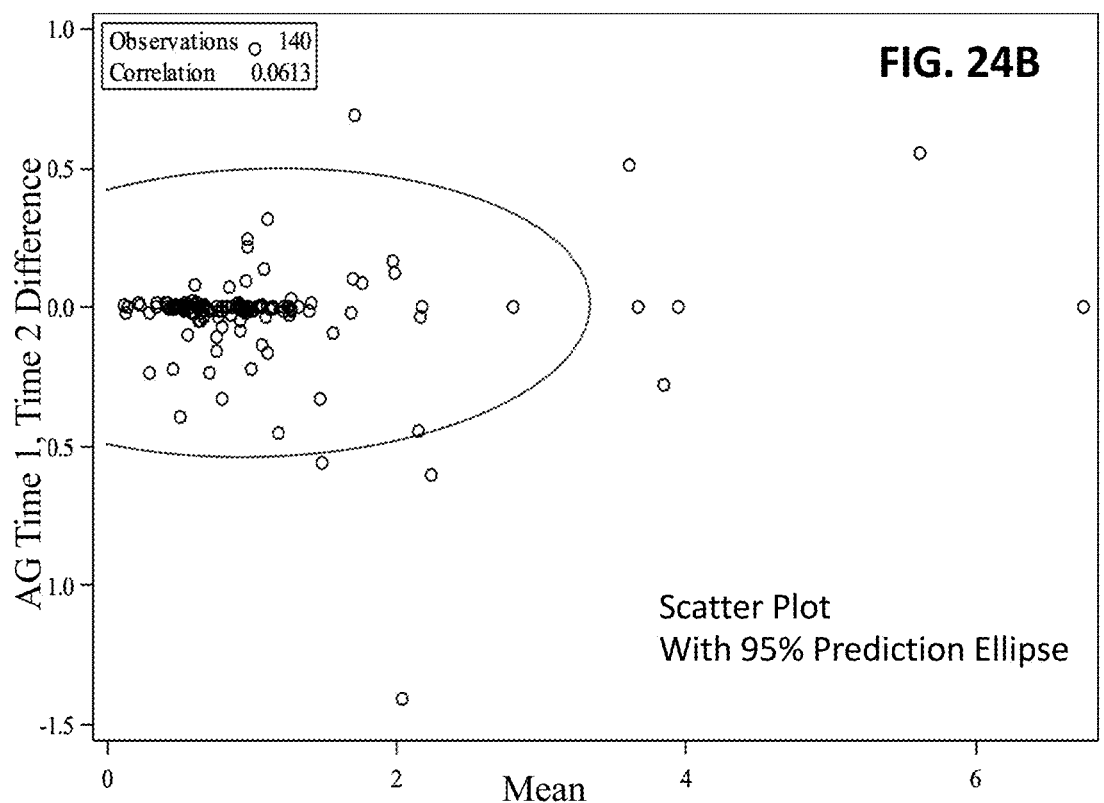
Figure 24C:
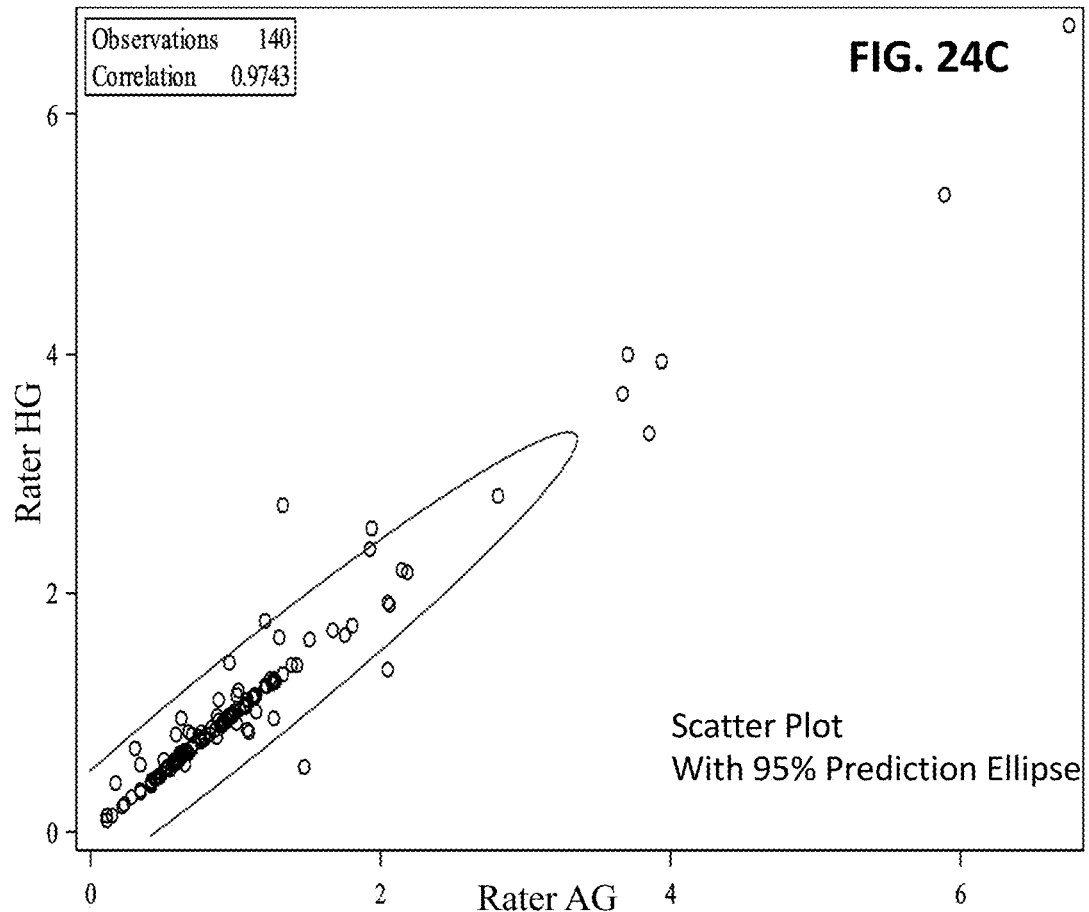

The relationship between VTF and invasive impedance was also evaluated. The mean of 0-1 harmonics of invasive impedance and MHFM (mean of VTF harmonics 5-6) were calculated. On initial investigation, there was no correlation between mean of impedance harmonics 0-1 of invasive impedance and RPA VTF MHFM (Pearson r=0.12, p=0.63) or LPA VTF MHFM (Pearson r=−0.17, p=0.47). The corresponding scatter plots are shown below in FIGS. 22A and 22B. As clearly seen from scatter plot, there is no correlation for mean invasive impedance harmonics 0-1 and LPA VTF MHFM, FIG. 22B. But, on close examination of scatter plot for invasive impedance and RPA VTF MHFM (FIG. 22A). It was found that there appears to be a strong correlation between mean invasive impedance harmonics 0-1and RPA VTF MHFM but this relationship seems to have been influenced by two 'outlier' points (green arrows, FIG. 22A)

with relatively lower mean of 0-1 impedance harmonics and high VTF MHFM. These two 'outliers' corresponded to the patients with normal mean PA pressures and PVR between 2.5-3 (early PA remodeling) where the mean of invasive impedance harmonics 0-1 will be low due to only slightly elevated PVR but due to early PA remodeling, they had large high frequency magnitude of VTF with increased MHFM. With these two 'outliers' removed, there was a significant correlation of VTF MHFM and mean of invasive impedance harmonics 0-1 (Pearson r=0.74, 95% CI=0.42-0.89, p=0.0002, FIG. 23).

Intra- And Inter-Observer Variability. There was high inter- and intra-observer reliability in the mean high frequency magnitude of the VTF shown in TABLE 7 and FIGS. 24A-24D.

TABLE 7

Intra-observer and inter-observer variability in mean high frequency magnitude of velocity transfer function.

| Parameter | Correlation | | Agreement | |
| --- | --- | --- | --- | --- |
| | Intra-Class Correlation Coefficient | 95% CI | Relative bias ± SD | p-value ($\mu_0$: Bias = 0) |
| Intra-observer | 0.93 | 0.84-0.97 | 0.19 ± 0.54 | 0.13 |
| Inter-observer | 0.94 | 0.87-0.98 | 0.048 ± 0.28 | 0.97 |

Relationship with right ventricular structure and function. Invasive impedance showed significant association with RVMI, RVEDVI and RV mass to volume ratio (TABLE 8).

TABLE 8

Assessment of association of right ventricular remodeling with invasive impedance and velocity transfer function.

| Parameter | Invasive Impedance ($Z_{12}$) | | | VTF ($Z_{56}$) | | |
| --- | --- | --- | --- | --- | --- | --- |
| | $R^2$ | F ratio | p | $R^2$ | F ratio | p |
| RV ejection fraction | 0.04 | 0.73 | 0.4 | 0.44 | 13.41 | 0.0019* |
| RV stroke volume index | 0.05 | 0.82 | 0.38 | 0.3 | 7.13 | 0.016* |
| RV mass index | 0.5 | 16.73 | 0.0008* | 0.01 | 0.26 | 0.62 |
| RV end-diastolic volume index | 0.42 | 12.14 | 0.0028* | 0 | 0 | 0.99 |
| RV mass/volume ratio | 0.23 | 5.12 | 0.03* | 0.07 | 1.23 | 0.28 |

Note:
*p-value < 0.05.
RV: right ventricular;
VTF: velocity transfer function.

Figure 28:
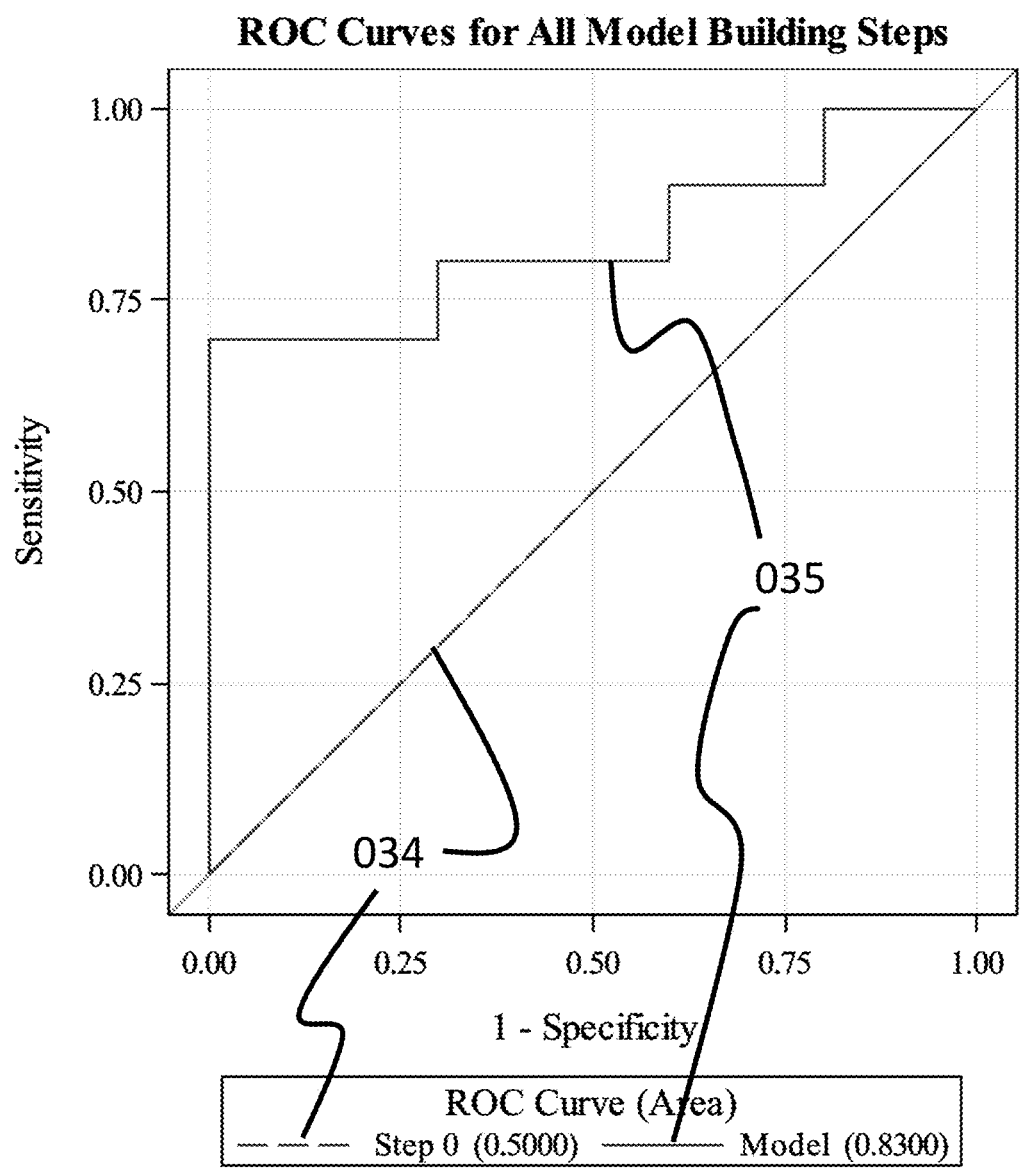
FIG. 28 shows the receiver operative characteristic curve for mean high frequency magnitude of velocity transfer function as a binary classifier for normal versus high pulmonary vascular resistance.
Figure 29:
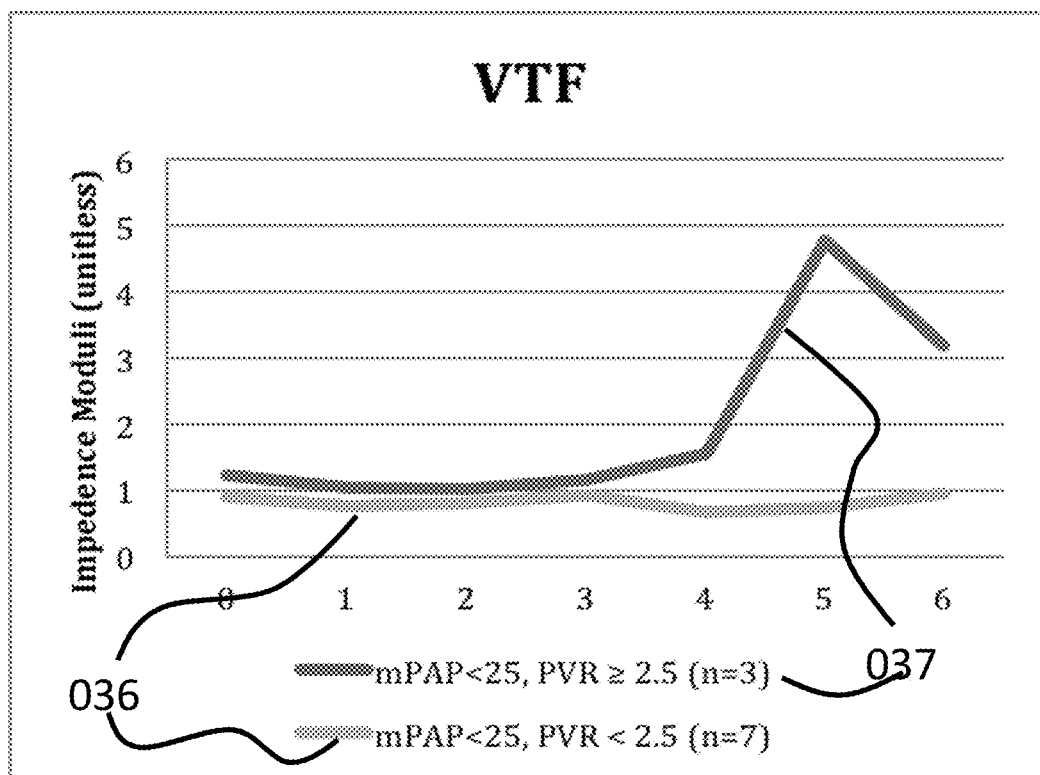
FIG. 29 shows velocity transfer function curves over first six harmonics in patients with normal pulmonary artery pressures with either normal (036) or elevated (037) pulmonary vascular resistance indicative of early pulmonary arterial remodeling.

The VTF also showed significant association with RVEF with RVEF decreasing with increasing MHFM but no association was initially seen with RVMI (TABLE 8 and FIGS. 25A and 25B). Two 'outliers' were noted in the fit curve for the RVMI and MHFM (FIG. 25A, 028, 029). These 2 'outliers' corresponded to the patients with early PA remodeling (normal mean PA pressure with PVR between 2.5-3). They had high impedance but without proportionally increased RVMI likely due to being early in the disease process. After these 2 'outliers' were removed, the VTF showed significant association with RVMI ($R^2=0.32$, F ratio=6.91, p=0.01, FIG. 25B).

In this pilot study, a novel non-invasive assessment of PA impedance using VTF on CMR was proposed and it was shown for the first time that PA impedance can be detected completely non-invasively using VTF. It was demonstrated that the VTF can differentiate between spectrums of imped-ances and can detect patients with early PA mechanical remodeling. It was shown that this detection of PA impedance using VTF is independent of elevation in PCWP. It was also shown that VTF non-invasively evaluated RV-PA coupling with significant association of VTF with RVEF and RVMI. VTF was also robust in its measurement with high intra- and inter-observer agreement on repeated independent measurements of blinded studies.

In this study, there was significant association of invasive impedance with VTF when measured as change in velocity profile from proximal RPA to distal RPA but not from main PA to proximal LPA. This may potentially be due to LPA being short with early branching, thus, leading to inaccuracies in velocity measurements during phase-contrast MRI due to lack of a circular anatomic profile.

Figure 26:
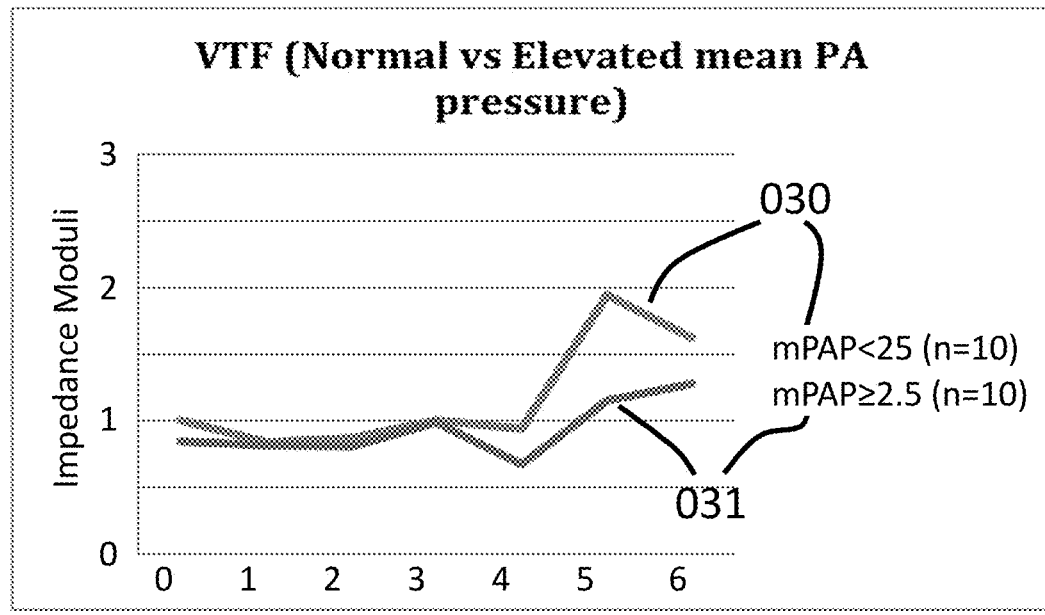
FIG. 26 shows velocity transfer function magnitudes curves over first six harmonics for elevated (031) versus normal (030) mean pulmonary arterial pressure groups.

Of the 20 study patients, 10 had normal PA pressures as defined by mean PA pressure of <25 mm Hg and 10 had normal PVR as defined by PVR<2.5 WU. VTF did not differentiate between normal PA pressure vs elevated PA pressure groups (FIG. 26), p-value for interaction of harmonics with group to predict impedance=0.74) but differentiated between normal PVR vs elevated PVR groups (FIG. 27), p-value for interaction of harmonics with group to predict impedance=0.001).

Figure 27:
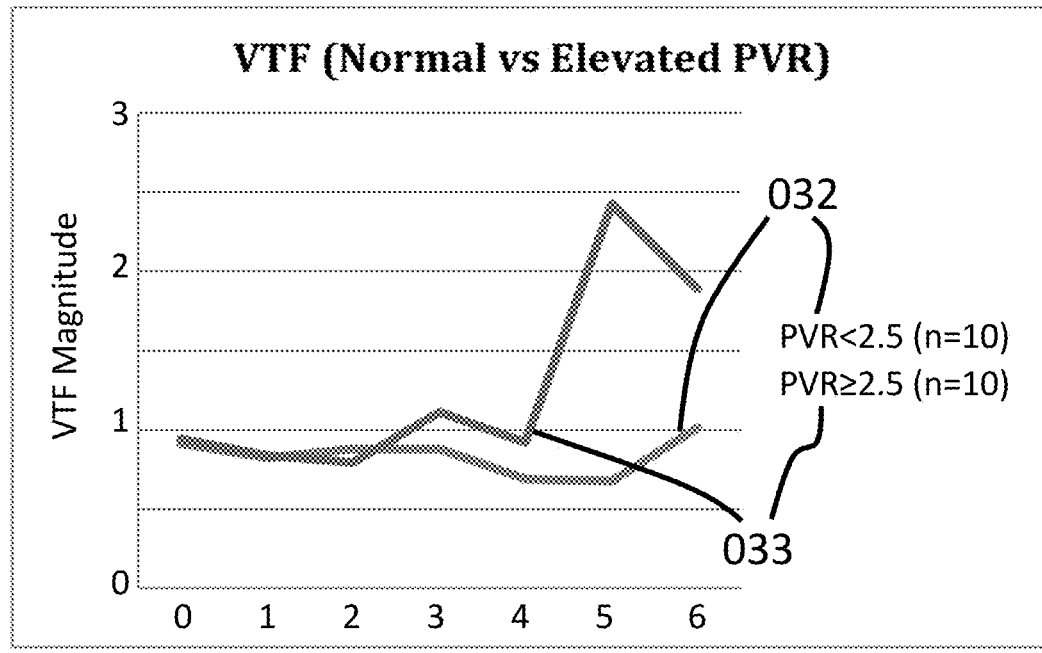
FIG. 27 shows velocity transfer function magnitudes curves over first six harmonics for patients with elevated (033) versus normal (032) pulmonary vascular resistance groups.

Mean high frequency magnitude, MHFM, of 5th and 6th harmonic of VTF was also studied. As seen in FIG. 27, MHFM was higher for high PVR group compared to normal PVR group (2.15±1.64 vs 0.84±0.3 respectively, t9.6=−2.3, p=0.04). On ROC analysis, MHFM showed significant performance capacity of MHFM to differentiate patients with normal PVR from high PVR (FIG. 28, AUC=83%, Chi-square=4.55, p=0.03). This demonstrates the potential of VTF to non-invasively differentiate between patients with normal PVR vs high PVR.

Of the 10 patients with normal mean PA pressure<25 mm Hg, VTF differentiated between those with normal PVR<2.5 (n=7) and those with elevated PVR between 2.5-3 (n=3) as seen in FIG. 29. This indicates the potential of VTF to detect early PA stiffness in patients with otherwise normal PA pressures.

Figure 30:
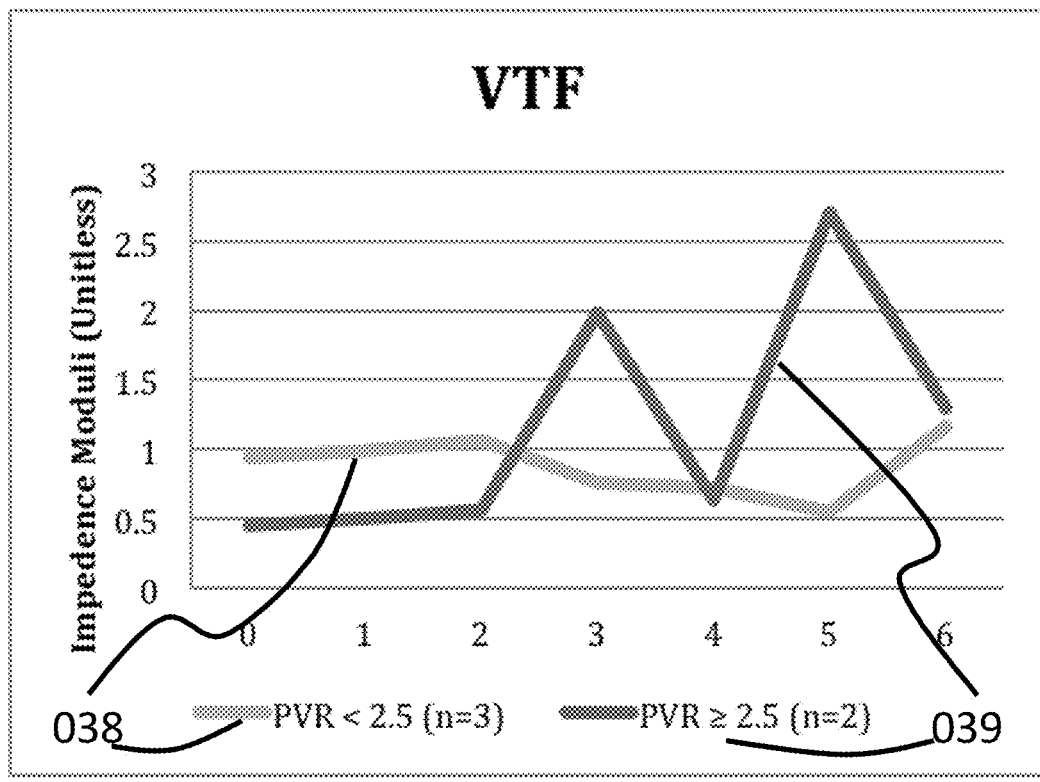
FIG. 30 shows velocity transfer function curves over first six harmonics in patients with elevated pulmonary artery pressures with elevated pulmonary capillary wedge pressures with either normal (038) or elevated (039) pulmonary vascular resistance.

In this study, 5 patients had elevated PCWP. Of these 3 had normal PVR (pulmonary venous hypertension) and 2 had elevated PVR (mixed pulmonary arterial and venous hypertension). VTF differentiated between normal and elevated PVR groups despite elevation in PCWP (FIG. 30). This indicates the potential of VTF to detect PA remodeling irrespective of elevation in PCWP. This can be very useful to study PA impedance and remodeling in patients with chronic left sided heart failure. Of note, although inferential statistics were not calculated for FIG. 29 and FIG. 30 due to small sample sizes in these sub-groups, these are hypothesis generating that should be tested in larger studies.

This study showed that VTF has strong association with invasive impedance. This can also be seen in corresponding invasive impedance and VTF curves of patients with normal and high PVR (FIG. 31A and FIG. 31B) as well as patients with normal mean PA pressure with or without elevated PVR (FIG. 32A and FIG. 32B).

Figure 32A:
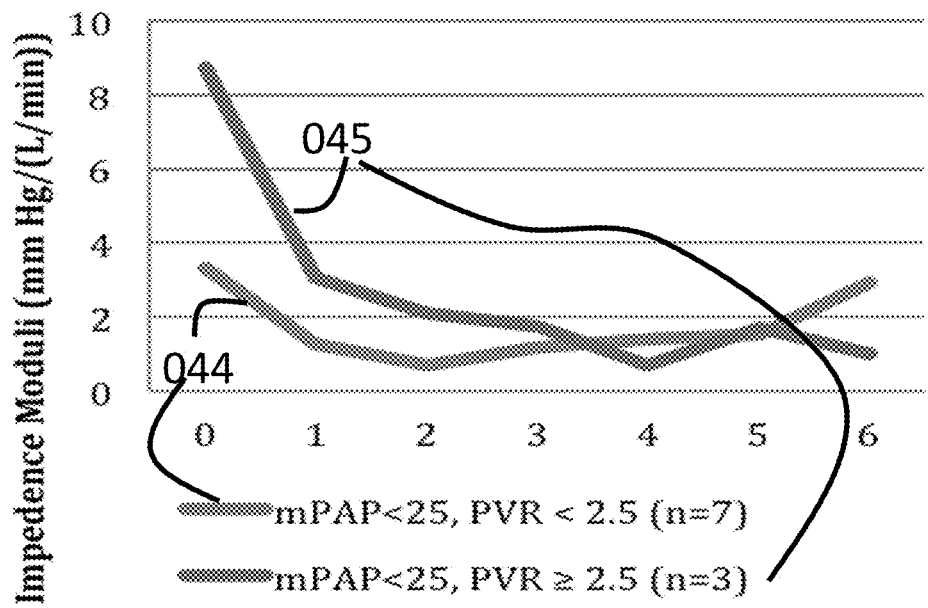
FIGS. 32A and 32B show invasive impedance curves (FIG. 32A) and corresponding velocity transfer function curves (FIG. 32B) over first six harmonics in patients with normal mean pulmonary arterial pressures with either normal (044, 046) or elevated (045, 047) pulmonary vascular resistance.
Figure 32B:
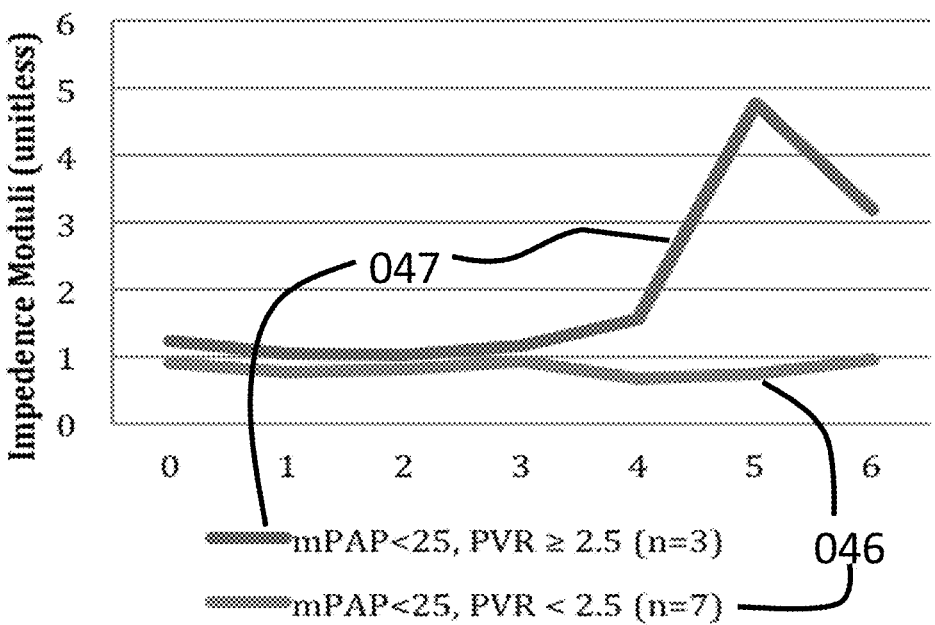

As seen in FIG. 31A, and FIG. 32A, normal invasive impedance curves show a low magnitude at zero harmonic, then rapidly descends down with first minimum magnitude occurring at low harmonics (1 or 2). Impedance magnitude curves of patients with high PVR show high magnitude at zero harmonic, and then slowly descends down with first minimum occurring at later harmonics (3 or 4 or higher). This is the expected behavior of impedance curves (Nichols, W. et al., 2005), lending support to the invasive impedance measurements in this study. Corresponding VTF curves in FIG. 31B and FIG. 32B demonstrate that VTF curves start at similar zero harmonic for patients with normal or high PVR but then show differentiation at higher harmonics (5 or 6) when impedance magnitudes increase in patients with high PVR. For invasive impedance, the pressure and flow curves have different mean values, which reflects as high impedance magnitudes at zero and lower impedance harmonics. In contrast, for VTF, the input (proximal RPA) and output (distal RPA) velocity curves have close to the same mean value, so the zero and lower VTF harmonics are close to 1 before separating at higher harmonics.

Figure 36:
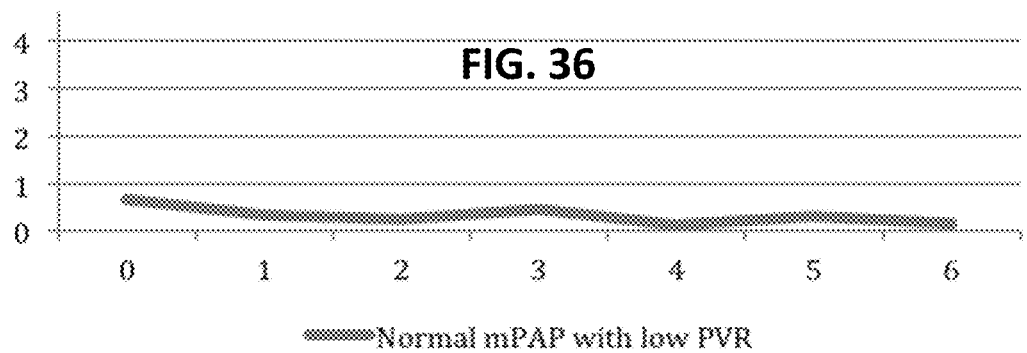
FIG. 36 shows the velocity transfer function curve over first six harmonics of a patient with scleroderma with otherwise no clinical pulmonary hypertension (mean PA pressure of 23 mm Hg), PCWP 12 mm Hg, CO 5.96 L/min, PVR 1.85 WU (normal)
Figure 37:
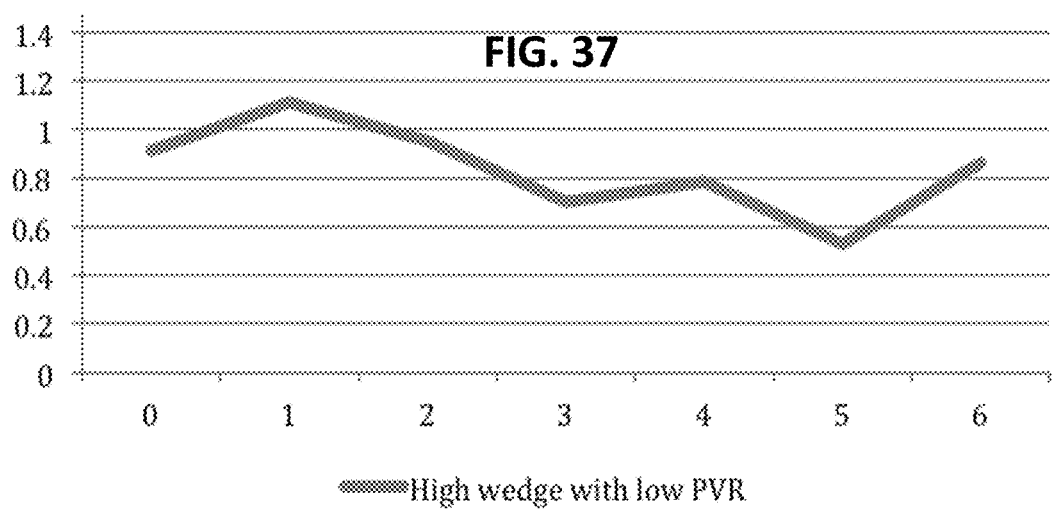
FIG. 37 shows the velocity transfer function curve over first six harmonics of a patient with heart failure with preserved ejection fraction with elevated pulmonary pressures (mean PA pressure of 30 mm Hg) secondary to elevated PCWP 20 mm Hg, CO 9.98 L/min and normal PVR 1.1 WU (pulmonary venous hypertension)
Figure 38:
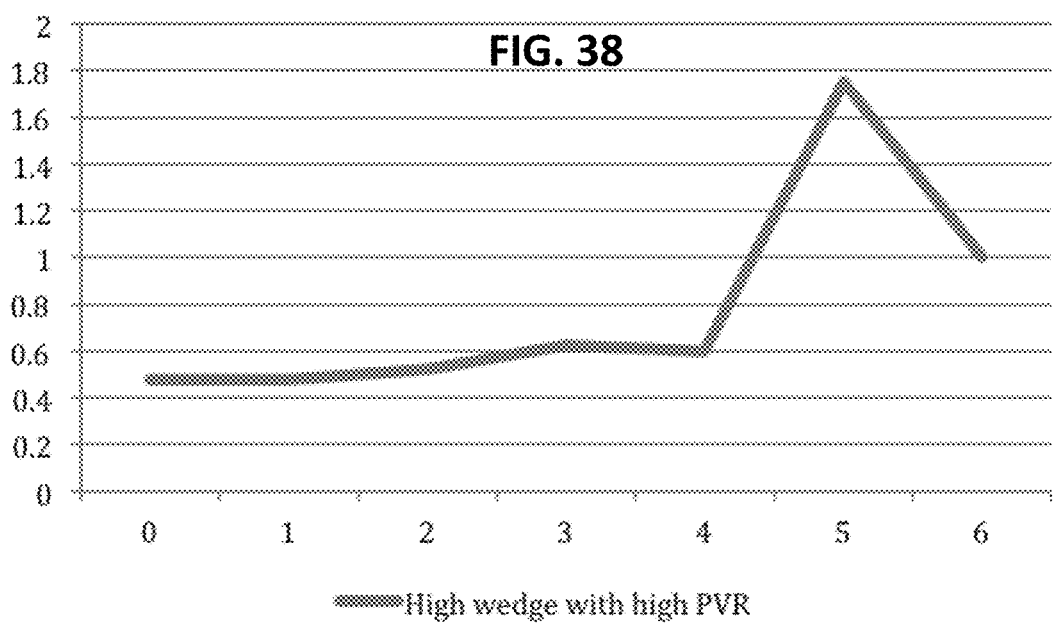
FIG. 38 shows the velocity transfer function curve over first six harmonics of a patient with restrictive cardiomyopathy due to cardiac amyloidosis with elevated pulmonary pressures (mean PA pressure of 36 mm Hg) secondary to elevated PCWP 23 mm Hg, CO 3.64 L/min and elevated PVR 3.575 WU (mixed pulmonary venous and arterial hypertension)

Individual Patient Studies: The following individual patient examples from this study illustrates the potential ability of VTF as a powerful tool to non-invasively detect early pulmonary arterial remodeling (PVR between 2.5 to 3, FIG. 33, FIG. 34) from normal PVR<2.5 (FIG. 35, FIG. 36) in patients with otherwise normal mean PA pressures. It also demonstrates the potential ability of VTF to distinguish high vs normal pulmonary vascular resistance despite elevated PCWP (FIG. 37, FIG. 38) in individual patients.

Strengths of VTF: This study demonstrates for the first time the feasibility of VTF as a non-invasive highly reliable method of assessing pulmonary arterial impedance and assessment of RV-PA axis. It is reproducible, relatively inexpensive, requires no ionizing radiation, takes less than 10 minutes to obtain using phase-contrast CMR study which can also be extended to include cine-CMR in the same session for assessment of RV structure and function.

VTF is a surrogate of invasive impedance and not an exact measure of invasive impedance. Invasive impedance is the ratio of magnitudes of pressure by flow in frequency domain where as VTF is the ratio of magnitudes of output velocity profile to input velocity profile in frequency domain. This study demonstrated that VTF as an accurate and reliable non-invasive surrogate of PA impedance and thus, can be used as a screening tool before more expensive or invasive tests are considered. In this study, invasive impedance was measured using hybrid acquisition of pressure data from RHC and flow data from Doppler echocardiography. Although completely invasive assessment of PA impedance is feasible and was utilized in older studies in animals (Milnor, W., et al., 1966; Caro, C. G., et al., 1961; Patel, D. J., et al., 1963; Bergel, D. H., et al., 1965; van den Bos, G. C., et al., 1982; Maggiorini, M., et al., 1998; Santana, D. B., et al., 2005; Greenwald, S. E., et al., 1985; Leather, H. A., et al., 2002) and humans (Milnor, W. R., et al., 1969; Wilcox, B. R., et al., 1980; Murgo, J. P., et al., 1984; Kussmaul, W. G., et al., 1988; Chen, Y. T., et al., 1990; Kussmaul, W. G., et al., 1992) but most recent human studies (Hunter, K. S., et al., 2008; Huez, S., et al., 2004) on PA impedance have used the hybrid acquisition due to practicality and relative low expense. In addition, the behavior of invasive impedance in current study's patients (FIG. 31A and FIG. 32A) matched expected impedance curve behavior (Nichols, W., et al., 2005). Another limitation is use of fluid-filled catheter for acquisition of invasive PA pressure measurements during RHC as opposed to use of high-fidelity catheters which are not available for routine clinical practice and are expensive to use. The other limitation of this study is non-simultaneous acquisition of invasive impedance (RHC-Doppler) and VTF (CMR). There are very few hybrid MRI-RHC suites in the world. Thus, for all practical purposes, the only way currently to acquire RHC and MRI data in a given patient is sequential. In this study, in order to minimize hemodynamic alterations between RHC and MRI acquisition, all studies in a given patient were obtained on the same day as close to each other as feasible (TABLE 3). There was strong intra-class agreement of hemodynamic parameters of HR, BP and CI at time of RHC and MRI (TABLE 3). In addition, as impedance analysis is in frequency domain, rather than time domain, it is unlikely that the differences in hemodynamic parameters in physiologic range will adversely affect the impedance measurements between RHC and MRI.

In this study, the following conclusions were reached. It was demonstrated, for the first time, the feasibility of using non-invasive VTF as a surrogate for invasive PA impedance measurement. It was demonstrated that the VTF can differentiate between spectrums of impedance magnitudes and can detect patients with early PA mechanical remodeling. It showed the potential of VTF in detecting PA impedance independent of elevation in PCWP. VTF non-invasively evaluated RV-PA coupling with significant association with RVEF and RVMI. VTF was also robust in its measurement with high intra- and inter-observer agreement on repeated independent measurements of blinded studies.

However, this was a pilot study. VTF would need to be validated in larger studies. Utility and robustness of VTF would need to be evaluated in special patient populations. Some of these would be patients with: chronic obstructive lung disease, heart failure with preserved ejection fraction, heart failure with reduced ejection fraction, connective tissue disorders. Relationship of VTF to clinical outcomes needs to be assessed in longitudinal studies. Serial changes in VTF with disease progression or with therapy need to be investigated in longitudinal studies.

Clinical Example 3

In this embodiment, a single heartbeat pressure waveform was measured with an invasive left heart catheter at a point distal to a suspected stenosis in a coronary artery (earliest time point) and considered to be a reference waveform. The catheter was then pulled back through the area of suspected stenosis yielding a series of single heartbeat waveforms (later time points). A series of PTFs $S_{P_i}(f)$ were then computed using the aforementioned formula:

This procedure was performed on two patients with coronary artery disease. A sequence $$S_{P_i}(f) = \frac{P_{distal_i}(f)}{P_{proximal}(f)}$$

of PTFs were calculated as described above, and the PTF harmonics versus time are plotted in FIGS. 39A-39C, and 40A-40C.

Figure 39A:
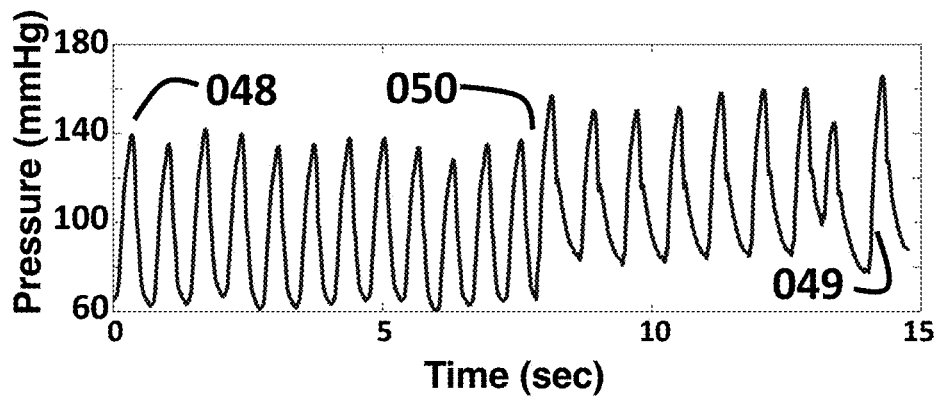
FIGS. 39A-39C respectively show a series of pressure waves as catheter tip is pulled back from a distal point (048) across a stenosis to a proximal point (049); the largest magnitude harmonic (harmonic 3) of the PTF versus time, where the change in harmonic 3 when the catheter crosses the stenosis near 050 in FIG. 39A and 051 in FIG. 39B; and harmonics 0 (052, which is also the FFR), 1 (053), 2 (054) and 4 (055), which exhibit little change as the catheter tip crosses the stenosis.
Figure 39B:
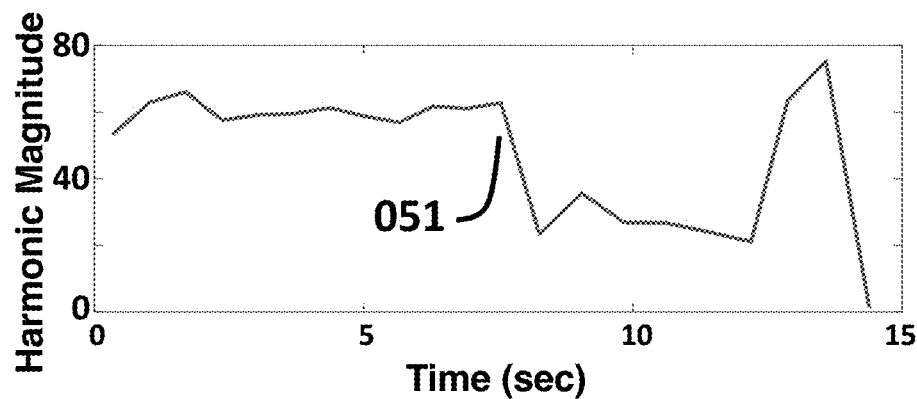
Figure 39C:
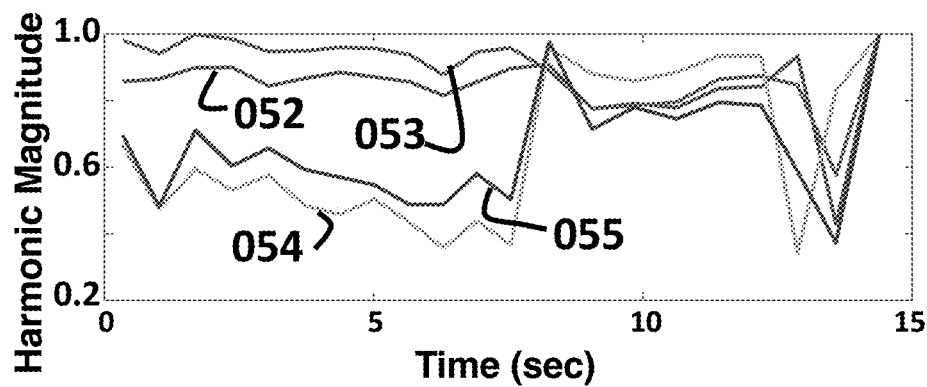

FIGS. 39A-39C respectively show a series of pressure waves as catheter tip is pulled back from distal point (048) across a stenosis to proximal point (049); the largest magnitude harmonic (harmonic 3) of the PTF versus time (note the change in harmonic 3 (051) when the catheter crosses the stenosis near 050 in FIG. 39A and 051 in FIG. 39B); and harmonics 0 (052, i.e. FFR), 1 (053), 2 (054) and 4 (055), which exhibit little change as the catheter tip crosses the stenosis.

Figure 40A:
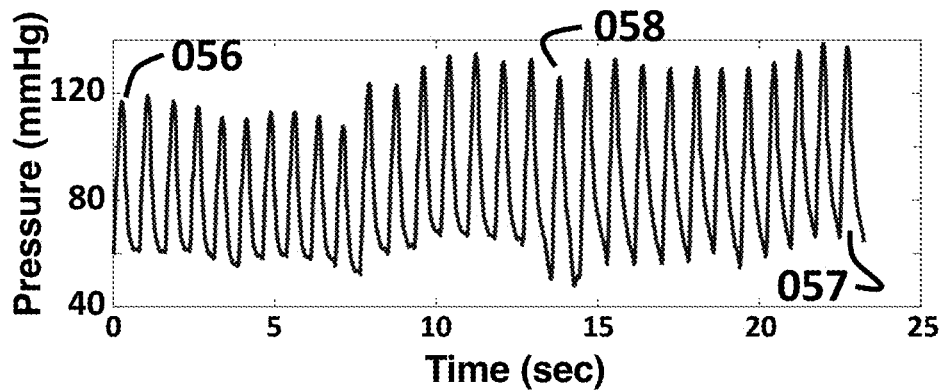
FIGS. 40A-40C respectively show a series of pressure waves as catheter tip is pulled back from a distal point (056) across a stenosis to a proximal point (057); the largest magnitude harmonic (harmonic 3) of the PTF versus time, where the change in harmonic 3 when the catheter crosses the stenosis near 058 in FIG. 40A and 059 in FIG. 40B; and harmonics 0 (060, which is also the FFR), 1 (061), 2 (062) and 4 (063), which exhibit little change as the catheter tip crosses the stenosis.
Figure 40B:
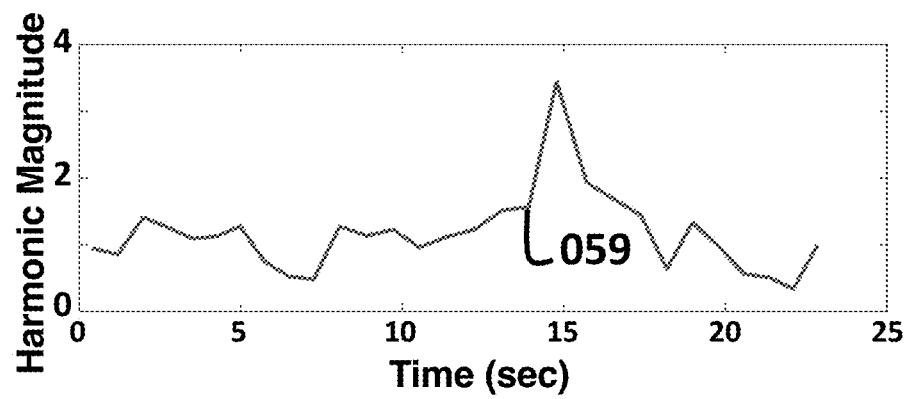
Figure 40C:
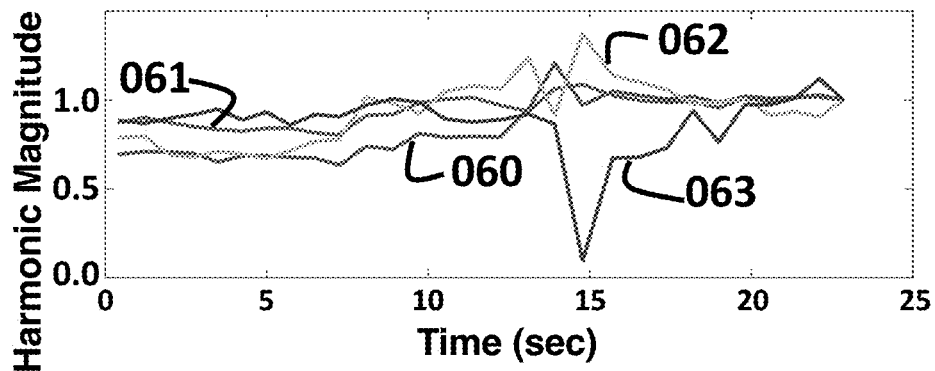

FIGS. 40A-40C respectively show a series of pressure waves as catheter tip is pulled back from distal point (056) across a stenosis to proximal point (057); the largest magnitude harmonic (harmonic 3) of the PTF versus time (note the change in harmonic 3 when the catheter crosses the stenosis near 058 in FIG. 40A and 059 in FIG. 40B); and harmonics 0 (060, i.e. FFR), 1 (061), 2 (062) and 4 (063), which exhibit little change as the catheter tip crosses the stenosis;

In both cases harmonic 3 was orders of magnitude larger than the other harmonics, and changes in harmonic 3 correlated with the location and severity of the stenosis. Changes in harmonic 3 represent changes in the pressure waveform due to interaction with vessel wall, which has increased stiffness at the stenosis. The PTF provides a comprehensive assessment of the stenosis in a vessel because the zero harmonic is equivalent to the FFR and higher harmonics reflect the impact of flowing blood and its interaction with vessel wall.

Clinical Example 4

Pulmonary hypertension (PH) is an important prognostic indicator in patients with chronic obstructive pulmonary disease (COPD), however PH in these patients is typically mild-to-moderate severity and invasive testing is not typically utilized (Minai O A, et al., 2010). Though echocardiography can be used to screen for PH, it has limited accuracy in measuring pulmonary artery (PA) pressure and often hindered by window limitations in COPD patients (Arcasoy S M, et al., 2003). Cardiovascular magnetic resonance (CMR) does not have window limitations and can accurately evaluate the right ventricular (RV) and PA function. Therefore, there is a growing interest in the use of CMR for the diagnosis and management of PH, including patients with lung diseases. Recently, it has been validated a novel non-invasive CMR derived parameter that, similar to impedance, reflects pulsatile and resistive properties of the PA (Gupta A, et al., 2018). This approach relies on the principle that compliant PA vessel walls cause changes in the velocity profile as it travels through the PA over the cardiac cycle. The frequency-dependent relationship between the input and output velocity profiles is described by a velocity transfer function (VTF), which is the relationship between the frequency spectra of input and output velocity. In suspected PH patients who underwent right heart catheterization, it was found that VTF correlates with invasive PA impedance and the mean high frequency modulus (MHFM) of VTF correlates with the pulmonary vascular resistance (PVR) and RV remodeling. Moreover, MHFM>1 accurately predicted an increased PVR. It is hypothesized that elevated MHFM of VTF, reflecting increased PVR and pulmonary vascular disease, would be associated with reduced exercise capacity measured by 6-minute walk distance (6MWD) in a COPD cohort.

Materials and methods.

Figure 41A:
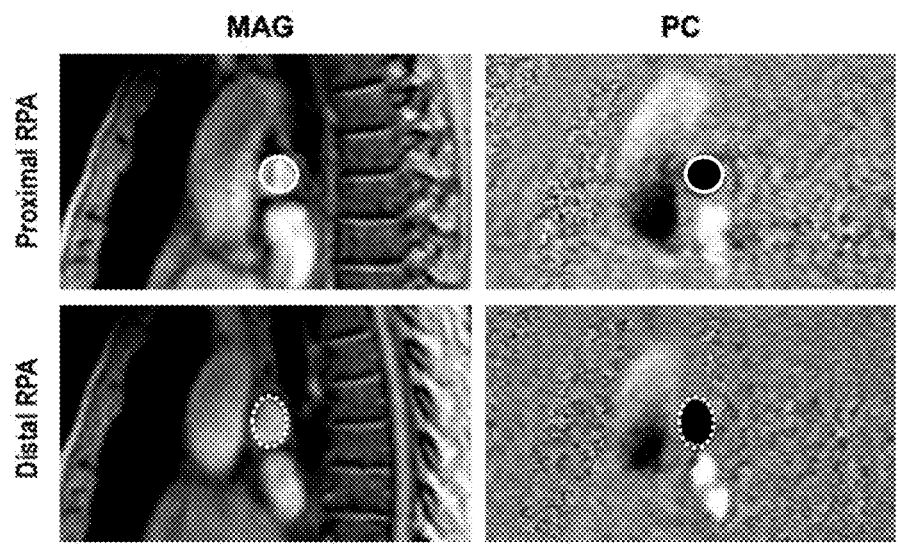
FIGS. 41A-41C show MHFM of VTF in COPD, where
Figure 41B:
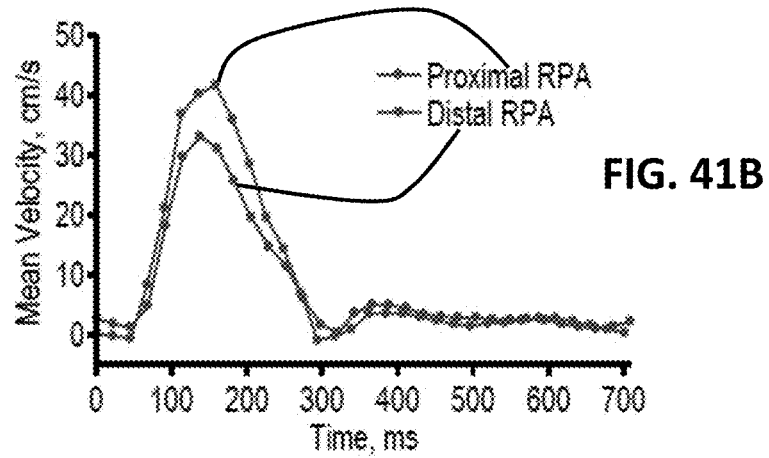
Figure 41C:
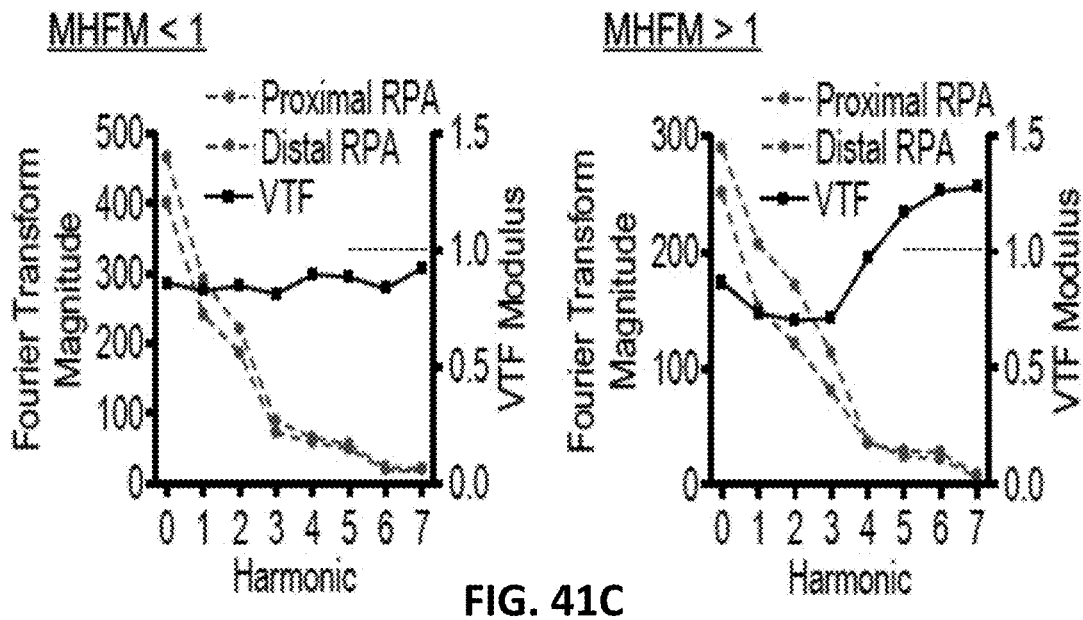

Participants with COPD and mild-to-moderate airflow obstruction based on Global Initiative for Chronic Obstructive Lung Disease (GOLD) spirometric staging were prospectively recruited (Vogelmeier C F, et al., 2017). Participants were excluded if they had known cardiac or pulmonary vascular disease. This study was approved by the University of Alabama at Birmingham Institutional Review Board and all participants gave written informed consent (IRB #110809004). Participants completed clinical evaluation (Vogelmeier C F, et al., 2017), post-bronchodilator spirometry with measurement of percent predicted forced expiratory volume in 1-second (FEV1%, herein FEV stands for forced expiratory volume) (Miller M R, et al., 2005), quantitative emphysema as measured by chest computed tomography (CT) (Muller N L, et al., 1988), 6-minute walk test, and CMR study. The 6-minute walk test was performed as a part of clinical care, prior to the CMR, and was conducted one time according to ATS standards (ATS statement: guidelines for the six-minute walk test., 2002) on room air without stops for a rest. All participants completed the 6-minute walk test. CMR was performed using a 1.5-T magnetic resonance scanner (GE Signa, Milwaukee, Wis.) optimized for cardiac applications. Phase-contrast CMR technique (ECG gated breath-hold fast gradient echo (FGRE) sequence) was used for flow measurements in the right PA (RPA) (FIG. 41A). Typical parameters were as follows: field of view, 40 cm; scan matrix, 256×128; encoding velocity, 150 cm/s; number of excitations, 1; flip angle, 15°; repetition/echo times, 7.8/3.2 ms; band width, ±31.25 kHz; 8 views per segment. Thirty-two phases were reconstructed. Contours were drawn and mean velocity-time profiles over a cardiac cycle were computed using CAAS MR Flow 1.2 (Pie Medical Imaging, Netherland) and exported to MATLAB 2015a for VTF and MHFM of VTF calculation as previously described (FIG. 41B and FIG. 41C) (Gupta A, et al., 2018). Cine CMR (ECG gated breath-hold balanced steady state fast processing (bSSFP) sequence) was used for measurements of RV and left ventricular (LV) structure and function using endocardial and epicardial contours manually traced on short-axis cine images acquired near end-diastole and end-systole as previously described (Gupta A, et al., 2018). CMR measurements were blinded to the 6-minute walk test, clinical evaluation, spirometry and CT measurements. Participants were categorized into MHFM>1 and MHFM<1 groups. Clinical, cardiopulmonary functional indices, LV and RV function was compared between MHFM groups using Mann-Whitney-U test. The strength of association between MHFM of VTF and 6MWD was studied using Spearman's rank correlation coefficient (ρ). Linear regression models adjusted for FEV1% were used to measure associations between 6MWD and elevated MHFM (MHFM>1). All analyses were performed in SPSS v.23 and P<0.05 indicated statistical significance.

Figure 42A:
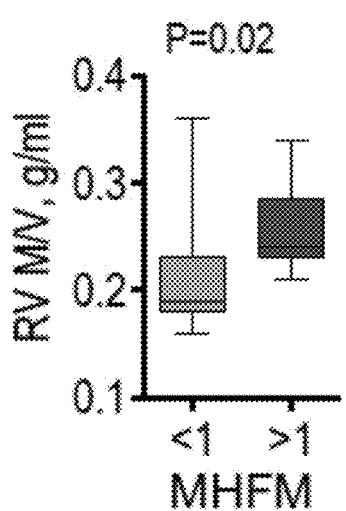
FIGS. 42A-42E show cardiac and pulmonary measurements in COPD with high (>1) and low (<1) MHFM of VTF, where high and low MHFM groups had different RVM/V (FIG. 42A), RVM/LVM (FIG. 42B), but did not differ by RVMI (FIG. 42C), FEV1 PP (FIG. 42D), or emphysema (FIG. 42E); yet, 6MWD was lower in the high MHFM group (FIG. 42F); and the abbreviations used herein include: MHFM, mean high frequency modulus; VTF, velocity transfer function; RVM/V, right ventricular mass to volume ratio; RVM/LVM, ratio of right and left ventricular mass; RVMI, right ventricular mass index; FEV1 PP, percent predicted forced expiratory volume in 1-second; and 6MWD, 6-minute walk distance.
Figure 42B:
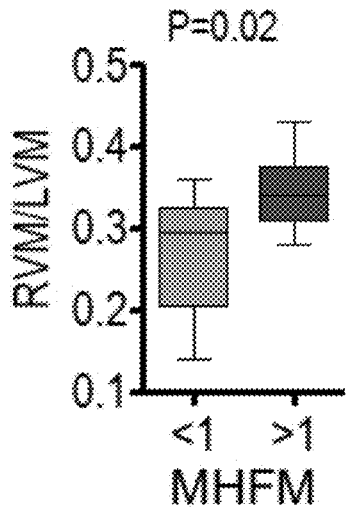
Figure 42C:
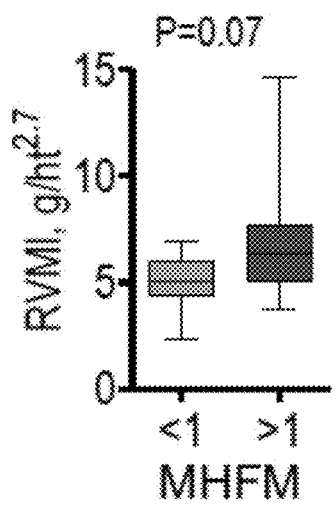

The 21 patients recruited were 60±9 (mean±standard deviation) years old, 62% male, with an FEV1% of 61±27% and LV ejection fraction of 62±8%. Twelve participants had MHFM<1 (median 0.85 [interquartile range (IQR) 0.75-0.90]) and nine participants had MHFM>1 (1.23 [IQR 1.10-1.67]). In MHFM>1 group, RV ejection fraction (51% [IQR 47%-64%]), end diastolic volume index (50 [IQR 45-68] ml/m2), and stroke volume (33 [IQR 23-38] ml/m2) were similar to that in MFHM<1 group (57% [IQR 54%-61%] (P=0.70), 59 [IQR 56-67] ml/m2 (P=0.25), and 34 [IQR 32-36] ml/m2 (P=0.76), respectively). LV ejection fraction, LV volumes, and cardiac index were also similar between MHFM groups (P>0.1). The MHFM>1 group had a larger RV mass/volume ratio and RV/LV mass ratio (FIGS. 42A-42C). There were no between-group differences in LV mass index and LV mass to volume ratio (P>0.1).

Figure 42D:
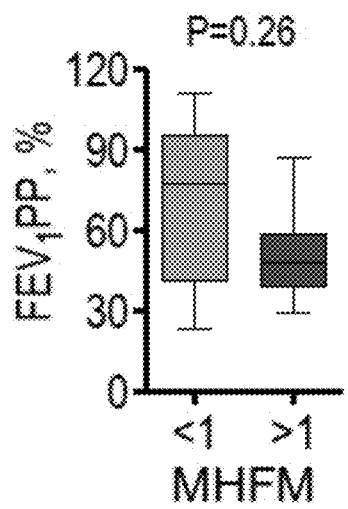
Figure 42E:
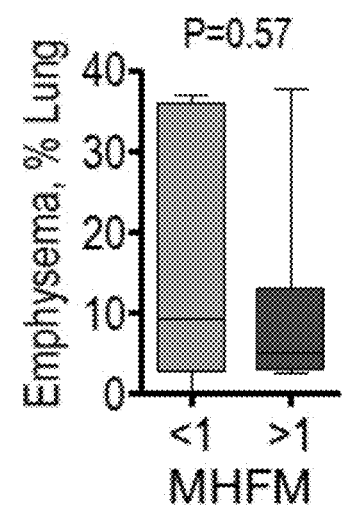
Figure 42F:
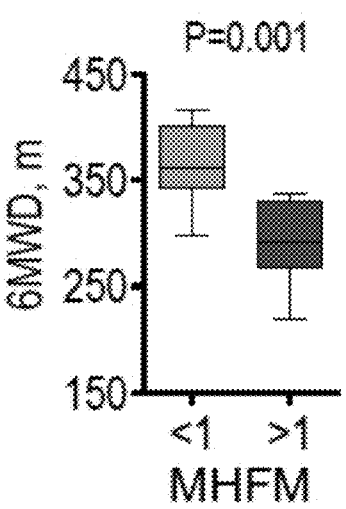

MHFM>1 group had numerically worse clinical symptoms (though not reaching statistical significance) assessed by modified Medical Research Council (mMRC) Dyspnea Scale (3 [IQR 2-3] vs. 2 [IQR 0-3] in MHFM<1 group, P=0.25) and severity of airflow limitation by Global Initiative for Chronic Obstructive Lung Disease (GOLD) criteria for GOLD stage (3 [IQR 2-3] vs. 1.5 [IQR 0.5-3] in MHFM<1 group, P=0.28). FEV1% was not statistically different in the MHFM>1 versus MHFM<1 group (P=0.26, FIG. 42D). There were no between group differences in quantitative emphysema (FIG. 42E). In the entire cohort, results of the 6-minute walk test were markedly worse than expected for healthy population, 7 with 6MWD of 337 [IQR 296-385] meters. There was a significant inverse correlation between 6MWD and MHFM of VTF (Spearman's p=−0.56, P=0.009). The MHFM>1 group had shorter 6MWD (293 [IQR 268-329] meters vs. 361 [IQR 343-402] meters in MHFM<1 group, P=0.0012) (FIG. 42F). In a linear regression model adjusting for FEV1%, MHFM>1 accounted for a −60.7±16.7 meter shorter 6MWD (P=0.002).

Data from this pilot study show that measuring the MHFM of VTF may have utility in assessing pulmonary vascular disease in COPD. These findings suggest that MHFM of VTF>1 is associated with signs of RV remodeling as well as impaired exercise tolerance as measured by 6MWD in COPD. These observed differences occurred in the absence of differences in LV structure or function, percent of emphysema or FEV1%. Importantly, it is found that the association between MHFM>1 and reduced 6MWD was independent from FEV1%, suggesting that it has additional value beyond lung function in identifying impaired exercise function in COPD. Together, MHFM>1 and FEV1% accounted for 53.5% of the variability in 6MWD. This study was limited by the small sample size and the lack of invasive hemodynamic assessments, though it mirrored usual clinical care of these patients with COPD, since they usually do not undergo right-sided heart catheterization due to the lack of therapeutic options specific for this population. These findings should be validated in larger COPD cohorts.

In this proof of concept study, patients with severe COPD were excluded as the interest is in whether VTF could be used as a tool to identify the pulmonary vascular abnormalities in the absence of severe parenchymal destruction and chronic hypoxia. The investigation of VTF utility in more advanced lung disease is therefore needed. In this study, VTF was measured only under resting conditions, yet the measurement of VTF with exercise may provide additional diagnostic power, and thus should be evaluated in future studies. Because VTF in the RPA was measured, any heterogeneity in vessel impedance and stiffness in the pulmonary vasculature could be missed by this technique. Further research is needed to utilize VTF in the main PA and left PA for assessment of heterogeneity in vessel impedance.

In conclusion, measurement of the mean high-frequency modulus (MHFM) of the velocity transfer function (VTF), a non-invasive marker of PVR, is associated with impairments in exercise capacity and RV remodeling in a cohort of mild-to-moderate COPD. Therefore, VTF could be a valuable tool for characterizing pulmonary vascular disease among COPD patients. However, further research is required for accurate evaluation of the VTF application in COPD.

Clinical Example 5

4D flow is an emerging phase contrast MRI technique for time-resolved 3D imaging (4D=3D+time) of moving tissue velocities in the chest—most often blood flow in the arteries. In 4D flow, all three components of velocity are measured as opposed to 2D phase contrast imaging, which typically only measures velocities through the image plane. Typically, in 4D flow, the entire chest is imaged in a single 10-15 min scan with an isotropic spatial resolution of ~2-3 mm and a temporal resolution of 20 timeframes per cycle. Electrocardiogram gating is used, but the patient is allowed to breathe freely during the scan.

The most common application of 4D flow is imaging blood flow in the heart and arteries. The advantage of 4D flow for these applications is that blood flow in the entire chest is measured in a single data set. After the scan, analysts can retroactively measure the time-resolved flow at multiple locations. With 2D phase contrast imaging, the locations must be selected prior to imaging and a separate scan must be acquired for each location. Also, typically, only through-plane velocity is measured in 2D phase contrast imaging. 4D flow measures velocities in all three directions.

The cardiac left ventricle and the aorta are the most common organs studied with 4D flow, but researchers have recently used 4D flow to study blood flow in the pulmonary arteries in patients with pulmonary hypertension, but these studies were limited to single-point flow parameters such as statistics of blood velocity and flow, area, relative area change, and pulse-wave velocity.

An attempt was made to perform velocity transfer function (VTF) analysis from 4D flow data. The velocities measured from 4D flow have been shown to be consistent with velocities measured from traditional 2D phase contrast imaging (Sieren, et al 2019). The advantages of 4D flow for VTF analysis are as follows:

Single versus multiple acquisitions. In a standard, 2D, VTF acquisition, the following five phase contrast imaging planes are prescribed by the scanner operator and acquired with five different breath holds: main pulmonary artery (MPA); right pulmonary artery (RPA) proximal to the bifurcation; RPA distal to the bifurcation; left pulmonary artery (LPA) proximal to the bifurcation; LPA distal to the bifurcation. Many PH and COPD patients may have problems holding their breath, and the hemodynamic conditions may change from breath hold to breath hold. In 4D flow, a single free-breathing scan is acquired over 10-15 minutes. While, the patient's hemodynamics can change over the 10-15 scan time, they are in a stable state relative to taking five breath holds over approximately the same amount of time.

Slice positioning accuracy. In 2D phase contrast imaging, each slice must be individually prescribed based on different views of the patient. If a plane is incorrectly positioned or oriented, this error is usually not discovered until after the scan is complete and the patient has left the scanner. The most common problems are slice that are not perpendicular to the artery and inconsistent spacing between the proximal and distal imaging planes. With 4D flow, the location and orientation of analysis planes is done after data acquisition and can be adjusted and optimized as much as needed with no penalty. This makes it easier to prescribe analysis planes that are perpendicular to the artery and achieve a consistent spacing between analysis planes.

Ability to perform continuous analysis. With 2D phase contrast imaging, VTF analysis is limited to flow between the five imaging planes acquired during the scan. With 4D flow, VTF can be easily measured between a large number of planes. This capability makes a continuous analysis of pulmonary arterial stiffness possible. For example, a single plane could be placed in the MPA and then a series of planes could be placed, say 1.5 mm apart, from the MPA location to the bifurcation and along the RPA. VTF stiffness parameters could be computed between the first MPA plane and each subsequent RPA yielding a continuous measurement of stiffness from the MPA to the distal RPA. A similar analysis could be performed on the LPA. This analysis could yield new insights into the pathology of diseases like COPD, which can have substantial differences in stiffness in different parts of the pulmonary arterial tree.

Demonstration of Continuous Analysis.

Image Acquisition: A healthy human volunteer was imaged on a General Electric (GE) 1.5 Tesla Optima MR450w MRI scanner (GE Healthcare, Chicago, Ill.) with a 4D flow sequence acquired in an axial orientation. Scanning parameters were as follows: TR/TE=4.3/2.3 ms, Flip angle=8 degrees, 4 averages, bandwidth=5448.3 Hertz/ pixel, VENC=160 cm/s, 180×180 scan matrix, field of view=267×267 mm. 88 slices were acquired with a slice thickness of 4 mm and 2 mm between slices. 20 cardiac phases were reconstructed with an average heart rate of 63 beats per minute, which resulted in 47.6 ms between phases.

Computing Velocity vs Time Curves from 4D Flow Data: The 4D flow data was read into a custom software package written in Matlab (Mathworks, Inc, Natick, Mass.). The phase contrast velocities were corrected for background phase errors using the technique in (Walker et al JMRI 1993). This software allowed the user to specify an arbitrary point in space at a particular cardiac phase in the 4D flow data and compute a streamline from that point to a distal point in the downstream direction. The streamline points were spaced 1.48 mm apart in arc length. At each point on the streamline, the velocity component tangential to the streamline was computed by taking the median of the tangential velocities in a cylinder oriented tangentially to the streamline with a diameter of 8 mm and a thickness of 7.5 mm. The tangential velocity was computed for each point on the streamline at each cardiac phase to produce a set of velocity versus time curves.

Figure 43:
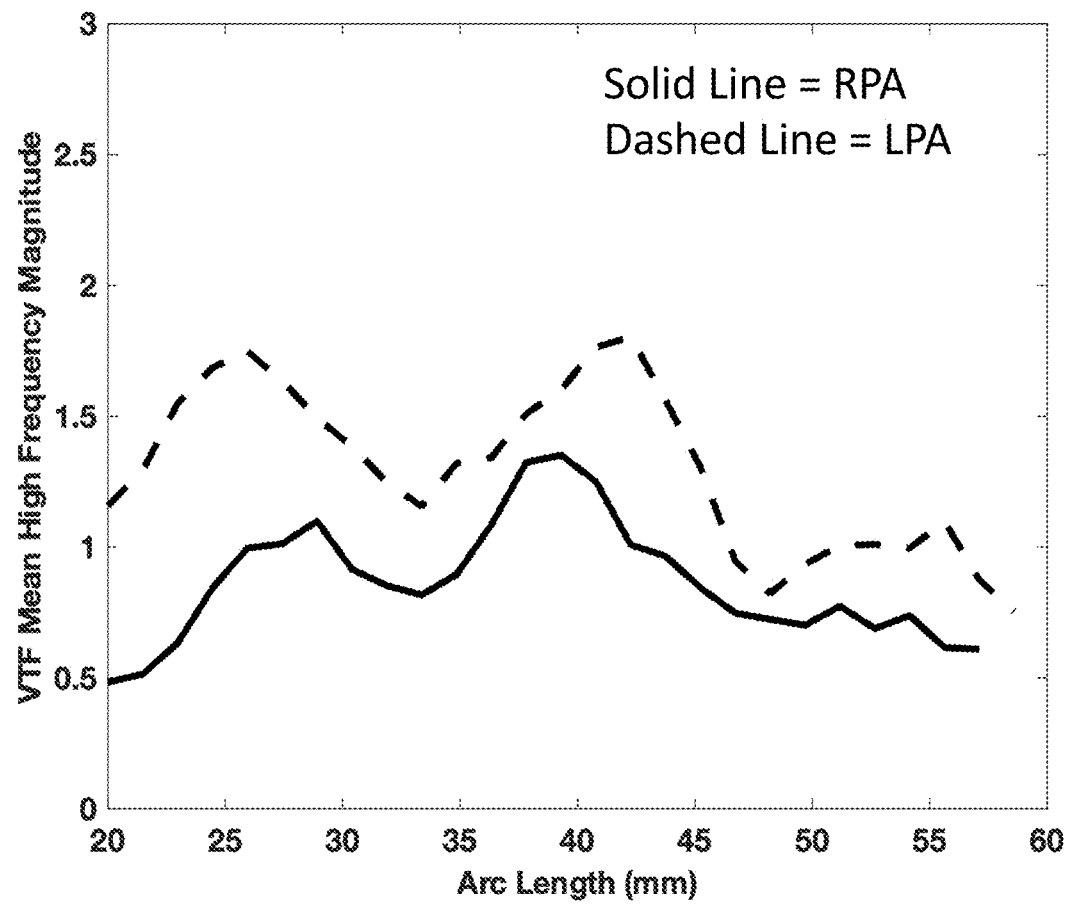
FIG. 43 shows the resulting VTF MHFM versus streamline arc length from the MPA point to the distal RPA point (solid line) and a similar plot from the MPA to the distal LPA (dashed line) in the same volunteer.

VTF Analysis: The above procedure was used to compute velocity vs time curves along a streamline from a point in the MPA to a point in the distal RPA. The velocity vs time curve at the first point on the streamline (in the MPA) was used as the proximal velocity vs time curve and the velocity versus time curve at the point 40 mm in arc length downstream from the first point was used as the distal velocity versus time curve. The VTF MHFM was then computed. The VTF MHFM was assigned to the spatial point halfway between the proximal and distal points, which, in this case, is 20 mm. The next point on the streamline was set as the proximal point and the above procedure was repeated until the distal point was beyond the last streamline point. FIG. 43 shows the resulting VTF MHFM versus streamline arc length from the MPA point to the distal RPA point (solid line) and a similar plot from the MPA to the distal LPA (dashed line) in the same volunteer. Since this is healthy volunteer with no suspicion of PH, the VTF MHFMs are close together and close to 1.0.

REFERENCES

1. Nichols, W. and M. O'Rourke, *McDonald's Blood Flow in Arteries*. 5th ed. 2005, London: Hodder Arnold.
2. Milnor, W., D. Bergel, and J. Bargainer, *Hydraulic power associated with pulmonary blood flow and its relation to heart rate*. Circ Res., 1966. 19(3): p. 467-80.
3. Milnor, W. R., et al., *Pulmonary Arterial Pulse Wave Velocity and Impedance in Man*. Circulation Research, 1969. 25(6): p. 637-649.
4. Yin, F., *Ventricular/Vascular Coupling. Clinical, physiological and engineering aspects*. 1987, New York: Springer-Verlag.
5. Hunter, K. S., et al., *Pulmonary vascular input impedance is a combined measure of pulmonary vascular resistance and stiffness and predicts clinical outcomes better than pulmonary vascular resistance alone in pediatric patients with pulmonary hypertension*. Am Heart J, 2008. 155(1): p. 166-74.
6. Caro, C. G. and D. D. Mc, *The relation of pulsatile pressure and flow in the pulmonary vascular bed*. J Physiol, 1961. 157: p. 426-53.
7. Patel, D. J., F. M. Defreitas, and D. L. Fry, *Hydraulic input impedance to aorta and pulmonary artery in dogs*. J Appl Physiol, 1963. 18: p. 134-40.
8. Bergel, D. H. and W. R. Milnor, *Pulmonary Vascular Impedance in the Dog*. Circ Res, 1965. 16: p. 401-15.
9. van den Bos, G. C., N. Westerhof, and O. S. Randall, *Pulse wave reflection: can it explain the differences between systemic and pulmonary pressure and flow waves? A study in dogs*. Circ Res, 1982. 51(4): p. 479-85.
10. Maggiorini, M., et al., *Effects of pulmonary embolism on pulmonary vascular impedance in dogs and minipigs*. J Appl Physiol (1985), 1998. 84(3): p. 815-21.
11. Santana, D. B., et al., *Pulmonary artery smooth muscle activation attenuates arterial dysfunction during acute pulmonary hypertension*. J Appl Physiol (1985), 2005. 98(2): p. 605-13.
12. Greenwald, S. E., R. J. Johnson, and S. G. Haworth, *Pulmonary vascular input impedance in the newborn and infant pig*. Cardiovasc Res, 1985. 19(1): p. 44-50.
13. Leather, H. A., et al., *Effects of vasopressin on right ventricular function in an experimental model of acute pulmonary hypertension*. Crit Care Med, 2002. 30(11): p. 2548-52.
14. Wilcox, B. R. and C. L. Lucas, *Pulmonary input impedance in children with left-right shunt*. J Surg Res, 1980. 29(1): p. 40-9.
15. Murgo, J. P. and N. Westerhof, *Input impedance of the pulmonary arterial system in normal man. Effects of respiration and comparison to systemic impedance*. Circ Res, 1984. 54(6): p. 666-73.
16. Kussmaul, W. G., J. M. Wieland, and W. K. Laskey, *Pressure-flow relations in the pulmonary artery during myocardial ischaemia: implications for right ventricular function in coronary disease*. Cardiovasc Res, 1988. 22(9): p. 627-38.
17. Chen, Y. T., et al., *Aortic and pulmonary input impedance in patients with cor pulmonale*. Jpn Heart J, 1990. 31(5): p. 619-29.
18. Kussmaul, W. G., 3rd, et al., *Effects of pacing tachycardia and balloon valvuloplasty on pulmonary artery impedance and hydraulic power in mitral stenosis*. Circulation, 1992. 86(6): p. 1770-9.
19. Huez, S., et al., *Feasibility of routine pulmonary arterial impedance measurements in pulmonary hypertension*. Chest, 2004. 125(6): p. 2121-8.
20. Minai O A, Chaouat A, Adnot S. Pulmonary hypertension in COPD: epidemiology, significance, and management: pulmonary vascular disease: the global perspective. Chest. 2010; 137(6 Suppl):39S-51S.

21. Arcasoy S M, Christie J D, Ferrari V A, et al. Echocardiographic assessment of pulmonary hypertension in patients with advanced lung disease. *American journal of respiratory and critical care medicine.* 2003; 167(5):735-740.
22. Gupta A, Sharifov O F, Lloyd S G, et al. Novel Non-Invasive Assessment of Pulmonary Arterial Stiffness Using Velocity Transfer Function. *J Am Heart Assoc.* 2018; 7:e009459.
23. Vogelmeier C F, Criner G J, Martinez F J, et al. Global Strategy for the Diagnosis, Management, and Prevention of Chronic Obstructive Lung Disease 2017 Report. GOLD Executive Summary. *American journal of respiratory and critical care medicine.* 2017; 195(5):557-582.
24. Miller M R, Hankinson J, Brusasco V, et al. Standardisation of spirometry. *The European respiratory journal.* 2005; 26(2):319-338.
25. Muller N L, Staples C A, Miller R R, Abboud R T. "Density mask". An objective method to quantitate emphysema using computed tomography. *Chest.* 1988; 94(4):782-787.
26. ATS statement: guidelines for the six-minute walk test. ATS Committee on Proficiency Standards for Clinical Pulmonary Function Laboratories. *American journal of respiratory and critical care medicine.* 2002; 166(1): 111-117.
27. Markl M, Frydrychowicz A, Kozerke S, Hope M, Wieben O. 4 D flow MRI. J Magn Reson Imaging. 2012; 36(5):1015-1036. doi:10.1002/jmri.23632
28. Walker P G, Cranney G B, Scheidegger M B, Waseleski G, Pohost G M, Yoganathan A P. Semiautomated method for noise reduction and background phase error correction in MR phase velocity data. *J Magn Reson Imaging.* 1993 May-Jun.; 3(3):521-30. PubMed PMID: 8324312.

The invention claimed is:

1. An information processing method, applied to a processing device and for evaluating physiological properties of a segment of a blood vessel in a subject, the information processing method comprising:
 acquiring measurement data comprising a series of sequences of measurements, wherein the series of sequences of measurements comprises at least two sequences of measurements, and are acquired, by means of a measuring device without using any contrast agent and at different time points in at least one cardiac cycle of the subject, respectively and correspondingly at a series of points along a centerline within the segment of the blood vessel, wherein each of the series of sequences of measurements contains blood velocity information or blood pressure information;
 generating a series of profiles from the series of sequences of measurements respectively and correspondingly, wherein each of the series of profiles is a velocity profile or a pressure profile; and
 evaluating physiological properties of at least one selected subsegment within the segment of the blood vessel, each between two of the series of points comprising a first end point and a second end point along a blood flow direction, comprising:
  calculating a transfer function corresponding to each of the at least one selected subsegment, wherein the transfer function is configured to generate an output waveform given an input waveform, using a waveform corresponding to a profile for the first end point and a waveform corresponding to a profile for the second end point as the input waveform and the output waveform respectively, wherein the transfer function is not implemented in a time domain, wherein the transfer function is implemented in a frequency domain, and is calculated as:

$$SM(f)=Moutput(f)/Minput(f);$$

where f is frequency, Moutput(f) is the output waveform, and Minput(f) is the input waveform; and
  determining a physiological property of the blood vessel corresponding to the each of the at least one selected subsegment based on the transfer function.

2. The information processing method according to claim 1, wherein each of the series of sequences of measurements contains blood velocity information, and each of the input waveform and the output waveform is a blood velocity waveform, wherein the transfer function is a velocity transfer function (VTF), calculated based on formula:

$$Sv(f)=Voutput(f)/Vinput(f);$$

where Voutput(f) is the output waveform, and Vinput(f) is the input waveform.

3. The information processing method according to claim 1, wherein each of the series of sequences of measurements contains blood pressure information, each of the input waveform and the output waveform is a blood pressure waveform, and the transfer function is a pressure transfer function (PTF), calculated based on formula:

$$Sp(f)=Poutput(f)/Pinput(f);$$

where Poutput(f) is the output waveform, and Pinput(f) is the input waveform.

4. The information processing method according to claim 1, wherein each of the series of sequences of measurements is acquired in synchronization to the subject's electrocardiogram signal and at equally spaced time points in the at least one cardiac cycle.

5. The information processing method according to claim 1, wherein each of the at least one cardiac cycle comprises a total of at least 20 time points.

6. The information processing method according to claim 1, wherein:
 the measuring device comprises at least one of a catheter, a tonometric device, or a fitness wristband capable of measuring blood pressure; and
 each of the series of sequences of measurements contains blood pressure information.

7. The information processing method according to claim 1, wherein the determining a physiological property of the blood vessel corresponding to the each of the at least one selected subsegment based on the transfer function comprises:
 decomposing the input waveform and the output waveform into a series of
first harmonic components and a series of second harmonic components respectively, wherein the series of first harmonic components and the series of second harmonic components correspond to one another at each harmonic number;
 forming a series of transfer function harmonics, each obtained by dividing each second harmonic magnitude by a corresponding first harmonic magnitude; and
 determining the physiological property of the blood vessel corresponding to the each of the at least one selected subsegment based on one, or a linear combination, of the series of transfer function harmonics.

8. The information processing method according to claim 7, wherein the determining the physiological property of the blood vessel corresponding to the each of the at least one selected subsegment based on one, or a linear combination, of the series of transfer function harmonics comprises:

calculating an average of a magnitude of each of the series of transfer function harmonics with a harmonic number being 5 or higher, to thereby obtain a mean high frequency magnitude (MHFM) for the transfer function; and determining the physiological property of the blood vessel corresponding to the each of the at least one selected subsegment based on the MHFM.

9. The information processing method according to claim 8, wherein the blood vessel is a pulmonary artery, and the segment of the blood vessel is at least one of:

a segment between a main pulmonary artery (MPA) and a right pulmonary artery (RPA) proximal to a bifurcation;

a segment between the MPA and a left pulmonary artery (LPA) proximal to the bifurcation;

a segment between the RPA proximal and distal to the bifurcation; or a segment between the LPA proximal and distal to the bifurcation.

10. The information processing method according to claim 9, further comprising:

determining that the subject has a disease of interest if the subject has MHFM at least 20% higher than a matched population of subjects absent of the disease of interest, wherein the disease of interest is pulmonary hypertension (PH) or chronic obstructive pulmonary disease (COPD).

11. The information processing method according to claim 1, wherein:

the measuring device comprises at least one of a magnetic resonance imaging (MRI) device, a Doppler ultrasound device, or a catheter; and each of the series of sequences of measurements contains blood velocity information.

12. The information processing method according to claim 11, wherein the measuring device comprises a magnetic resonance imaging (MRI) scanner, and each of the series of sequences of measurements is acquired through phase contrast MRI imaging.

13. The information processing method according to claim 12, wherein at least two of the series of sequences of measurements are acquired through separate 2D phase contrast MRI scans, each scan performed with a prescribed phase contrast imaging plane.

14. The information processing method according to claim 12, wherein each of the series of sequences of measurements is acquired without prescribing any phase contrast imaging plane when performing the phase contrast MRI imaging.

15. The information processing method according to claim 14, wherein all of the series of sequences of measurements are acquired through one single free-breathing 4D flow MRI scan.

16. The information processing method according to claim 15, wherein a number of the at least one selected subsegment is at least 2.

17. A processing device for evaluating physiological properties of a segment of a blood vessel in a subject, comprising:

a data acquisition module, configured to acquire measurement data of the segment of the blood vessel, wherein the measurement data comprises a series of sequences of measurements, the series of sequences of measurements comprises at least two sequences of measurements, and are acquired, by means of a measuring device without using any contrast agent and at different time points in at least one cardiac cycle of the subject, respectively at a series of points along a centerline within the segment of the blood vessel, wherein each of the series of sequences of measurements contains blood velocity information or blood pressure information;

a profile generating module, configured to generate a series of profiles from the series of sequences of measurements respectively, wherein each of the series of profiles is a velocity profile or a pressure profile; and an evaluation module, configured to evaluate physiological properties of at least one selected subsegment within the segment of the blood vessel, each between two of the series of points comprising a first end point and a second end point along a blood flow direction, wherein the evaluation module comprises:

a calculation sub-module, configured to calculate a transfer function corresponding to each of the at least one selected subsegment, wherein the transfer function is configured to generate an output waveform given an input waveform, using a waveform corresponding to a profile for the first end point and a waveform corresponding to a profile for the second end point as the input waveform and the output waveform respectively, wherein the transfer function is not implemented in a time domain, wherein the transfer function is implemented in a frequency domain, and is calculated as:

$$SM(f)=\text{Moutput}(f)/\text{Minput}(f);$$

where f is frequency, Moutput(f) is the output waveform, and Minput(f) is the input waveform; and a determination sub-module, configured to determine a physiological property of the blood vessel corresponding to the each of the at least one selected subsegment based on the transfer function.

18. A system for evaluating physiological properties of a segment of a blood vessel in a subject, comprising the processing device and the measuring device according to claim 17 a. wherein the measuring device is configured to acquire, at different time points in one cardiac cycle of the subject, the series of sequences of measurements at the series of points along the centerline within the segment of the blood vessel respectively.

19. The system of claim 18, wherein the measuring device comprises at least one of a magnetic resonance imaging (MRI) device, a Doppler ultrasound device, or a catheter, wherein each of the series of sequences of measurements contains blood velocity information.

20. The system of claim 18, wherein the measuring device comprises at least one of a catheter, a tonometric device, or a fitness wristband capable of measuring blood pressure, wherein each of the series of sequences of measurements contains blood pressure information.

* * * * *